US011517583B2

(12) United States Patent
Patzel et al.

(10) Patent No.: US 11,517,583 B2
(45) Date of Patent: Dec. 6, 2022

(54) TRANS-SPLICING RNA (TSRNA)

(71) Applicant: NATIONAL UNIVERSITY OF SINGAPORE, Singapore (SG)

(72) Inventors: Volker Patzel, Singapore (SG); Sushmita Poddar, Freiburg (DE)

(73) Assignee: NATIONAL UNIVERSITY OF SINGAPORE, Singapore (SG)

(*) Notice: Subject to any disclaimer, the term of this patent is extended or adjusted under 35 U.S.C. 154(b) by 131 days.

(21) Appl. No.: 16/090,226

(22) PCT Filed: Mar. 31, 2017

(86) PCT No.: PCT/SG2017/050183
§ 371 (c)(1),
(2) Date: Sep. 29, 2018

(87) PCT Pub. No.: WO2017/171654
PCT Pub. Date: Oct. 5, 2017

(65) Prior Publication Data
US 2019/0111072 A1  Apr. 18, 2019

(30) Foreign Application Priority Data

Apr. 1, 2016 (GB) .................................... 1605586

(51) Int. Cl.
| A61K 31/7105 | (2006.01) |
| C12N 15/85 | (2006.01) |
| A61P 25/14 | (2006.01) |
| A61P 25/28 | (2006.01) |
| A61P 31/12 | (2006.01) |
| A61P 31/04 | (2006.01) |
| A61P 35/00 | (2006.01) |
| A61K 48/00 | (2006.01) |
| C12N 15/113 | (2010.01) |
| C12N 15/64 | (2006.01) |

(52) U.S. Cl.
CPC .......... *A61K 31/7105* (2013.01); *A61K 48/00* (2013.01); *A61P 25/14* (2018.01); *A61P 25/28* (2018.01); *A61P 31/04* (2018.01); *A61P 31/12* (2018.01); *A61P 35/00* (2018.01); *C12N 15/113* (2013.01); *C12N 15/64* (2013.01); *C12N 15/85* (2013.01)

(58) Field of Classification Search
None
See application file for complete search history.

(56) References Cited

U.S. PATENT DOCUMENTS

| 2005/0202448 A1 | 9/2005 | Lee et al. |
| 2014/0286905 A1 | 9/2014 | Lee |
| 2015/0250901 A1 | 9/2015 | Bauer et al. |

FOREIGN PATENT DOCUMENTS

| CN | 103732739 A | 4/2014 |
| EP | 2746388 A2 | 6/2014 |
| JP | 2015/534811 A | 12/2015 |
| KR | 10-2011-0036996 A | 4/2011 |
| WO | 2000009734 A2 | 2/2000 |
| WO | 2004/038380 A2 | 5/2004 |
| WO | 2014068063 A1 | 5/2014 |

OTHER PUBLICATIONS

Sushmita Poddar, Chapter 4, Results, Trans-splicing RNA molecules for 3' and 5' exon labelling (EL) targeting alpha-fetoprotein (AFP), RNA trans-splicing for selective killing of virus transduced or cancer cells, Jan. 2016, p. 67-110, PhD thesis, National University of Singapore.
Ingermarsdotter et al. "Expression of Herpes Simplex Virus Thymidine Kinase/Ganciclovir by RNA Trans-Splicing Induces Selective Killing of HIV-Producing Cells" Molecular Therapy: Nucleic Acids, 2017, vol. 7, pp. 140-154.
The design and optimization of RNA trans-splicing molecules for skin cancer therapy, Molecular Oncology, vol. 7, No. 6, Dec. 1, 2013. pp. 1056-1068, XP55099110, ISSN: 1574-7891.
Wang et al. "Wdr66 is a novel marker for risk stratification and involved in epithelial-mesenchymal transition of esophageal squamous cell carcinoma" BMC Cancer, 2013, vol. 13, article No. 137, p. 1-10.

*Primary Examiner* — Tracy Vivlemore
(74) *Attorney, Agent, or Firm* — Maschoff Brennan

(57) ABSTRACT

The invention concerns a trans-splicing RNA (tsRNA) molecule comprising one or multiple unstructured binding domains; a cell or vector comprising said tsRNA; and a method for killing cells or treating a disease using said tsRNA.

25 Claims, 32 Drawing Sheets
Specification includes a Sequence Listing.

a d

TRANS-SPLICING RNA (TSRNA)

FIELD OF THE INVENTION

The invention concerns a trans-splicing RNA (tsRNA) molecule comprising one or multiple unstructured binding domains; a cell or vector comprising said tsRNA; and a method for killing cells or treating a disease using said tsRNA.

The sequence listing disclosed herein is included in a text file having the name "Sequence_Listing," created on Jun. 25, 2020, having a size of 938,811 bytes. The foregoing text file is incorporated herein by reference.

The patent or application file contains at least one drawing executed in color. Copies of this patent or patent application publication with color drawing(s) will be provided by the Office upon request and payment of the necessary fee.

BACKGROUND OF THE INVENTION

Spliceosome-meditated RNA trans-splicing (SMaRT) is the process by which two distinct precursor messenger RNAs (pre-mRNAs), or other spliceable RNAs, are joint in trans to generate a chimeric RNA molecule in the nucleus that, after nuclear export, triggers the formation of a chimeric protein in the cytoplasm. This technology can be used to repair defective RNA, e.g. by replacing a mutated with an intact exon, or to label an endogenous message with a functional sequence.

However, trans-splicing-based repair is difficult to achieve because durable repair requires the trans-splicing RNA to be delivered continuously or to be expressed endogenously after genomic integration, it also requires precise splicing towards the intended splice sites within the target, and it must be efficient enough to trigger the therapeutic phenotype despite strong competition with regular cis-splicing.

Trans-splicing-based labelling with a functional sequence concerns, for example, an RNA coding for a fluorescent protein to monitor the expression of genes in living cells or a death signal to selectively trigger death of cells expressing aberrant transcripts in a suicide gene therapy approach. An aberrant transcript can be a biomarker for diseased cells such as transcripts of oncogenes specific for cancer or viral transcripts. The death signal can be triggered by a) a direct signal such as a toxin e.g. diphtheria or the cholera toxin, b) an apoptotic gene such as a caspase, or c) an enzyme such as the herpes simplex virus thymidine kinase (HSVtk) that triggers a death signal upon co-delivery of a drug like ganciclovir (GCV). Direct toxins a) or apoptotic signals b) can immediately trigger cell death which, unfortunately, increases the risks involved with unspecific targeting or off-targeting. This makes the regulatory approval of such technologies problematical. In contrast, the use of a combination of two components c) which, by themselves, are not toxic to the cells represents a much safer approach.

As a therapy, trans-splicing-triggered cell death is easier to achieve than trans-splicing-based repair because the trans-splicing construct needs to be delivered only once into the target cells and so long-term expression is not necessary. Moreover, alternative on-target trans-splicing, i.e. trans-splicing towards the right target but involving any splice sites of that target, is not disadvantageous but instead contributes to a target-specific death signal and trans-splicing doesn't need to be highly efficient to trigger a signal that is strong enough to kill the targeted cells.

Based on the HSVtk/GCV-system we have developed an efficient trans-splicing-based suicide gene therapy approach. We have designed new trans-splicing RNAs both for 5' and 3' exon replacement (ER), i.e. for attaching a suicide gene or a component of a suicide gene system such, as the HSVtk, either to the 5' or 3' end of the target message. We have investigated RNA structure design to improve both on-target activity and specificity of trans-splicing RNA (tsRNA).

STATEMENTS OF THE INVENTION

According to a first aspect, there is provided a trans-splicing RNA molecule comprising: at least one binding domain specific for at least a part of a gene that associates with or is a biomarker for a disease to be treated;

nucleic acids encoding at least one suicide protein or a protein that is a component of a suicide system; and at least one splice signal; wherein said binding domain comprises a binding site comprising at least 25, more preferably 35, even more preferably 45, and most preferably 55 or more consecutive unstructured nucleotides (nt) having no internal binding and/or self-complementary sequences and; said binding domain, when of a length of 44 nt or longer, within or outside said binding site said binding domain has at least one, or a plurality of, mismatch nucleotide(s) with respect to said gene.

Reference herein to of a gene that associates with or is a biomarker for a disease to be treated is reference to a gene that is characteristic of said disease and so is exclusively or preferentially present or expressed when said disease occurs.

Reference herein to a protein that is a component of a suicide system is reference to a protein that interacts with at least one other molecule to trigger or result in death of a cell in which said protein is expressed.

Those skilled in the art will appreciate that the tsRNA has nucleotides complementary to a gene with which it is to bind and because it is RNA will include the nucleotides adenosine, guanosine, cytidine or uridine and the respective bases adenine, guanine, cytosine, and uracil or known chemical modifications of the same.

As those skilled in the art know, RNA is a chain of nucleotides, but unlike DNA, it is often found in nature as a single-strand folded onto itself due to the presence of self-complementary sequences that allow parts of the RNA to fold and pair with itself to form a highly structured molecule. Thus, reference herein to an unstructured state is reference to a state within said binding site where the sequence of RNA nucleotides exists in an unfolded chain. This chain may be curved or bent but it is not folded; thus there is no internal binding or self-complementary sequences.

As an alternative, a further way of describing an unstructured state is where said binding site comprises a sequence predicted not to fold into a stable minimum free energy secondary structure (Gibbs free energy of RNA secondary structure formation $\Delta G \geq 0$ kcal/mol) or is at least less structured than the average of possible binding domains ($\Delta G > \Delta G_{average}$). While RNAfold indicates such structures as open circle, mfold would not give any result for structures with $\Delta G \geq 0$ kcal/mol.

In favoured embodiments said binding domain is not fully complementary to the target gene, or pre-mRNA, and so said binding domain does not form perfect duplexes with the target gene and, usually, is not longer than 200 bp, most usually not longer than 100 bp.

In certain embodiments of the invention said binding domain, including said binding site, comprises a sequence of nucleotides selected from the list comprising or consisting of: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 or more nucleotides.

In yet further certain embodiments of the invention said binding domain comprises a sequence of nucleotides that is at least 50%, 55%, 60%, 65%, 70%, 75%, 80%, 85%, 90%, 91%, 92%, 93%, 94%, 95%, 96%, 97%, 98%, 99% or 100% complementary to said part of said gene that associates with or is a biomarker for a disease to be treated. Ideally, the mismatches in said binding domain are positioned in way to avoid any stretches of 45 nt or longer that are perfectly complementary to the target, including or excluding said binding site, and ideally at least 5 nucleotides from the 5' or 3' end. We think these features most likely act by suppressing antisense effects including A-to-I editing that might result from the formation of long double-stranded RNA in the nucleus. These features appear to be particularly beneficial in 3'ER.

In certain embodiments the binding domain, particularly when it is short i.e. less than 100 nucleotides including the binding site, is located adjacent a spacer sequence that helps to maintain the unstructured nature of the binding domain and so the tsRNA also includes a spacer sequence, known to those skilled in the art, adjacent said binding domain.

Those skilled in the art will appreciate that said binding domain can be designed to bind to any biomarker of any disease and, providing it has the recited features, efficient trans-splicing will occur. Thus the suicide gene therapy constructs or sequences described herein can easily be reprogrammed to target alternative diseases or diseased tissue simply by exchanging the target binding domains.

In yet further certain embodiments of the invention said trans-splicing RNA molecule comprises a plurality of said binding domains which are complementary to the same or different parts of a gene that associates with or is a biomarker for a disease to be treated. Where the further binding domain is for the same part of the gene we have found it significantly improves specific on-target trans-splicing. Where the further binding domain is for a different part of the gene or even a different gene we have found it enhances trans-splicing activity and improves the trans-splicing phenotype.

Indeed, we have found that the specificity of trans-splicing with the intended target splice site was improved 6-fold by designing trans-splicing RNA (tsRNA) comprising multiple target binding domains. In addition, or as an alternative to the afore, we also found that the inclusion in the tsRNA, outside the binding domain, of at least one cis-binding or self-binding domain shielded the trans-splice site in the absence of the target DNA. The inclusion of both multiple target binding domains and at least one of said cis-binding domains improved the specificity of trans-splicing 10-fold and the trans-splicing activity more than 2-fold. Therefore in certain embodiments said tsRNA further comprises at least one cis-binding domain located outside said binding domain.

In certain further embodiments said tsRNA is either 5' or 3' tsRNA.

While unstructured, mismatched target binding domains significantly improved both 5' or 3' exon replacement, either 3'ER or 5'ER was improved by increasing the thermodynamic stability of the tsRNA 3' end. This was undertaken by creating a highly structured 3' end by inserting therein an RNA chain of nucleotides that is folded, or pairs with itself, due to the presence of self-complementary sequences, to form a highly structured molecule. An example of a highly structured RNA chain for insertion into the tsRNA is a hammerhead ribozyme sequence, a hairpin loop forming sequence, or a y-shaped structure forming sequence, however, other such structure are known by those skilled in the art and so can be used for this purpose. Accordingly, other certain embodiments comprise at least one 3' highly structured RNA sequence. We think this feature most likely acts by stabilizing the trans-splicing RNA and protecting it from ribonucieolytic degradation. This feature appears to be particularly beneficial in 5'ER. Further formation of the active ribozyme, hairpin loop, or Y-shaped structure was supported by inserting a spacer between the ribozyme and the polyA site. 5'ER was improved by inserting a cis-cleaving tertiary structure stabilized (second generation) hammerhead ribozyme between the binding domains and the polyadenylation site, or when other highly stable RNA chains were used, then between theses stable RNA chains and the polyadenylation site. This feature removes the polyA tail of the trans-splicing RNA which then cannot be exported anymore into the cytoplasm increasing its nuclear concentration and trans-splicing activity. This feature also avoids that trans-splicing RNA for 5'ER can be exported, translated, and trigger a phenotype in the absence of trans-splicing.

Our work shows that these optimised tsRNAs efficiently triggered the death of HPV-16 or AFP-positive cells. Thus, spliceosome-mediated RNA trans-splicing represents a promising therapeutic strategy to trigger cell death in suicide gene therapy approaches.

In other embodiments said disease is cancer or a viral infection or a bacterial infection or an acquired genetic disease caused by mutations triggered by transposable elements, radiation, chemicals, or unknown triggers.

In the first instance said cancer is selected from the group comprising: hepatocellular carcinoma (HCC), cervical cancer, vaginal cancer, vulvar cancer, penile cancer, skin cancers, melanoma including malignant melanoma, squamous-cell carcinoma, basal-cell carcinoma, Merkel cell carcinoma, lung cancer, cell bladder cancer, breast cancer, colon or rectal cancer, anal cancer, endometrial cancer, kidney cancer, leukemia, acute myelogenous or myeloid leukemia (AML), acute lymphoblastic leukemia (ALL), chronic lymphotic leukemia (CML), chronic myelogenous or myeloid leukemia (CML), hairy cell leukemia (HCL), T-cell prolymphocytic leukemia (P-TLL), large granular lymphocytic leukemia, adult T-cell leukemia, lymphoma, myeloma, non-Hodgkin lymphoma, pancreatic cancer, prostate cancer, thyroid cancer, nasopharyngeal cancer, mouth or throat cancer, oropharyngeal cancers, stomach cancer, brain tumours, bone cancer, and stem cell cancers and, indeed other cancers that would benefit from the treatment disclosed herein.

In the second instance said viral infection is selected from the group comprising: Papillomaviruses, human papillomavirus type 16, human papillomavirus type 18, retroviruses, lentiviruses, herpes viruses, adenovirus, adeno-associated virus, Flu virus, Hepatitis virus, Hepatitis B virus (HBV), Hepatitis C virus (HCV), Epstein-Barr virus (EBV), human T-cell lymphotropic virus (HTLV), human immunodeficiency virus (HIV), human immunodeficiency virus type 1 (HIV-1), and human immunodeficiency virus type 2 (HIV-2), and others.

In the third instance said bacterial infection is selected from the group comprising: *Bartonella henselae, Francisella tularensis, Listeria monocytogenes, salmonella* species, *Salmonella typhi, Brucella species, Legionella* species. Mycobacteria species, *Mycobacterium tuberculosis, Nocardia* species, *Rhodococcus* species, *Yersinia* species, *Neisseria meningitides* and others.

In the last instance said acquired genetic disease is selected from the group comprising: Neurofibromatosis 1 and 2, Mc Cune Abright, Duchenne muscular dystrophy (DMD), Epidermolysis bullosa, Fanconi A and C, Philadelphia chromosome, Hemophilia A and B, cystic fibrosis, Muckle Wells syndrome, lipoprotein lipase deficiency, B-thalassemia, pyruvate dehydrogenase complex deficiency, and others.

In an alternative aspect there is provided a medicament comprising said tsRNA according to the invention and, optionally, at least one further component of said suicide system effective to trigger death of a cell expressing said trans-spliced RNA.

In an alternative aspect there is provided a pharmaceutical composition comprising said tsRNA according to the invention; optionally, at least one further component of said suicide system effective to trigger death of a cell expressing said trans-spliced RNA; and a carrier suitable for human or veterinary use.

In the afore optional instance said further component may be, e.g., ganciclovir, although other known co-component suicide systems for cell death may be used. Examples are cytosine deaminase-5-fluorocytosine, cytochrome P450-ifosfamide, cytochrome P450-cyclophosphamide, and nitroreductase-5-[aziridin-1-yl]-2,4-dinitrobenzamide.

In an alternative aspect there is provided a cell containing said tsRNA or a vector containing said tsRNA.

In a further aspect there is provided method of killing a cell comprising transfecting, lipofecting, transducing, electroporating, nucleofecting or transforming said cell with tsRNA or a vector containing the tsRNA according to the invention and, optionally, exposing said cell to at least one other component of said suicide system effective to trigger death of a cell expressing said trans-spliced RNA.

In this embodiment the invention is typically practiced in vitro.

In a further aspect there is provided a method of treating a disease comprising transfecting, lipofecting, transducing, electroporating, nucleofecting or transforming a diseased cell with tsRNA or a vector containing the tsRNA according to the invention ex vivo or in vivo and, optionally, exposing said cell to at least one other component of said suicide system effective to trigger death of a cell expressing said trans-spliced RNA.

In a further aspect there is provided a method of targeting a diseased cell comprising topical application (including a cream, a gel, a foam, a lotion, ointment or aerosol), intranasal application, alveolar application, systemic application, oral application, intravenous application, intramuscular application, subcutaneous application, cutaneous application, intraperitoneal application, or injection into a tumor with tsRNA or a vector containing the tsRNA according to the invention in vivo and, and, optionally, exposing said cell to other components of said suicide system effective to kill said cell.

In a certain methods of the invention said cell is a virally transformed cell. Typically the cell is transformed with a virus selected from the group comprising: Papillomaviruses, human papillomavirus type 16, human papillomavirus type 18, retroviruses, lentiviruses, herpes viruses, adenovirus, adeno-associated virus, Flu virus, Hepatitis virus, Hepatitis B virus (HBV), Hepatitis C virus (HCV), Epstein-Barr virus (EBV), human T-cell lymphotropic virus (HTLV), human immunodeficiency virus (HIV), human immunodeficiency virus type 1 (HIV-1), and human immunodeficiency virus type 2 (HIV-2).

In yet other methods of the invention said cell is a cancer cell such as a hepatocellular carcinoma (HCC) cell, cervical cancer cell, vaginal cancer cell, vulvar cancer cell, penile cancer cell, skin cancer cell, melanoma cell including malignant melanoma cell, squamous-cell carcinoma cell, basal-cell carcinoma cell, Merkel cell carcinoma cell, lung cancer cell, cell bladder cancer cell, breast cancer cell, colon or rectal cancer cell, anal cancer cell, endometrial cancer cell, kidney cancer cell, leukemia cell, acute myelogenous or myeloid leukemia (AML) cell, acute lymphoblastic leukemia (ALL) cell, chronic lymphotic leukemia (CML) cell, chronic myelogenous or myeloid leukemia (CML) cell, hairy cell leukemia (HCL) cell, T-cell prolymphocytic leukemia (P-TLL) cell, large granular lymphocytic leukemia cell, adult T-cell leukemia cell, lymphoma cell, myeloma cell, non-Hodgkin lymphoma cell, pancreatic cancer cell, prostate cancer cell, thyroid cancer cell, nasopharyngeal cancer cell, mouth or throat cancer cell, oropharyngeal cancer cell, stomach cancer cell, brain tumour cell, bone cancer cell, and stem cell cancer cell. Ideally said cell is mammalian and most typically human.

In the claims which follow and in the preceding description of the invention, except where the context requires otherwise due to express language or necessary implication, the word "comprise", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

BRIEF DESCRIPTION OF THE DRAWINGS

The patent or application file contains at least one drawings executed in color. Copies of this patent or patent application publication with color drawing(s) will be provided by the Office upon request and payment of the necessary fee.

An embodiment of the present invention will now be described by way of example only with reference to the following wherein.

METHODS AND MATERIALS

Figure 1:
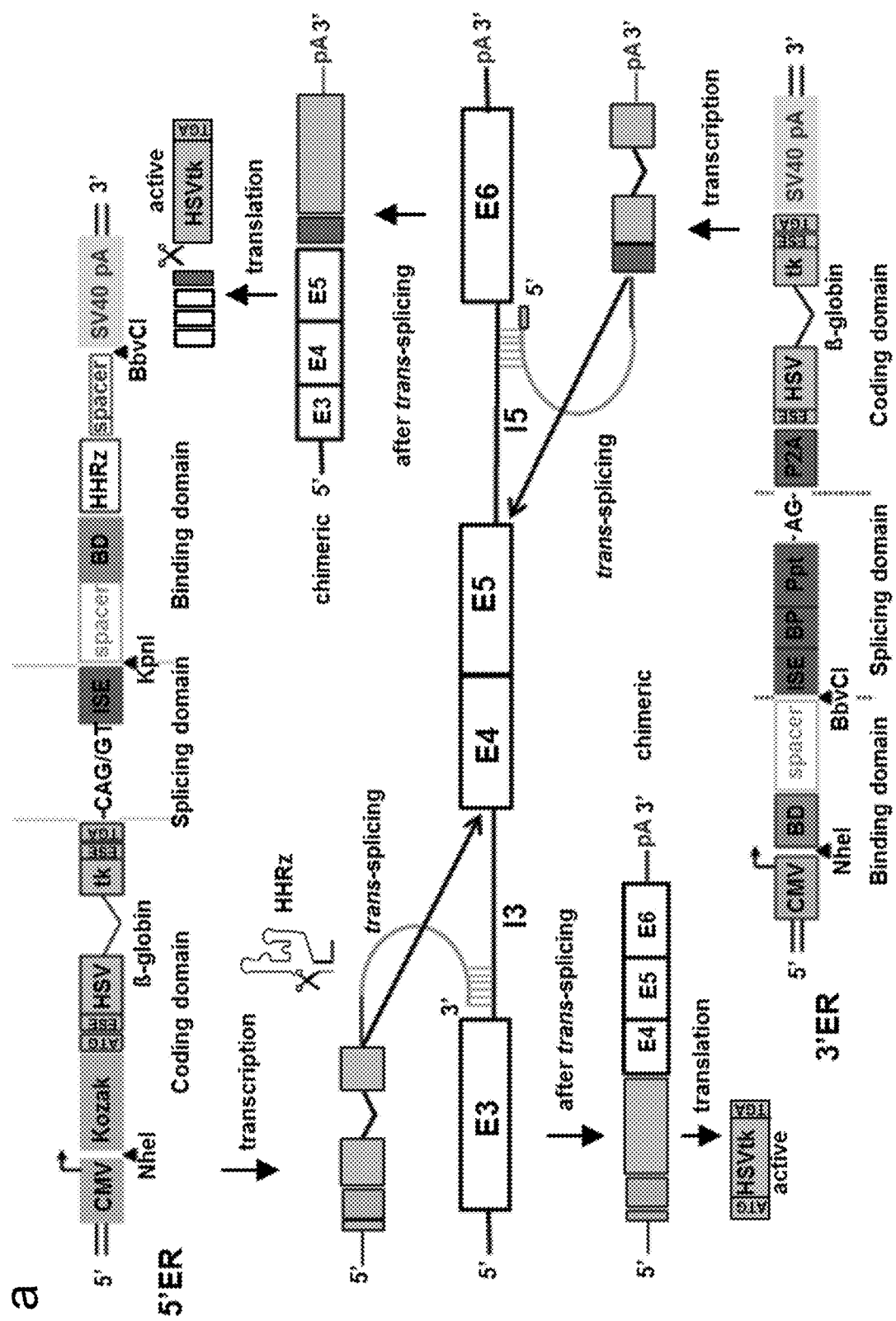
FIG. 1 Detection of trans-splicing of a cell death signal by 5'ER and 3'ER to target AFP in HepG2 tissue culture cells. (a) Illustration showing the two kinds of trans-splicing molecules designed for exon replacement with an HSVtk death signal to alpha fetoprotein (AFP) by either 5' exon replacement (5'ER) or 3' exon replacement (3'ER). The 5'ER construct contains the coding domain HSVtk gene followed by 5' splicing domain with 5' donor splice site and 50 base pair binding domain recognizing the intron 3 of AFP gene. The self-cleaving HH Rz is attached to release the BD from the polyA signal. The 3'ER construct contains a 50 base pair BD targeting AFP intron 5 followed by 3' splice signals, P2A and HSVtk coding region. A proteolytic cleavage site P2A is attached for HSVtk cleaving from AFP-HSVtk fusion protein after successful trans-splicing. HSVtk, Herpes Simplex Virus thymidine kinase; ISE, intronic splice enhancer; BD, binding domain; HH Rz, Hammerhead ribozyme; BP, branch point; Ppy, polypyrimidine tract. (b) Quantitative real time RT-PCR showing raw threshold cycles (Ct) of cis-splicing and trans-splicing upon the introduction of trans-splicing constructs in context of over-expressed AFP_E3-E6 mini-gene with 5'ER (top panel) and 3'ER (bottom panel). Two set of TaqMan probes AFP (binds at exon 4 for 5'ER and exon 6 for 3'ER, left panel) and HSVtk (binds at distal part for 5'ER and proximal part for 3'ER, right panel) were used for detection. Beta-actin used as an internal control. n=3, mean±SEM. (c) Conventional two-step PCR of 30+30 cycles was performed to observe the 5' (top) and 3' (bottom) splicing events with over-expressed AFP on a 1% agarose gel and the splice junctions confirmed by sequencing. C, cis; T, trans. (b) and (c) Mock_HepG2 shows endogenous levels of AFP cis-splicing detection (b, left panel and c, top and bottom last lane). (d) and (e) shows the drop in cis-splicing levels when active 5' (d) and 3' (e) trans-splicing constructs are introduced along with AFP mini-gene. Raw Ct values of cis and trans-splicing represents the outcome of a bimolecular reaction of splicing events. n=3, mean±SEM. (f) Splicing events at endogenous target AFP represented as Ct values. n=3, mean±SEM. (g) Conventional PCR of 35+35 cycles showing endogenous C and T levels in active 3'ER (top panel) and 5'ER (bottom).
Figure 1:
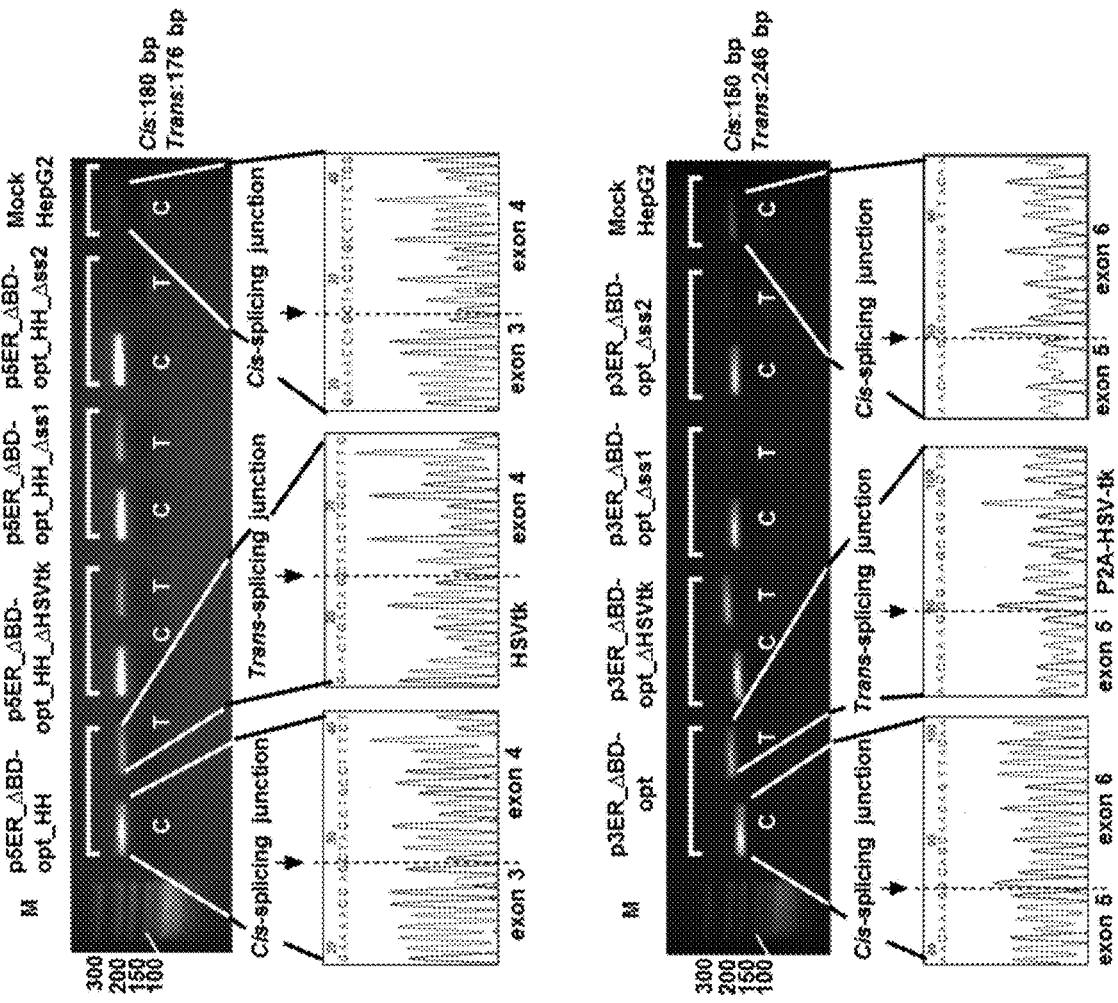

RNA design: The trans-splicing constructs were designed combining various reported and novel molecular features to improve activity and target specificity. The 3'ER ts constructs consisted of a CMV promoter (pEGFP-N1, Clontech acc no. U55762) followed by a binding domain (BD) of 50 bases complementary to the target AFP intron 5. The BD included two mismatches at positions 18 and 19 to inhibit potential antisense (as) effects that can be triggered by longer dsRNA in the nucleus of the cell. Software 'foldanalyze' (HUSAR, DKFZ) was used to select short unstructured BDs within the complete antisense RNA structure space that can be directed against the AFP intron 5. Structures of the selected BDs were confirmed by RNA 2° structure (minimum free energy and centroid) predictions using software tools mfold and RNAfold. Such selected BDs were then fused with the rest of the trans-splicing RNA making sure that the BDs remained unstructured upon fusion and were not involved in base-pairing the trans-splicing or coding domains which was achieved by implementing suitable spacers. The selected 3' splice signal (3' ss) was designed to functionally compete with the cellular cis-splice site and was supported by an intronic splice enhancer (ISE) (McCarthy, et al., 1998; Konczak, et al., 2000; Yeo et al., 2004), a branchpoint (BP) (Eul, 2006) and polypyrimidine tract (Ppt) (Nobel, et al., 1998; Taggart, et al, 2012). The HSVtk cds was preceded with a sequence coding for a proteolytic cleavage site P2A (Kim, et al, 2011) to ensure endogenous release of the native HSV-tk from the AFP-HSVtk fusion protein that initially results from the trans-splicing process. The HSVtk gene is devoid of a start codon and can only be translated after trans-splicing using the translational start of the target message. The HSVtk gene was equipped with an A/G-rich exonic splice enhancer (ESE) generated by using degenerative alternative codons that do not after the HSV-tk amino acid sequence (Fairbrother, et al, 2002; Jin et al., 2003) (supplementary FIG. 1a). A beta-globin mini-intron of 133 bases (pCMVTNT™, acc num. AF477200.1) was introduced in the HSVtk gene at a splice site consensus motif (3' ss CAG/G and 5' ss MAG. For transcriptional termination the SV40 polyA sequence (pcDNA3.1, Life Technologies) was used.

The 5'ER ts constructs were designed with the same molecular features as p3ER but with different orientation including a translational signal motif along with the CMV promoter. All the structural elements important for translation of eukaryotic mRNA were included: original cap site of AFP (Gibbs, et al. 1987) followed by the consensus Kozak sequence GCCRGCCAUGG (Kozak, 1995, 1999, 2005). Immediately after the translation start signal was the coding domain HSVtk inclusive of the ESE and mini intron followed by a 5' ss signal (Freund, et al. 2005). The 5' BD was designed in a similar way with mismatches at positions 24 and 25 to avoid as-effects. Following the BD, a hammerhead ribozyme (HH Rz) (Saksmerprome, et al. 2004) was incorporated for enhanced cleaving of the BD after delivery into the nucleus. The HH RZ is followed by a long spacer to isolate the polyA from the ribozyme followed by the SV40 polyA.

Mutation designs: The 3'/5'ΔHSVtk were designed to produce a full-length inactive HSVtk protein with two point mutations: A to G at position 115 (glycine to glutamic acid), G to A mutation at position 649 (histidine to arginine) (Sasadeusz, et al. 1997). The 3/5'Δss were designed to check the importance of having an active splice signal, mutation in the ss should result in reduced ts. The 3'Δss1 had the conserved BP changed from A to C, 3'Δss2 had 6/8 nucleotides changed including the BP and both the ss has mutated AG to TC acceptor ss. The 5'Δss1 had 7/11 bases changed with consensus donor ss GT intact and 5'Δss2 had 10/11 bases changed including the mutation of donor ss from GT to AC. The 5'ΔHH Rz had the conserved cleavage motif GUC changed to ACA to eliminate or greatly reduce the cleaving efficiency of the ribozyme.

Plasmid construction: The 3' and 5' parental exon replacement (ER) constructs named p3ER_ΔBD-opt and p5ER_ΔBD-opt_HH respectively were gene synthesised (GeneArt, Regensburg) and cloned into pVAX1 (AddGene) using SpeI and BbsI to be used as master vectors to sub-clone the remaining of the trans-splicing constructs. The AFP mini-gene consisting of exons 3-6 and introns 3 and 5 (AFP_E3-E6) derived from NCBI (acc num M16110) was gene synthesised (GeneArt, Regensburg) and cloned into pVAX1 using NheI and KpnI. The HSVtk positive control was sub-cloned from the p3EL and p5EL expression plasmids using SacI and BamHI. The complete 1136 base cds of the HSVtk gene (NCBI acc num AF057310) was gene synthesized as part of trans-splicing construct.

A total of 80 constructs were designed and region of change was either gene synthesised or PCR amplified and were sub-cloned into the p3ER_ΔBD-opt and p5ER_ΔBD-opt_HH parental or master vectors. The p3ER_ΔBD-opt_Δss1 and p3ER_ΔBD-opt_Δss2 are 3' splice site mutations sub-cloned inside p3ER_ΔBD-opt with BbvCI and SacI, NheI and PvuI respectively to replace the wild type ss. Similarly the p5ER_ΔBD-opt_HH_Δss1 was cloned inside p5ER_ΔBD-opt_HH with BssHII and BbsI. The p5ER_ΔBD-opt_HH_Δss2 was synthesised using nested PCR method to generate the desired 5' ss mutation and cloned into the master vector with BssHII and KpnI. The 3' and 5' substitution mutation to generate a weaker HSVtk protein namely p3ER_ΔBD-opt_ΔHSVtk and p5ER_ΔBD-opt_HH_ΔHSVtk was cloned into their parental vectors using PvuI and PstI, PstI and NheI respectively. The 5'HH Rz mutation namely p5ER_ΔBD-opt_ΔHH was generated using nested PCR method and cloned into the parental vector with KpnI and BbvCI. The p3ER_BD-opt with NheI and BbvCI and p5ER_BD-opt_HH with KpnI and BbvCI were sub-cloned to generate the BDs with no mismatch (state-of-the-art BDs) with the target. The p3ER_BD(-) was generated by removing the BD from the p3ER_ΔBD-opt with NheI and BbvCI and replacing a small oligo with same RE overhang. However the p5ER_BD(-)_HH and p5ER_BD(-)_ΔHH were generated by replacing the 5'BD with a random 8-mer to bind with the stem Ill of the HH Rz, sub-cloning into the parental vector with KpnI and BbvCI. The p5ER_ΔBD-opt_HH(-) with no HH was sub-cloned using KpnI and BbvCI. The 3' structured BDs namely p3ER_ΔBD-struc1, p3ER_ΔBD-struc2 and p3ER_BD-opt-inv were sub-cloned using NheI and BbvCI. The 5' structured BDs namely p5ER_ΔBD-struc1_HH and p5ER ΔBD-opt-inv_HH were sub-cloned with KpnI and BbsI. More 5'ER constructs to look at the stability of the 3' end of the RNA like p5ER_ΔBD-opt_hp_HH and p5ER_ΔBD-opt_Y_HH were cloned inside the parental using KpnI and BbsI. Additional BDs to study the specificity of on-target and alternative trans-splicing in the 3'ER namely p3ER_ΔBD-opt_D, p3ER_ΔBD-opt_E, p3ER_ΔBD-opt_F, p3ER_ΔBD-opt_EF, p3ER_ΔBD-opt_DEF and p3ER_BD(-)_D were cloned into the parental using NheI and BbvCI. To further study the effects of these sub-optimal trans-splicing constructs in context to splice mutants, they were cloned into the p3ER_ΔBD-opt_Δss1 and p3ER_ΔBD-opt_Δss2 for 3' set and p5ER_ΔBD-opt_HH_Δss1 and p5ER_ΔBD-opt HH_Δss2 for 5' set. The 3' structured BDs (6 different constructs: p3ER_ΔBD-struc1/2/opt-inv_Δss1/2), 3' no mismatch BDs (2 constructs: p3ER_BD-opt_Δss1/2) and 3' no BDs (2 constructs: p3ER_BD(-)_Δss1/2) were cloned using NheI and BbvCI. The 5' structured BDs (4 different constructs: p5ER_ΔBD-struc1/opt-inv_HH_Δss1/2), 5' no mismatch BDs (2 constructs: p5ER_BD-opt_HH_Δss1/2), 5' no BDs_wt HH (2 constructs: p5ER_BD(-)_HH_Δss1/2) and 5' no BD_mut HH (2 constructs: p5ER_BD(-)_ΔHH_Δss1/2) were cloned using KpnI and BbvCI. To study the effect of sub-optimal trans-splicing constructs in context of no mismatch or state-of-the-art BDs, the structured BDs were made perfect complementary with the target and cloned into p3ER_ΔBD-opt with NheI and BbvCI (total 3 constructs: p3ER_BD-struc1/2/opt-inv), cloned into p5ER_ΔBD-opt_HH with KpnI and BbsI (total 2 constructs: p5ER_BD-struc1/opt-inv_HH).

To improve overall trans-splicing, constructs were designed to target two pre-mRNAs (one against AFP and the other against either HCCA2, CD24 or VEGF) simultaneously in the 3'ER context, p3ER ΔBD-opt_AFP+HCCA2 and p3ER_ΔBD-opt_HCCA2+AFP were sub-cloned into the p3ER parental vector using NheI and BbvCI. The other targets namely p3ER_ΔBD-opt_AFP+CD24 and p3ER_ΔBD-opt_AFP+VEGF were further sub-cloned into the p3ER_ΔBD-opt_AFP+HCCA2 vector with EcoRI and BbvCI by replacing the HCCA2 serving as the second BD. Similarly p3ER_ΔBD-opt_CD24+AFP and p3ER_ΔBD-opt_EGF+AFP were sub-cloned into the p3ER_ΔBD-opt_HCCA2+AFP vector with EcoRI and NheI by replacing the HCCA2 BD serving as the first BD. For flow cytometry analyses, the GFP gene (amplified from pEGFP.C2) was cloned into pGL3-control using HindIII and XbaI, the SV40 promoter-GFP-SV40 polyA-SV40 enhancer cassette from pGL3 plasmid was cloned into a self-generated MCS site in pVAX1-trans-splicing vectors using BglII and SalI. The GFP cassette in pVAX1-AFP negative control vector was cloned directly using KpnI and BamHI. To generate the trans-splicing constructs targeting HPV16 genes, the BD from the parental vector p3ER ΔBD-opt was digested with Bam HI and XhoI and replaced with BDs E1a and E5 to generate p3ER ΔBD-opt_E1a and p3ER_ΔBD-opt_E5 respectively. Similarly BDs E2 and E6 were cloned into p3ER ΔBD-opt by replacing AFP BD using XhoI and XbaI to generate p3ER_ΔBD-opt_E2 and p3ER_ΔBD-opt_E6. For 5'ER, the parental vector p5ER_ΔBD-opt_HH containing AFP BD was replaced with HPV16 BD E1b with enzymes HindIII and BamHI to generate p5ER_ΔBD-opt_E1b_HH and p5ER_ΔBD-opt_HH(-) vector's AFP BD was replaced with E6 BD to form p5ER_ΔBD-opt_E6_HH(-) with HindIII and BamHI.

Dumbbell (db) construction: Generating dumbbells for trans-splicing from the plasmid vectors was done using the ELAN method of db production. The Enzymatic Ligation Assisted by Nucleases (ELAN) is a three step process which includes digestion of the transcription cassette from the plasmid, ligation of the closing loops on either side followed by exonuclease treatment to eliminate the unclosed db plasmids.

(a) Phosphorylation of Stem-Loop Primers

The stem loops consisting of individual RE site were synthesised by AIT Biotech (Singapore) and was phosphorylated using the following reaction shown in Table 1:

TABLE 1

| Reaction setup for stem-loop phosphorylation using polynucleotide kinase (PNK) | |
|---|---|
| COMPONENTS | STEM LOOP PRIMERS |
| Stem loop oligo 10 μM | 60 pmoles |
| 10X Buffer A | 2 μL |
| PNK enzyme | 1-2 U |
| 10 mM ATP | 2 μL |
| Water nuclease-free | Make up volume |
| TOTAL | 20 μL |

The Stem-loop primers were Stem loop-SpeI and Stem-loop-BamHI.

(b) ELAN Method

In the ELAN loop-ligation method, the gene expression cassette was directly cut out from parental plasmid. 50 times more stem-loops were added in the ligation reaction to ensure that most of the gene expressing cassettes could be capped. By-products such as loop dimers were cleaved by the restriction enzymes and were destroyed during the exonuclease treatment. Detailed setups of the reaction are shown in Table 2.

TABLE 2

Reaction setup for the generation of trans-splicing dumbbells using the ELAN loop-ligation strategy

| COMPONENTS | AMOUNT | CONDITIONS |
|---|---|---|
| Digestion | | |
| Parental plasmid | 6 pmoles | 37° C. incubation for 4 hours and heat inactivation at 65° C. for 15 minutes |
| SpeI RE | 5 U | |
| BamHI RE | 5 U | |
| HindIII RE | 5 U | |
| 10x Fast digest buffer | 5 μL | |
| Water nuclease-free | Make up volume | |
| TOTAL | 50 μL | |
| ELAN reaction | | |
| Digestion mix | 50 μL | 22° C. for 4 hours to overnight and heat inactivation at 85° C. for 5 min |
| Loop-1 | 60 pmoles | |
| Loop-2 | 60 pmoles | |
| 10X Fast digest buffer | 10 μL | |
| 100 mM ATP | 1.5 μL | |
| SpeI RE | 1 U | |
| BamHI RE | 1 U | |
| BglII RE | 1 U | |
| HindIII RE | 1 U | |
| XbaI RE | 1 U | |
| T4 DNA ligase | 3 U | |
| Water nuclease-free | Make up volume | |
| TOTAL | 15 μL | |
| Exonuclease treatment | | |
| ELAN mix | 148 μL | 37° C. incubation for 2 hours and heat inactivation at 85° C. for 5 min |
| T7 DNA polymerase | 10 U | |

Cell Culture: Human hepatocytes (HepG2), human cervical cancer cell lines (Siha, HeLa) and mouse cervical cancer cell line (C3) were maintained at 37° C. in a humidified incubator with 5% CO2 in Dubecco's Modified Eagle's Medium (HyClone, Thermo Scientific), supplemented with 10% Fetal Bovine Serum (HyClone) and 1% penicillin-streptomycin. The cells were passaged every 3-4 days at desired density.

Transfection of plasmid DNAs: HepG2 cells were transfected at ~70-90% confluency in a 6-well plate for Western blotting, 12-well for FACS analyses and 24-well plate for all other analyses using either Lipofectamine 3000 (for FACS studies only) or Lipofectamine 2000, (Life Technologies) according to manufacturer's protocol. A total of 1 μg DNA was co-transfected or transfected in a 24-well plate format (500 ng:500 ng of ts construct: AFP_E3_E6 minigene) in over-expression studies and 1 μg of ts constructs only in endogenous studies. For 12-well and 6-well formats, the amount of total DNA was scaled up to 2 μg and 4 μg respectively. For FACS experiments, either 500 ng of pEGFP-C2 plasmid was co-transfected along with the ts and AFP mini-gene vectors to perform experiments with some 3'ER and 5'ER plasmids and dumbbells, or the GFP infused ts vectors were used along with/without AFP mini-gene for over-expression and endogenous studies respectively.

Total RNA Isolation: RNA was isolated 24 hours post-transfection using RNeasy plus kit (Qiagen) following the manufacturer's protocol. RNA concentrations were measured using NanoDrop 2000.

cDNA conversion and real-time RT-PCR: 500 ng RNA from all samples was converted into cDNA using the First Strand SuperScript RTIII (Invitrogen) kit with 200 ng of random hexamers and 10 uM of dNTPs. The reaction conditions were 25° C. for 5 min, followed by 50° C. for 2 h and enzyme inactivation at 70° C. for 15 min. 20 ng of cDNA was used as template for real time RT-PCR. TaqMan quantification was performed in ABI 7900HT of the cDNAs by designing specific probe and primer sets for each cis- and trans-splicing detection. One set of probes were designed in the AFP regions; namely AFP probe exon 5 and AFP probe exon 4 to detect 3'ER and 5'ER cis and trans-splicing respectively. Primers to detect 3'ER cis-splicing along with AFP probe were FP afp exon 5 (set1) and RP afp exon 6 and for 3'ER trans-splicing were FP afp exon 5 (set1) and RP HSVtk. Primers to detect 5'ER cis-splicing along with AFP probe were FP afp exon 3 and RP afp exon 4 (set1) and for 5'ER trans-splicing were FP HSVtk (set1) and RP afp exon 4 (set1). Another set of probes were designed in the distal HSVtk region to detect 3'ER, named HSVtk probe for 3'ER and proximal HSVtk region to detect 5'ER, named HSVtk probe for 5'ER trans-splicing alone. The primers to detect 3'ER trans-splicing along with HSVtk probes were FP afp exon 5 (set2) and RP HSVtk. Primers to detect 5'ER trans-splicing along with HSVtk probes were FP HSVtk (set2) and RP afp exon 4 (set2). The number of cycles in over-expression studies and endogenous studies were 40 and 50 respectively. RT-PCR: Reverse transcription PCR was performed on the cDNA samples using Taq DNA polymerase (Fermentas) with 60 cycles of two-step PCR (30+30 cycles or 35+35 cycles) to detect 3' and 5' cis and trans-splicing and the bands were visualized on a 1% agarose gel. The primers used to detect 3'ER cis-splicing and mock were FP afp exon 5 (set1) and RP afp exon 6, to detect 3'ER trans-splicing were FP afp exon 5 (set1) and RP HSVtk. To detect 5'ER cis-splicing and mock were primers FP afp exon 3 and RP afp exon 4 (set1), to detect 5'ER trans-splicing were primers FP HSVtk (set1) and RP afp exon 4 (set1). To visualize specific versus alternative on-target trans-splicing, the p3ER_ΔBD and p3ER_BD(-) cDNAs were amplified using primers FP afp exon 5 (set2) and RP HSVtk for specific ts and with primers FP afp exon 3 and RP HSVtk for alternative on-target ts. The p5ER_ΔBD_HH and p5ER_BD(-)_HH cDNAs were amplified with primers FP HSVtk (set2) and RP afp exon 4 (set2) for specific ts and with primers FP HSVtk (set2) and RP afp exon 6 for alternative on-target ts.

Alamar assay: To check the functional activity of trans-splicing, drug Ganciclovir (GCV) (Sigma) was added to the cells at a concentration of 10 μM, 100 μM and no GCV (internal negative control) 24 hours post-transfection followed by addition of AlamarBlue® cell viability reagent (Thermo Scientific) 24 hours post drug for a duration of 6 days with replacement of fresh media and drug every day after each alamar reading. The fluorescence was measured at 230/290 nm after 90 minutes of incubation at 37° C. The positive and negative controls for the assay were designed as mentioned in the manufacturer's protocol.

Single cell gel electrophoresis: Also known as the Comet Assay, it was carried out to check for double-stranded DNA breaks upon 10 μM GCV administration 24 hours post-transfection and cells harvested 24 hours post-drug treatment using alkaline lysis method (Olive, et al., 2006). The comets were stained with Propidium Iodide 10 μg/ml (Life Technologies) and analysed under a fluorescent microscope at 10x and 20x magnifications. Approximately 150-200 comets were scored/sample.

Flow Cytometry: To check for apoptosis, cells were harvested 48 hours post 100 μM GCV treatment and stained using Propidium Iodide and Alexa Fluor 647 Annexin V (Life Technologies) in Annexin-binding buffer according to manufacturer's protocol. The samples were gated based on single live cell populations which were positive for GFP. The final % apoptosis values are indicated as (early and late apoptosis+GCV)−(early and late apoptosis-GCV).

Western Blotting: To detect both AFP and HSVtk proteins, cells were harvested 24 hours post-transfection and a total of 50 μg protein was loaded in a 10% SDS-PAGE, transferred on a PVDF membrane and blocked with 5% milk (w/v). The respective primary antibodies (HSV-tk vL-20 goat polyclonal Santa Cruz cat no. sc-28038, AFP goat polyclonal Santa Cruz cat no. sc-8108 and Beta actin (internal control) rabbit polyclonal Santa Cruz cat no.sc-130656) were incubated in 5% milk overnight at 4° C., followed by 2 hour incubation with secondary antibodies (HSVtk and AFP anti goat Santa Cruz cat no. sc-2020 and Beta actin anti-rabbit Santa Cruz cat no. sc-2357. The blots underwent chemiluminescence using Pierce ECL Western Blotting substrate (Thermo Scientific) and developed in an imager (BioRad).

Prediction of splice sites: The strength and nature of the splice sites were predicted using softwares Alternative Splice Site Predictor (ASSP) (Wang, 2006) http://wangcomputing.com/assp/overview.html and Berkeley Drosophila Genome Project Splice Site Prediction (BDGP SSP) (Reese, et al., 1997) fruitfly.org/seqtools/splice.html using default cut-off values for the splice site predictions. To predict the nature of splice sites in HPV16 genome, ASSP was used to document constitutive or cryptic splice acceptors and donors based on the overall score and confidence generated by the software. The alternative splice sites with confidence >0.89 and score >5.5 and constitutive splice sites with confidence >0.1 and score >7.7 besides the documented splice sites (Johansson, 2013 and Schmitt, et al, 2011) were selected for the trans-splicing analyses.

Results and Discussion

De Novo Designed Trans-Splicing RNA for 5' and 3' Exon Replacement (ER) Triggers Targeted Trans-Splicing Towards an Overexpressed or Endogenous Pre-mRNA Target This invention refers to novel optimized RNA sequences and structures designed to achieve higher trans-splicing activity and specificity. We designed parental trans-splicing RNA (tsRNA) molecules both for 5'ER or 3'ER comprising the following molecular features (FIG. 1a): Firstly, computationally selected unstructured binding domains (BD) of about 50 nt in length complementary to intron 3 or 5 of AFP pre-mRNA and a spacer preserving the selected BD structure in the context of the tsRNA molecule; secondly, a splicing domain composed of an intronic splice enhancer (ISE) and a consensus splice donor (SD) site (CAG/GT) for 5'ER or an ISE, a consensus YNYURAC (R purine, Y pyrimidine, N any nucleotide) branch point (BP) sequence, an extensive polypyrimidine tract (PPT), and a consensus splice acceptor (SA) site (AG/G) for 3'ER; and thirdly, a coding domain including an optimized HSVtk gene harbouring a novel strengthened exonic splice enhancer (ESE) as well as the α-globin mini-intron.

In addition, we furnished the tsRNA for 5'ER with a tertiary structure-stabilised hammerhead ribozyme (HHRz) (Saksmerprome, et al. 2004) positioned downstream of the BD to crop itself together with the SV40 polyA site in order to trigger nuclear RNA retention and to avoid trans-splicing-independent HSVtk expression. Formation of the active ribozyme structure was supported by inserting a spacer between the ribozyme and the polyA site. The tsRNA for 3'ER, on the other hand, was equipped with the P2A proteolytic cleavage site (Kim J H, et al. 2011) positioned immediately downstream of the splice acceptor SA site to trigger proteolytic release of the HSVtk from the chimeric fusion protein which results from the trans-splice reaction. The constructs were designed for maximum activity.

Central 2 nt target mismatches were included into the binding domains (ΔBD) to avoid that target binding generates long double-stranded nuclear RNA which might trigger antisense effects, including A-to-I editing by adenosine deaminases acting on RNA (ADARs), which could impair the trans-splice strategy. That way optimised BDs for 3' or 5'ER were termed p3ER_ΔBD-opt or p5ER_ΔBD-opt_HH. As controls we designed for 5' and 3'ER each two splice site mutants (Δss1 and Δss2), the partly inactive HSVtk mutant (A to G mutation at position 115 and a G to A mutation at position 649 of HSVtk gene), and for 5'ER a control harbouring an inactive HHRz cleavage site (FIG. 3a). To test the tsRNAs, we designed a vector for the over-expression of an AFP mini-gene encompassing the sequence from exon 3 to exon 6 (E3 to E6) including intron 3 (I3) and 5 (I5) but lacking intron 4 (I4) (FIG. 1a). Endogenous AFP mRNA and protein expression was detected in some investigated cancer cells lines including the liver cancer cell lines HepG2, PLC/PRF5, SNU495 and CL48 and non-liver cell line HEK293T. HepG2 cells were transfected with 500 ng tsRNA+500 ng AFP mini-gene, total cellular RNA was isolated 24 hours post transfection and both, levels of trans-spliced and cis-spliced RNA were quantified by real-time reverse transcriptase PCR (rtRT-PCR) using an AFP-specific TaqMan probe. Trans-splicing was additionally detected using an HSVtk-specific probe (FIG. 1b). Cis-splicing was found to be more prevalent than trans-splicing and the splice site mutants revealed reduced trans-splice activity compared with the parental constructs and the HSVtk or HHRz cleavage site-mutants. Sequencing of the splice junctions within the PCR-amplified cDNAs confirmed the accuracy of trans-splicing triggered by the parental constructs as well as cis-splicing both of the AFP mini-gene and the endogenous transcript (FIG. 1c). Competition between cis- and trans-splicing within or towards the AFP mini-gene transcript or the endogenous AFP pre-mRNA indicated that cis-splicing can be inhibited by trans-splicing (FIG. 1d,e). We could also detect successful trans-splicing towards the endogenous AFP pre-mRNA (FIG. 1f) and its accuracy was confirmed by cDNA sequencing (FIG. 1g). Trans-splicing triggered HSVtk protein expression was monitored by Western blot analyses and found to correlate well with the levels of trans-splice RNA (Supplementary FIG. 1d,e). No chimeric AFP-HSVtk fusion proteins were detectable with the 3'ER constructs pointing towards efficient P2A-proteolytic cleavage. In case of 5'ER, the splice site mutants triggered clearly reduced levels of HSVtk expression as compared with the parental construct indicating the vast majority of HSVtk protein originated from trans-splicing and not from leaking splicing-independent expression. After 3'ER only a 42 kDa HSVtk isoform was formed whereas 5'ER and the positive control lead to the expression of two, a 42 kDa and a 44 kDa, HSVtk isoforms.

Figure 2:
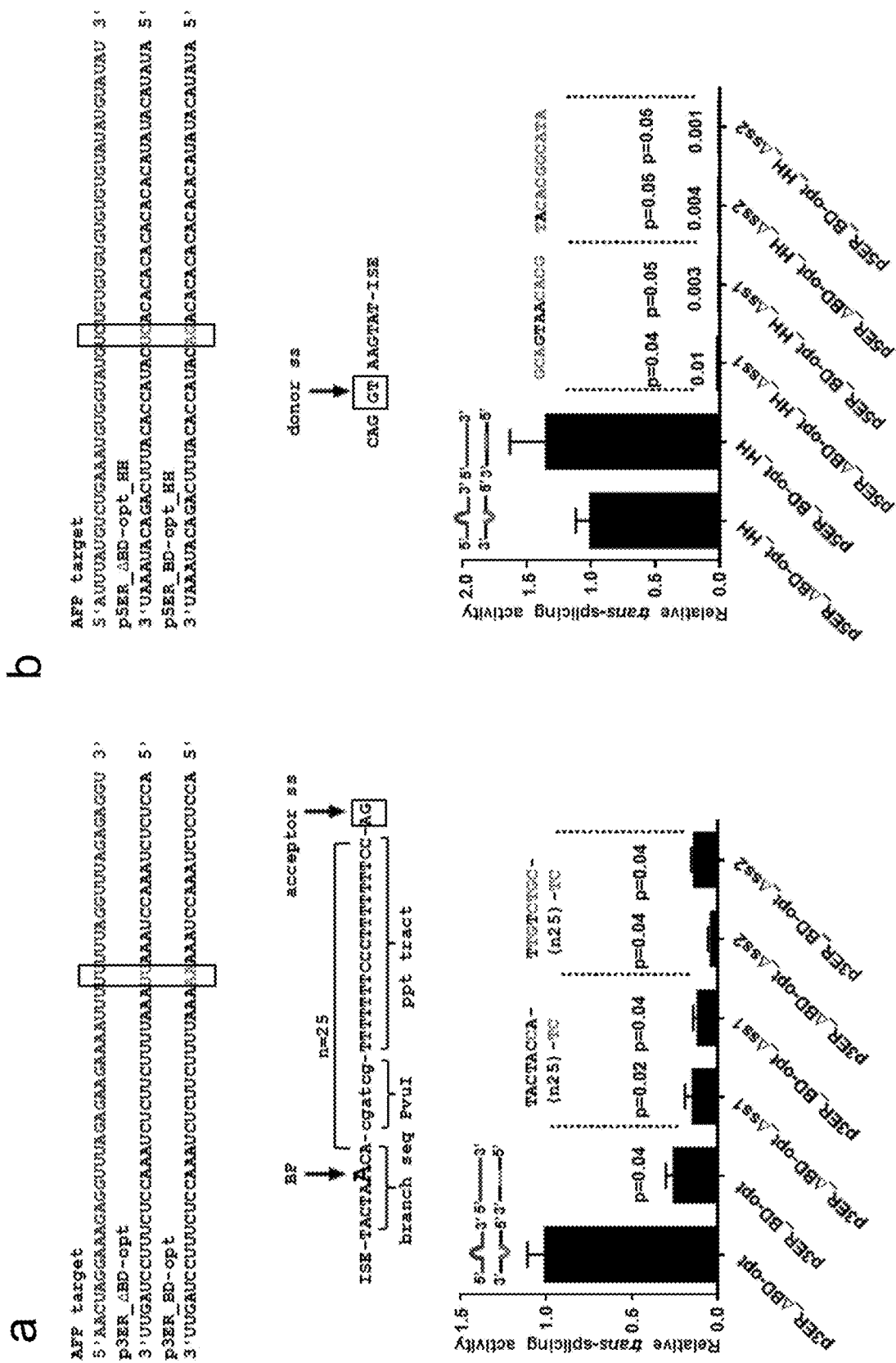
FIG. 2 Efficient trans-splicing molecules in terms of splice site activity, BD sequence selection and secondary structure. The BDs designed for (a) 3'ER SEQ ID NO. 128, SEQ ID NO. 129 and SEQ ID 130 (top left panel) and (b) 5'ER SEQ ID NO. 131, SEQ ID NO: 132 and SEQ ID 133 (top right panel) were 50 bases long with two target (top) mismatch ΔBD (middle) as compared to existing sequence design BD (middle) with full complementarity with target. Splice sites were mutated by changing the BP motif and 3' acceptor ss in Δss1 or further mutating the BP sequence in Δss2 for 3'ER (left panel) and for 5'ER (right panel) the 5' donor ss was kept intact by changing adjoining areas in Δss1 and further mutated by changing the donor site in Δss2. The relative trans-splicing activity of 3' ΔBD and 5' ΔBD active constructs were tested against the active no mismatch BD constructs and ss mutants with both ΔBD and BD sequence designs. RNA secondary structure prediction (mfold) of the (c) 3'ER SEQ ID NO. 134, SEQ ID NO. 135, SEQ ID NO. 136, SEQ ID NO. 137, SEQ ID NO: 138 and SEQ ID NO: 139 (left top panel) and (d) 5'ER SEQ ID NO. 140, SEQ ID NO. 141, SEQ ID NO. 142, SEQ ID NO. 143 and SEQ ID NO. 144 (right top panel) active BDs with or without target mismatch as compared to the computationally selected structured BD designs with two target mismatch middle) and 3'ER_BD-opt-inv SEQ ID NO: 139, 5'ER_BD-opt-inv_HH SEQ ID NO. 144 with both ΔBD and BD designs. The lower panel shows the relative trans-splicing activity between the improved BD designs of p3ER_ΔBD-opt SEQ ID NO. 134 (left) and p5ER_ΔBD-opt_HH SEQ ID NO. 143 (right) as compared to state-of-the-art existing BD designs with no computational analyses in terms of sequence and structure. n=3, mean±SEM, test for significance used was one-way.
Figure 2:
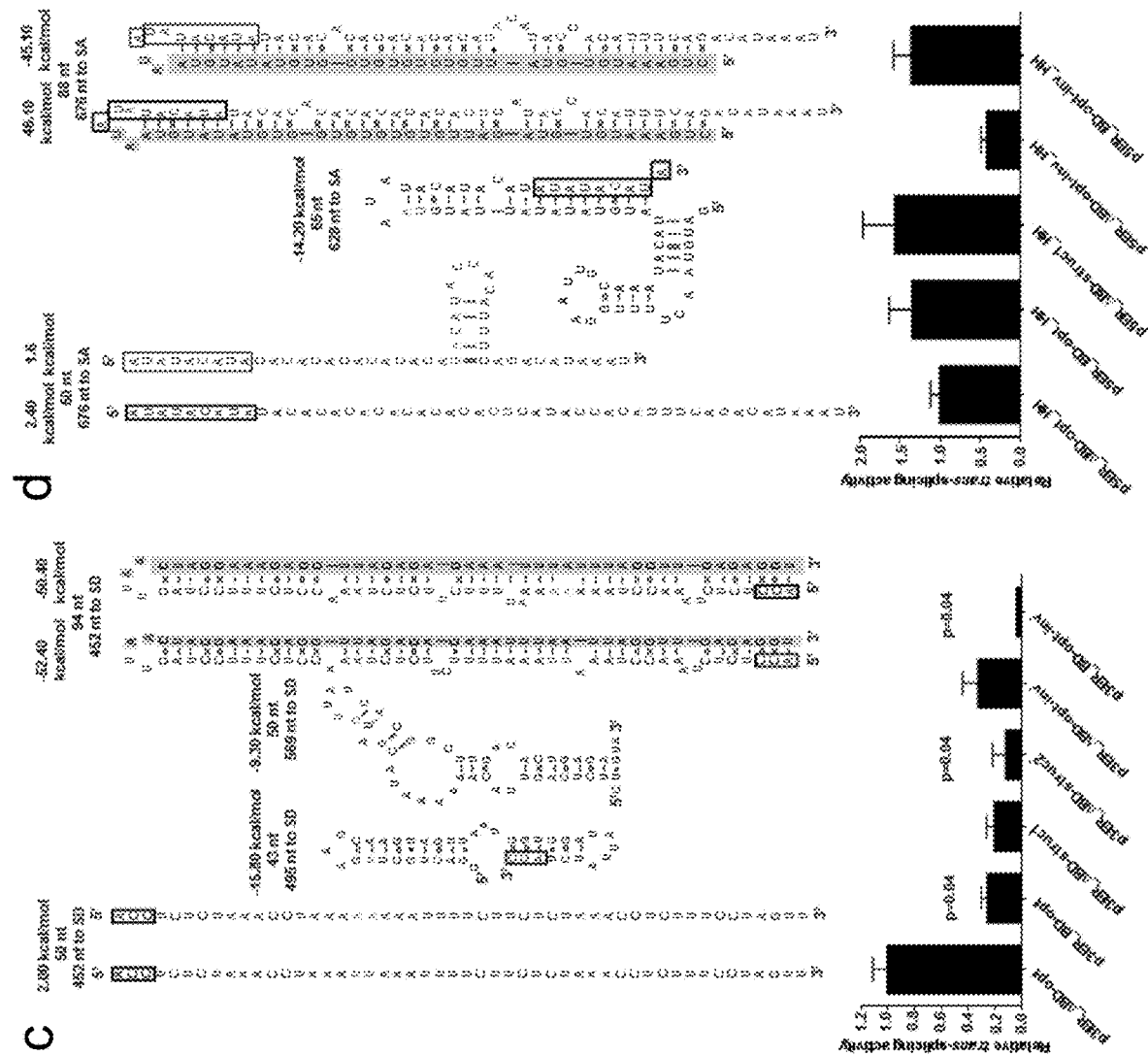

Design of Binding Domain Sequence and Structure Substantially Improves 3' but not 5' Exon Replacement We investigated the role of BD RNA secondary in RNA trans-splicing. Using our previously described software tool foldanalyse (Senger, et al. 1995) we identified the least structured BDs of about 50 nt in length that can be targeted against the AFP pre-mRNA: 3ER_BD-opt or 5ER_BD-opt for 3' or 5'ER which bind to intron 5 or intron 3, respectively (FIG. 2, Supplementary FIG. 1b, 2a). As controls we identified highly structured domains of comparable length (3ER_BD-struc1, 3ER_BD-struc2, and 5ER_BD-struc1)

(Supplementary FIGS. 1, 2) each one of them that overlapped with the unstructured domains. Finally we designed another two BDs, 3ER_BD-opt-inv and 5ER_BD-opt-inv, by employing internal inverted repeats fully encompassing the favourable BDs 3ER_BD-opt and 5ER_BD-opt turning them into structured unfavourable BDs but maintaining the distance to the target splice sites. Selected binding domains were fused to the other domains of the tsRNA via linker or spacer sequences that ensured the selected BD structures did not change upon fusion (Supplementary FIG. 1a). To suppress RNA editing, all these BDs were generated as imperfect target binding domains (ΔBD) harbouring central 2 nt target mismatches. To investigate the effect triggered by these mismatches, we also generated the fully complementary analogues 3ER_BD-opt and 5ER_BD-opt or 3ER_BD-opt-inv and 5ER_BD-opt-inv of the unstructured or the most structured BDs, respectively (FIG. 2a, 2b). All BDs and ΔBDs were cloned into the parental trans-splicing vectors. HepG2 cells were co-transfected with the trans-splicing plasmids and the AFP mini-gene vector and trans-splicing activities were monitored 24 hours post transfection. In the case of 3'ER, the tsRNA harbouring 3ER_ΔBD-opt triggered 4-fold (p=0.04), 3-fold, or 30-fold (p=0.04) stronger trans-splicing compared with its analogues harbouring 3ER_BD-opt, 3ER_ΔBD-opt-inv or 3ER_BD-opt-inv (FIG. 2c). In addition, 3ER_ΔBD-opt was 4- or 6-fold (p=0.04) more potent than 3ER_BD-struc1 or 3ER_BD-struc2. These data indicate that (i) mismatched ΔBDs are more potent than complementary BDs and (ii) unstructured BDs or ΔBDs are more efficient than structured ones. Conversely, the degree of RNA secondary structure formation and target complementarity within the binding domains did not impact 5'ER activities (FIG. 2d). Splice site mutants, however, impaired 3' and 5'ER activities of all constructs (FIG. 2a,b). 5' exon replacement correlates with the thermodynamic stability of the tsRNA 3' end.

FIG. 1b indicated that construct p5ER_ΔBD-opt_ΔHH harbouring the inactive HHRz cleavage motif triggered stronger trans-splice activities as compared with its cleavable analogue p5ER_ΔBD-opt_HH. That was surprising as the uncleaved RNA comprises a polyA tail and is expected to be exported to the cytoplasm thereby lowering its nuclear concentration and the rate of trans-splicing. We investigated HHRz cleavage by quantifying the cleaved RNA 3' end using stem-loop primer based rt-RT-PCR (FIG. 3a). This method was proven to efficiently discriminate between perfect primer-matching and extended RNA 3' ends. The observed 6.2 cycle difference indicated a ribozyme cleavage rate above 90% yielding trans-splicing RNA with an unstructured 3' terminal BD (FIG. 3a). Unstructured ends of antisense RNA have been reported to be associated with both fast target binding and degradation. To stabilize the 3' end of the trans-splicing RNA for 5'ER after ribozyme cleavage, we designed constructs harbouring a stem-loop (p5ER_ΔBD-opt_hp_HH) or Y-shaped (p5ER_ΔBD-opt_Y_HH) structure downstream of the BD but upstream of the HHRz cleavage site as well as a control in which the BD was followed by the polyA site but which was lacking the ribozyme and the spacer (p5ER_ΔBD-opt_HH(−)) (FIG. 3c). RNA secondary structures before and after ribozyme cleavage were predicted using mfold. The experimental investigation of all 5'ER constructs revealed a positive correlation between the thermodynamic stabilities of the RNA 3' ends, i.e. the Gibbs free energy ΔG of secondary structure formation, and the trans-splicing activities (FIG. 3d,e). Strongest trans-splicing was observed for the construct with the mutated HHRz cleavage site harbouring a stable secondary structure formed by the spacer and the SV40 polyA site, followed by the constructs with the terminal Y-shaped and stem-loop structures, and the parental construct with the 3' terminal BD. However, by far the lowest trans-splice activity was measured for the construct comprising the polyA site but lacking a stable structure at the 3' end.

Figure 4:
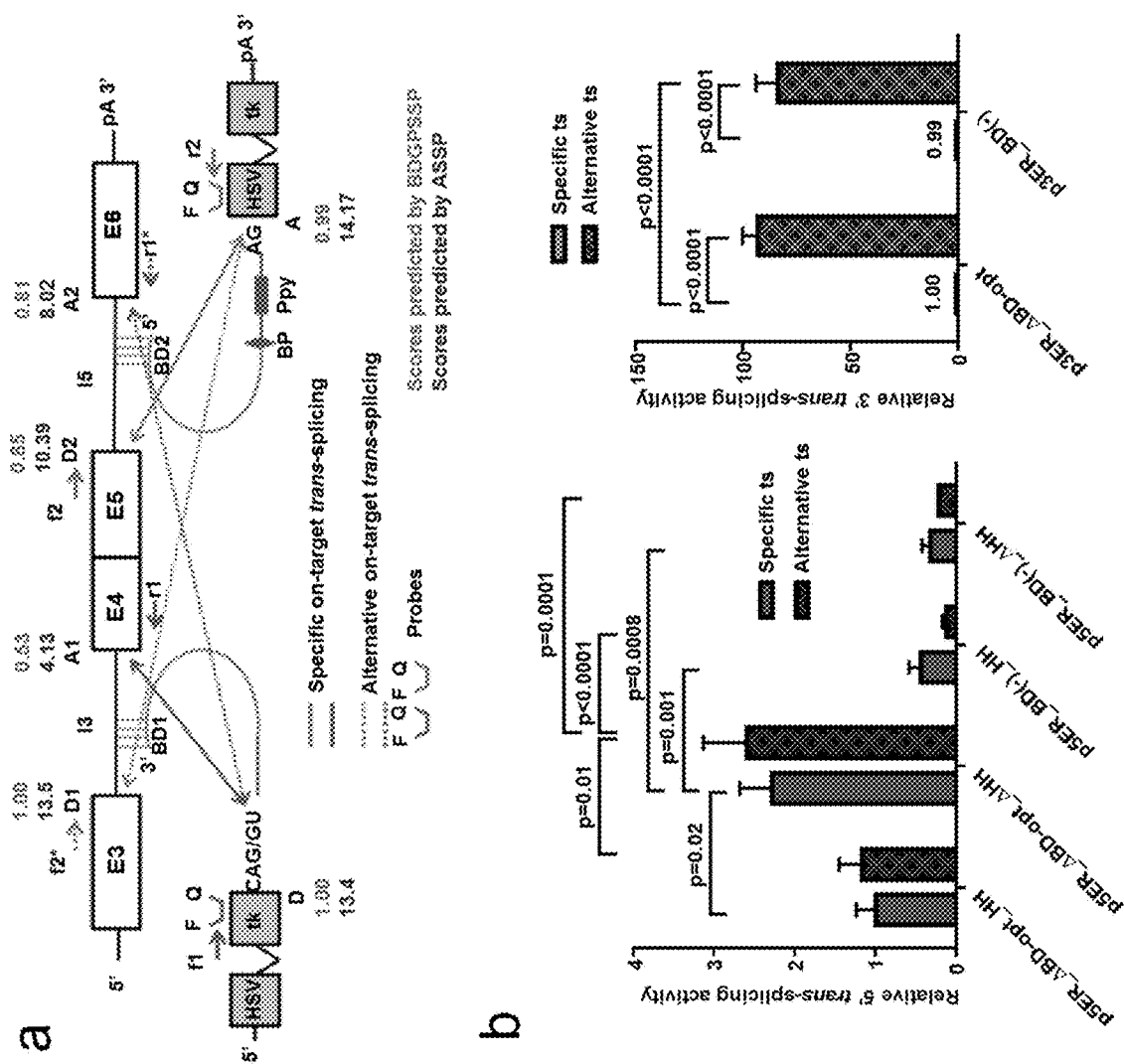
FIG. 4 Investigating the specific and alternative on-target trans-spicing of HSV-tk to the AFP gene. (a) Schematic showing the AFP target (AFP_E3-E6 mini-gene) along with the 5'ER and 3'ER events. Solid arrows show specific on-target trans-splicing and dashed arrows shows the alternative on-target trans-splicing events. Both these events were documented using TaqMan quantification with HSVtk probes. The numbers in red font denotes the strengths of the donor and acceptor splice sites using Splice Site Prediction algorithm. (b) Relative specific and alternative on-target trans-splicing activities of the parental p5ER construct (left) and p3ER construct (right) with its HH mutant (only for p5ER) and their no BD constructs. n=3, mean±SEM, test for significance used was two-way ANOVA with Bonferroni post-hoc (c) Schematic showing the design of additional BDs along with the original 3'ER ΔBD (BD) to reduce the occurrence of alternative on-target trans-splicing in 3'ER constructs. BD E SEQ ID NO. 146 (top) binds 46 bases downstream of the 5' ss of exon 5, BD F SEQ ID NO. 147 (middle) binds to the 5' ss of exon 3 and BD D SEQ ID NO. 148 (bottom) binds to the Ppy tract of the p3ER trans-splicing molecule. (d) Relative specific and alternative on-target trans-splicing activity of the parental p3ER with single ΔBD as compared to additional BDs designed to complement the original ΔBD. The specificity factor of each construct was determined as (specific ts/alternative ts)× 100%. n=3, mean±SEM, test for significance used was two-way ANOVA with Tukey post-hoc (e) Schematic showing the construct with no BD and additional BD D to prevent trans-splicing without specificity of binding domain.
Figure 4:
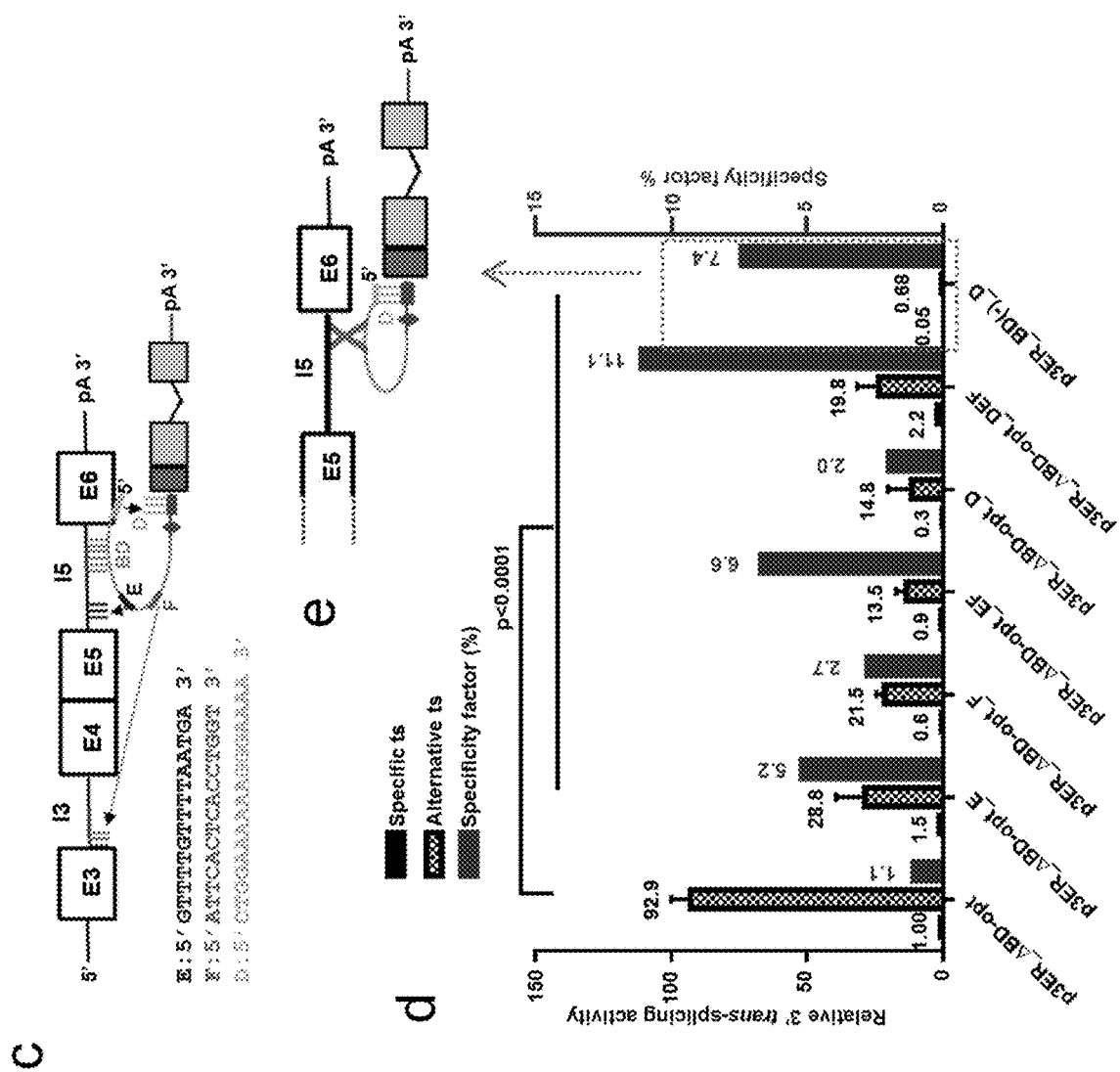

Multiple Binding Domains Enhance Targeted Trans-Splicing and Suppress Alternative On-Target Trans-Splicing Thereby Increasing the Specificity of 3'ER To suppress alternative on-target trans-splicing and to improve the trans-splicing specificity we designed novel RNAs for 3'ER which harbor multiple target and/or self-binding domains (FIG. 4c). Complementary to BD-opt which has been optimized for fast target binding, we implemented (i) BD-E to bring the intended trans-splice sites D2 and A closer to each other, (ii) BD-F to bind and functionally block the alternative donor splice site D1, and (iii) self-binding domain BD-D which was positioned directly upstream of BD-opt to shield the PPT of acceptor splice site A of the trans-splicing RNA in the absence of target binding. In addition we generated constructs with multiple BDs, p3ER_ΔBD-opt_EF or p3ER_ΔBD-opt_DEF, harbouring BDs E and F or BDs D, E, and F in addition to BD-opt, respectively. For all constructs we measured the relative activities of specific (TSspec) and alternative on-target trans-splicing (TSalt) and calculated a specificity factor S using equation (1) (FIG. 4d):

$$S = TSspec/TSalt * 100\% \quad (1)$$

All secondary BDs increased the specificity of trans-splicing as reflected by an increase in the specificity factor. While BD-F and more pronounced BD-D suppressed both specific and alternative on-target trans-splicing, BD-E and the combination of BD-E and -F enhanced specific but suppressed alternative on-target trans-splicing. Most successful, however, was the combination of all three additional BDs D, E, and F which enhanced specific trans-splicing about 2-fold and reduced alternative splicing about 5-fold thus exhibiting a 10-fold higher specificity of trans-splicing as compared with the parental construct. In the construct without any target binding domain, internal BD-D suppressed trans-splicing towards the strong splice donor D1 or the moderately strong donor D2 20-fold or 130-fold presuming trans-splicing to any other cellular off-targets was suppressed to a similar extent. Notably, a comparable reduction of trans-splicing was observed in BD(−) constructs harbouring splice sites that were weakened by mutagenesis.

Figure 3:
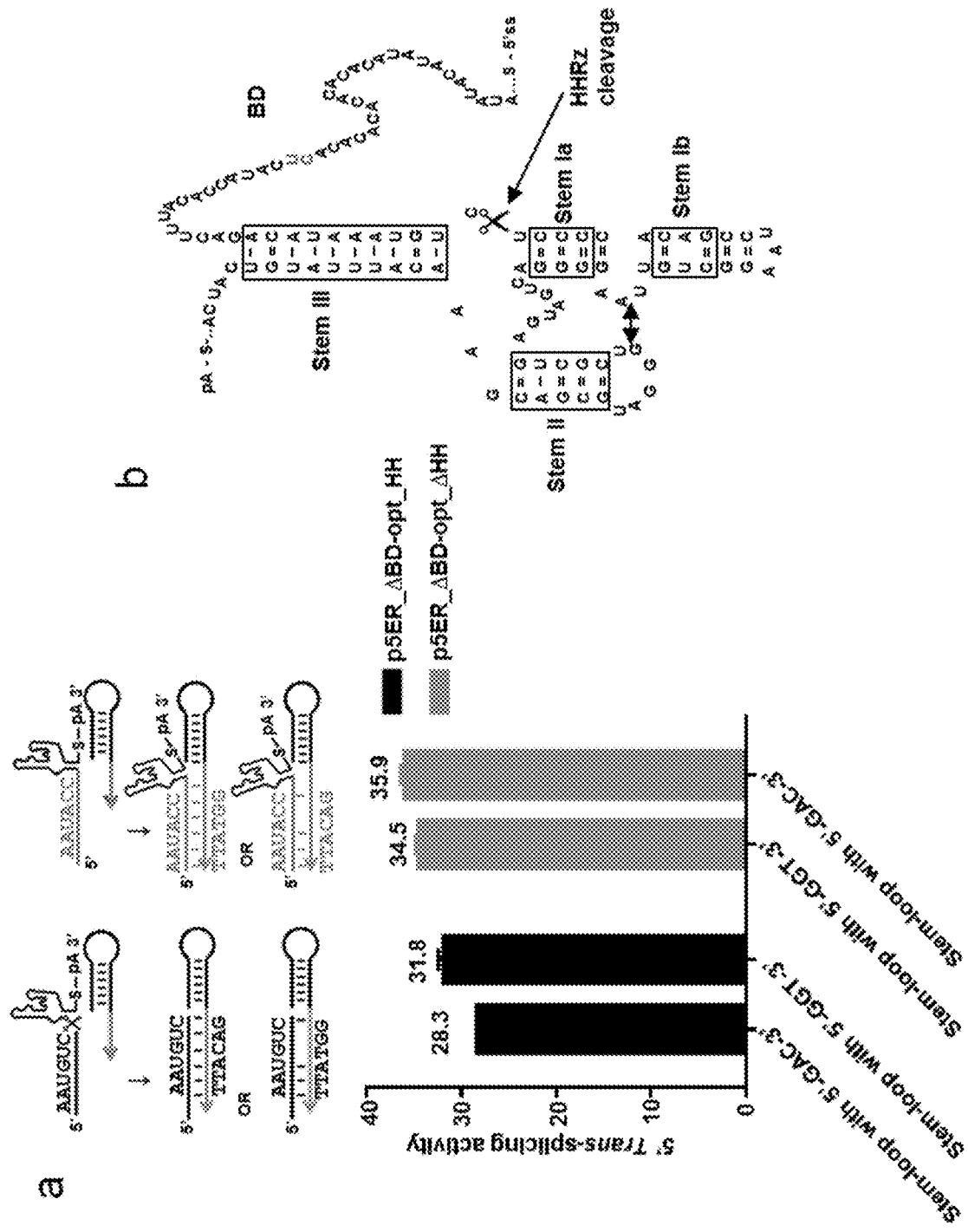
FIG. 3 Improved stability at 3' end of the RNA improves 5' trans-splicing in correlation with cleavage of hammerhead ribozyme. (a) Detection of cleavage efficiency of HH Rz with active GUC motif as compared to inactive ACC motif using specific stem loop primers, forward primers and a universal TaqMan probe and reverse primer. n=3, mean±SEM (b) RNA secondary structure prediction (mfold) of the tertiary motifs trans-cleaving HH Rz attached to the ΔBD at the 5' end and polyA at 3' end of the 5' trans-splicing construct SEQ ID NO. 145. The conserved motifs of stem Ia, Ib and II are highlighted in boxes and stem Ill is designed as a perfect complement to the 3' end of the ΔBD to make the HH Rz structure. Cleavage motif GUC is shown with a scissor icon. (c) Schematic representation of designed 5' trans-splicing constructs with modified 3' end of the trans-splicing RNA with various extents of RNA secondary structures after the BD at the 3' end followed by either an active cleavable HH Rz or inactive non-cleavable HH Rz motif or no HH Rz structure. (d) Relative trans-splice activity of parental p5ER_ΔBD_HH harboring an active HH Rz (black) as compared to the modified 3' end RNA trans-splicing constructs. n=3, mean±SEM, test for significance used was one-way ANOVA with Tukey post-hoc (e) Correlation between trans-splicing activities and total folding energy (ΔG) of the 5' constructs harboring active/inactive/no HH RZ capable/not capable of self and polyA cleaving. $R^2$, correlation coefficient. n=3, linear regression analysis.
Figure 3:
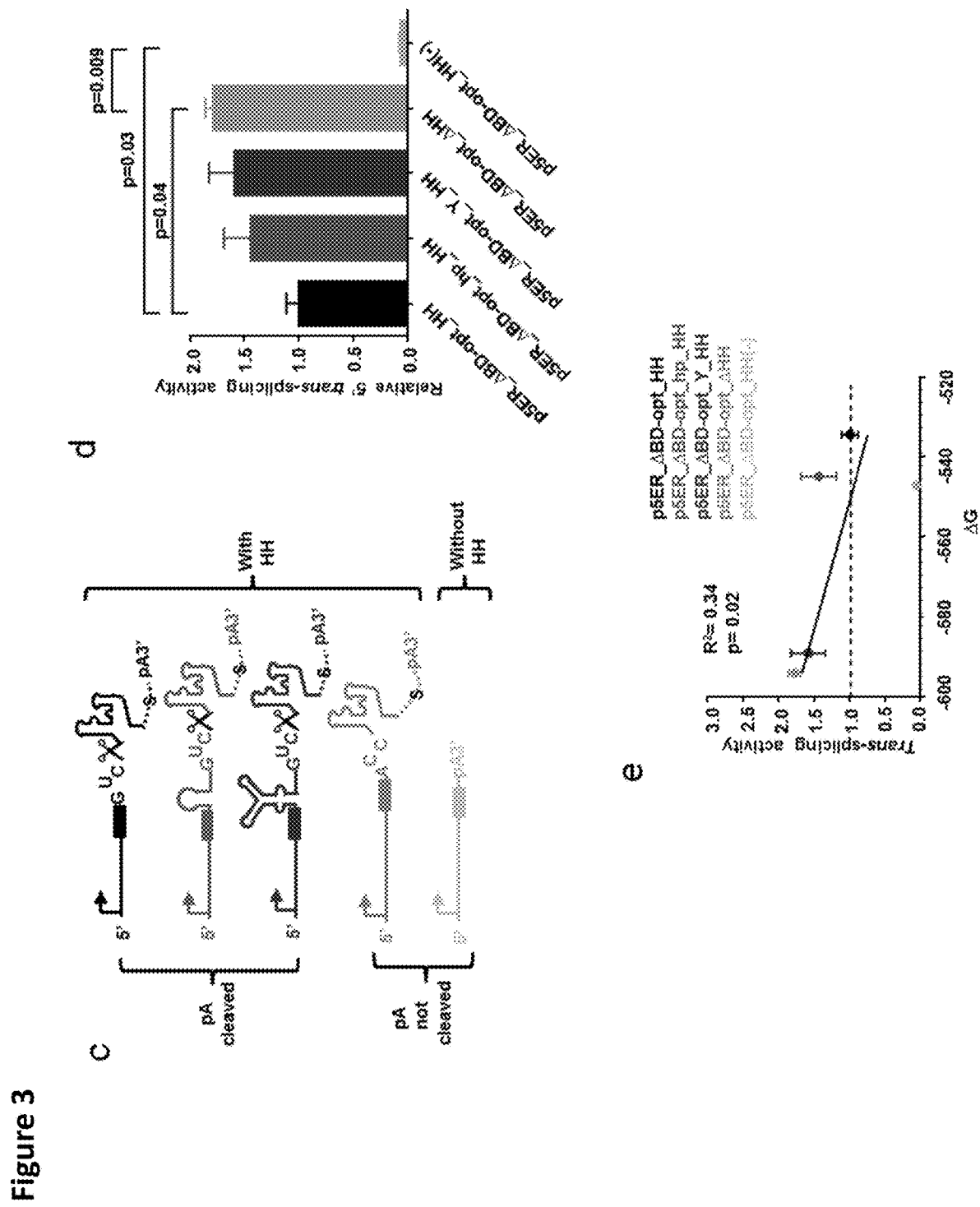
Figure 5:
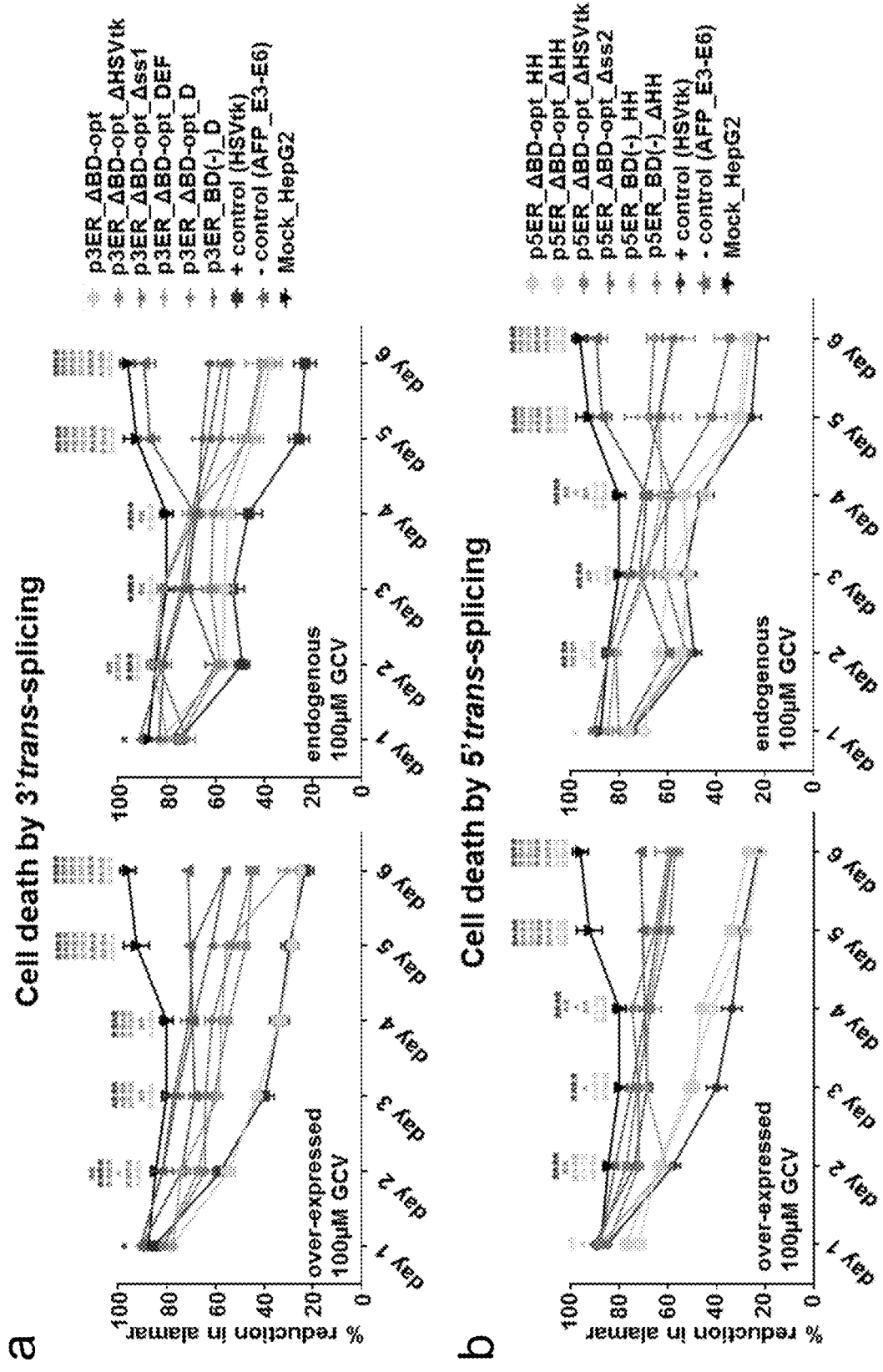
FIG. 5 Selective killing of HSVtk positive cells upon successful trans-splicing with either over-expressed or endogenous AFP target. Alamar Blue cell viability assay performed on selected (a) 3'ER constructs and (b) 5'ER constructs at over-expressed AFP (left) and endogenous AFP (right) with 100 µM dosage of GCV for a span of 6 days. (c) Cloning design of the control and trans-splicing single plasmid system in pVAX1 harboring both the trans-splicing gene and GFP gene used for analyses of apoptosis in flow cytometry. (d) Representative flow cytometry data images showing the gating strategy to detect Annexin V positive early and late apoptotic cells post trans-splicing. The sample shown is the positive HSVtk_GFP control treated either with 100 µM GCV or no drug. (e) Apoptosis detected in selected 3'ER and 5'ER constructs post 48 hours 100 µM GCV treatment at both over-expressed and endogenous AFP target levels. n=3, mean±SEM, test for significance used was two-way ANOVA with Tukey post-hoc. Besides mentioned significance in the figure, all samples except p3ER_ΔBD_Δss1_GFP were significant (p=0.0008 to <0.0001) compared to negative control AFP_E3-E6_GFP in over-expressed target set. All samples were significant (p=0.04 to <0.0001) compared to positive HSVtk_GFP control in endogenous target set. (f) Single cell gel electrophoresis performed to detect DNA damage at individual HepG2 cells 24 hours post 100 µM GCV treatment. Selected constructs were analyzed for 150 comets and documented as tail moment with/without GCV administration. The right panel shows a representative comet image taken at 10× magnification. Comets that fall above Q3+1.5 (IQR) are shown as dots (outliers). n=3, mean±SEM, test for significance used was one-way ANOVA with Tukey post-hoc. (g) Multiplexing trans-splicing technology in 3'ER with double BDs to target more than one HCC marker, including HCCA2, CD24 and VEGF along with AFP. The schematic shows the arrangement of BD1 and BD2 to target intron 5 of AFP target and introns 1 of the additional targets simultaneously. (h) Alamar Blue cell viability assay shows the effect of trans-splicing triggered cell death in constructs with two BDs as compared to single BD system when treated with a lower dose of 10 µM GCV at the endogenous context of the targets. (a) (b) (h) n=3, mean±SEM, test for significance used was two-way ANOVA with Bonferroni post-hoc compared to mock_HepG2. *p<0.05,  p<0.01, * p<0.001 and **** p<0.0001.
Figure 5:
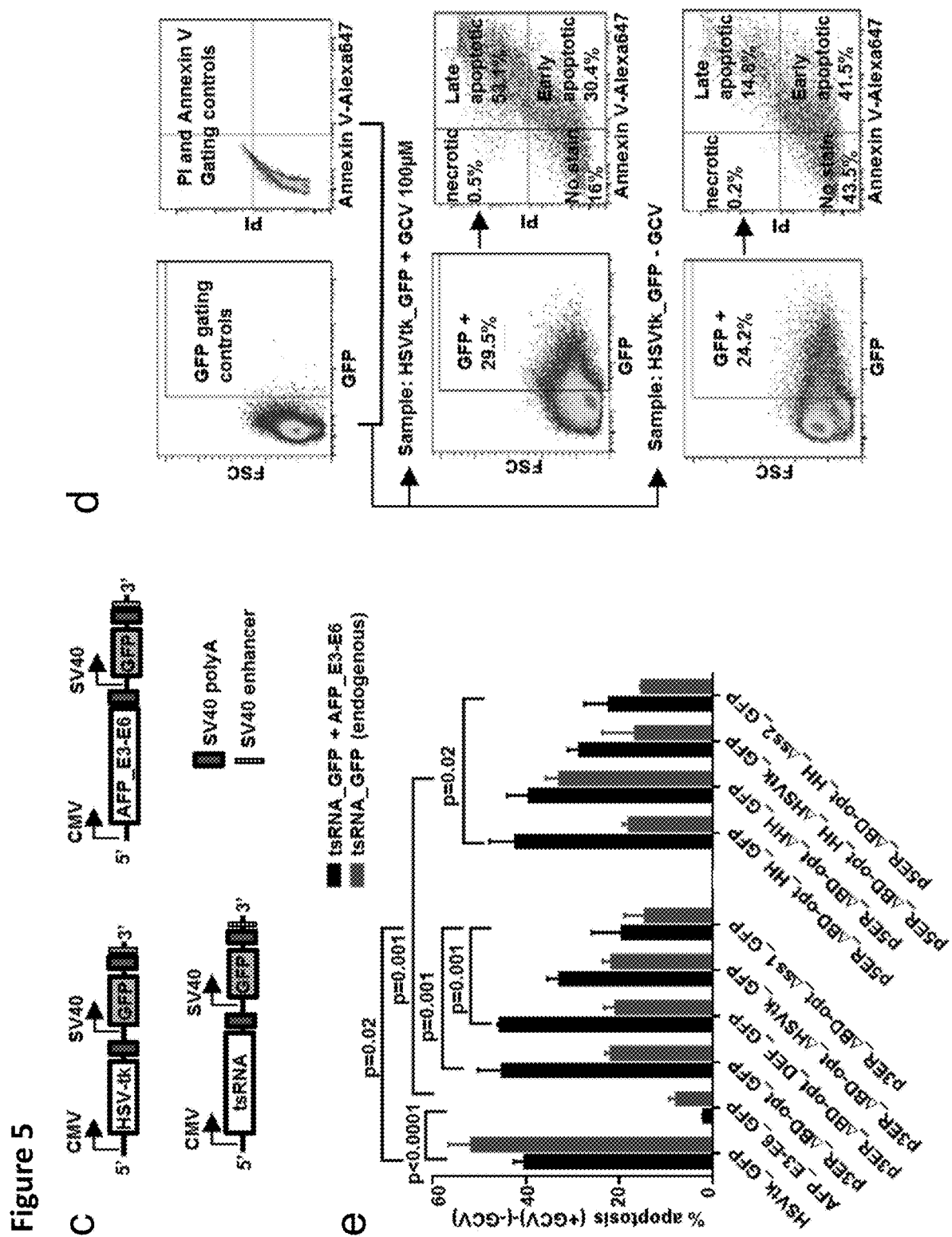
Figure 5:
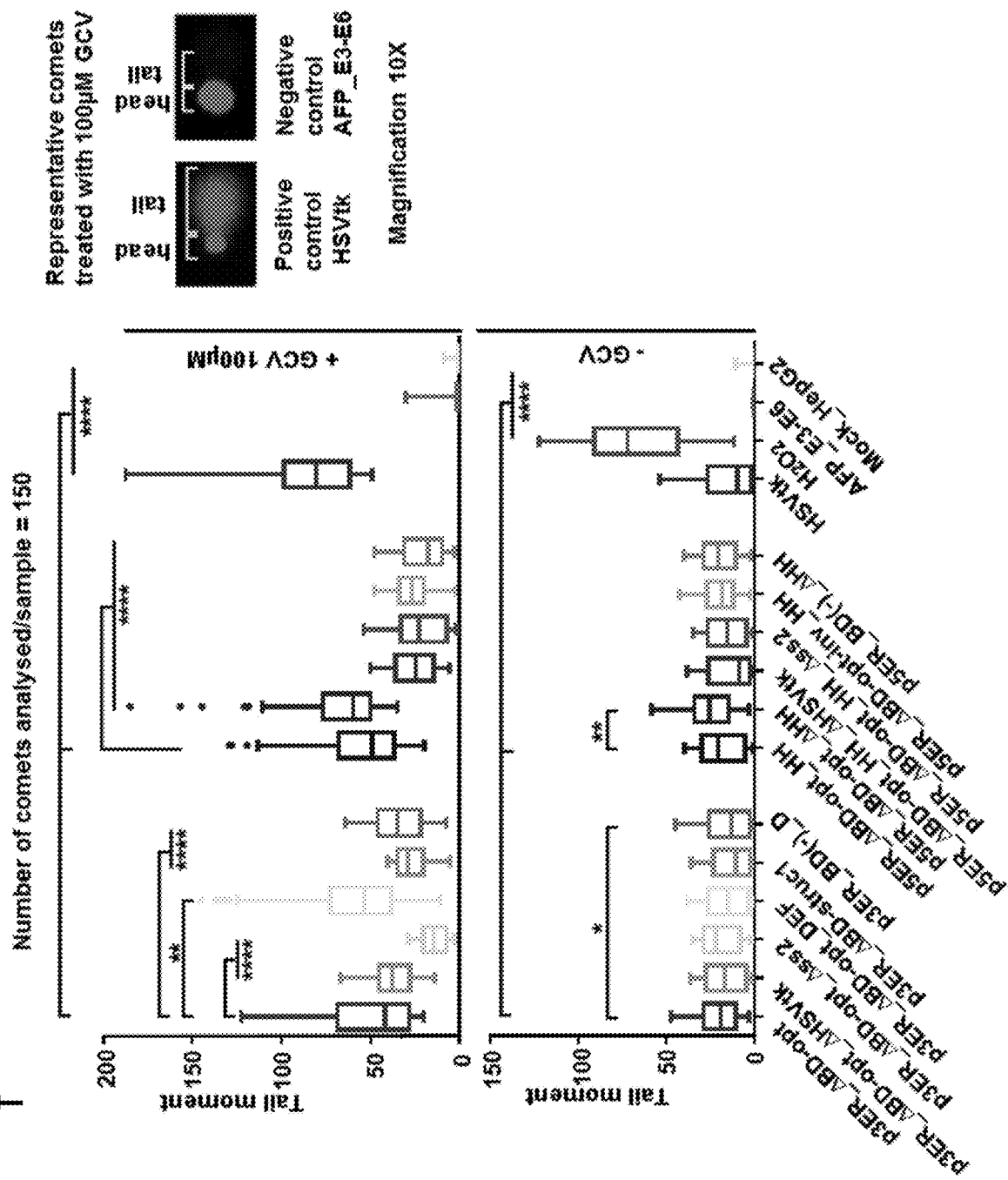
Figure 5:
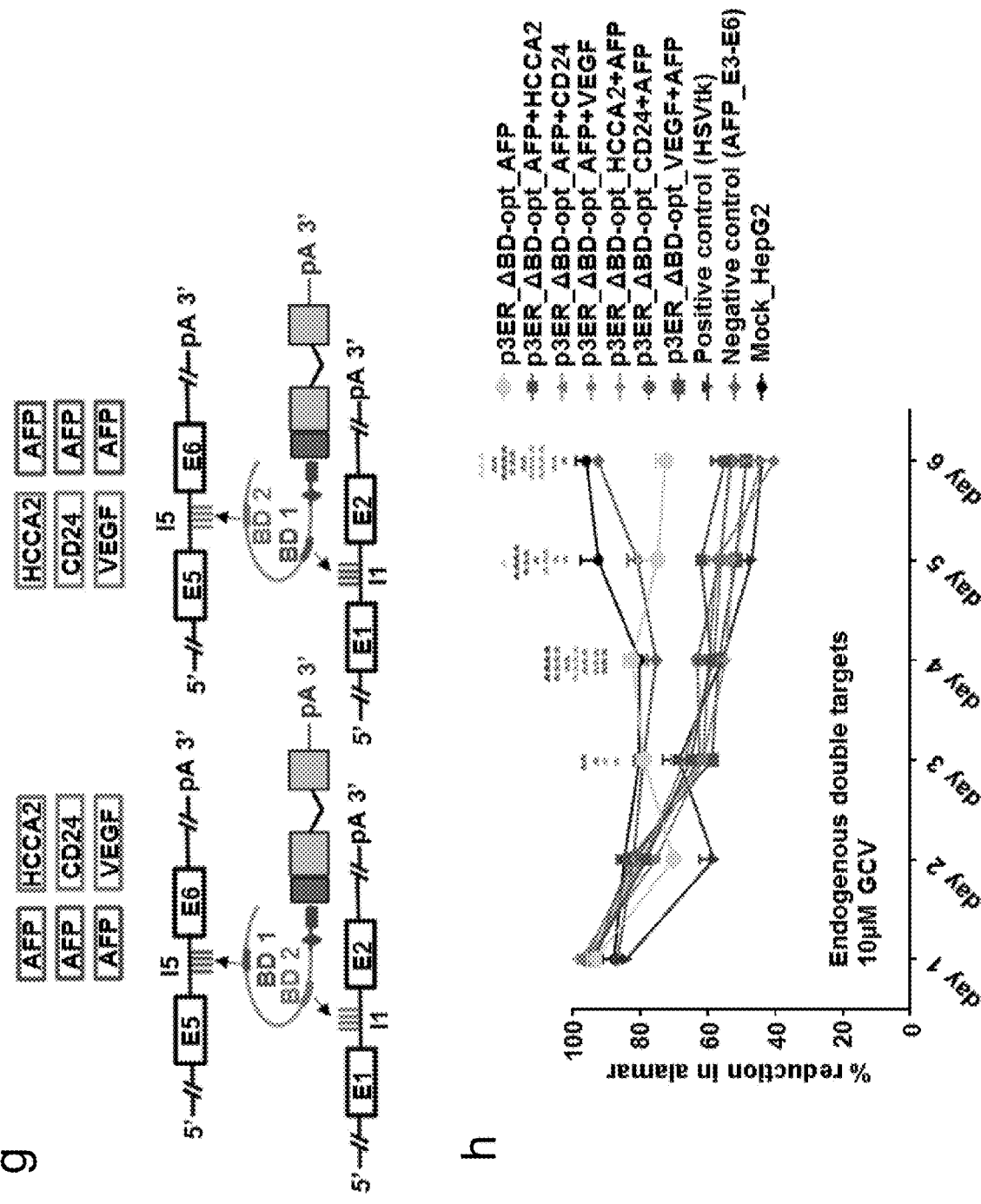
Figure 8:
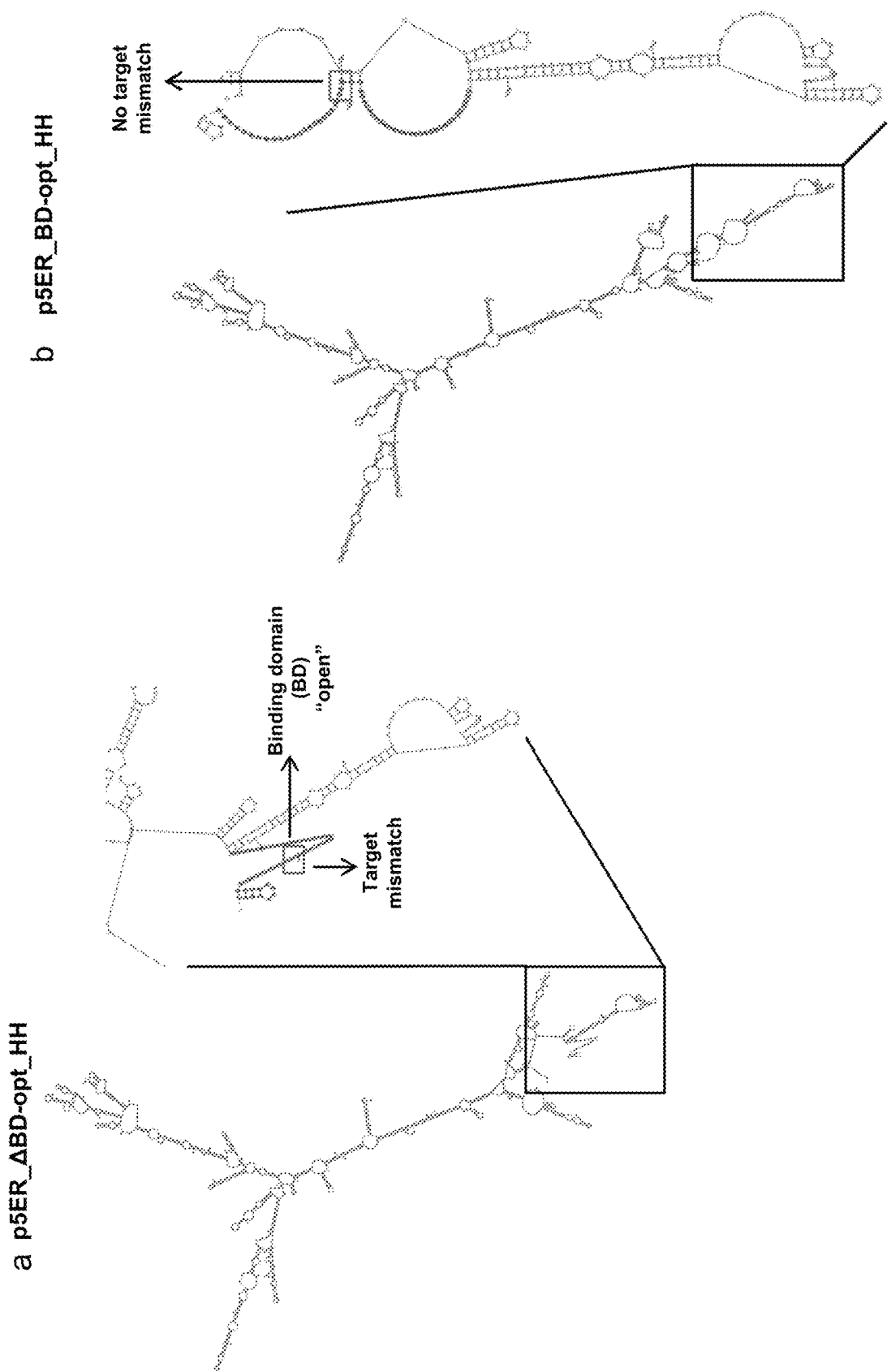
FIG. 8 RNA secondary structures showing the BDs of 5'ER constructs. (a) Parental 5'ER construct with optimized and unstructured BD designed with two mismatches with target (highlighted in box). (b) Parental 5'ER construct with optimized and unstructured BD designed with no mismatch with target (highlighted in box). (c) p5ER_ΔBD-struc1_HH (overlapping 9 bases with unstructured 5'ER_ΔBD-opt_HH) shows closed BD less suitable for optimum binding. (d) (e) p5ER_opt-inv_HH constructs with either (d) ΔBD or (e) BD with spacer as reverse complement to the parental BD for stem-loop structure formation with reduced trans-splicing.
Figure 8:
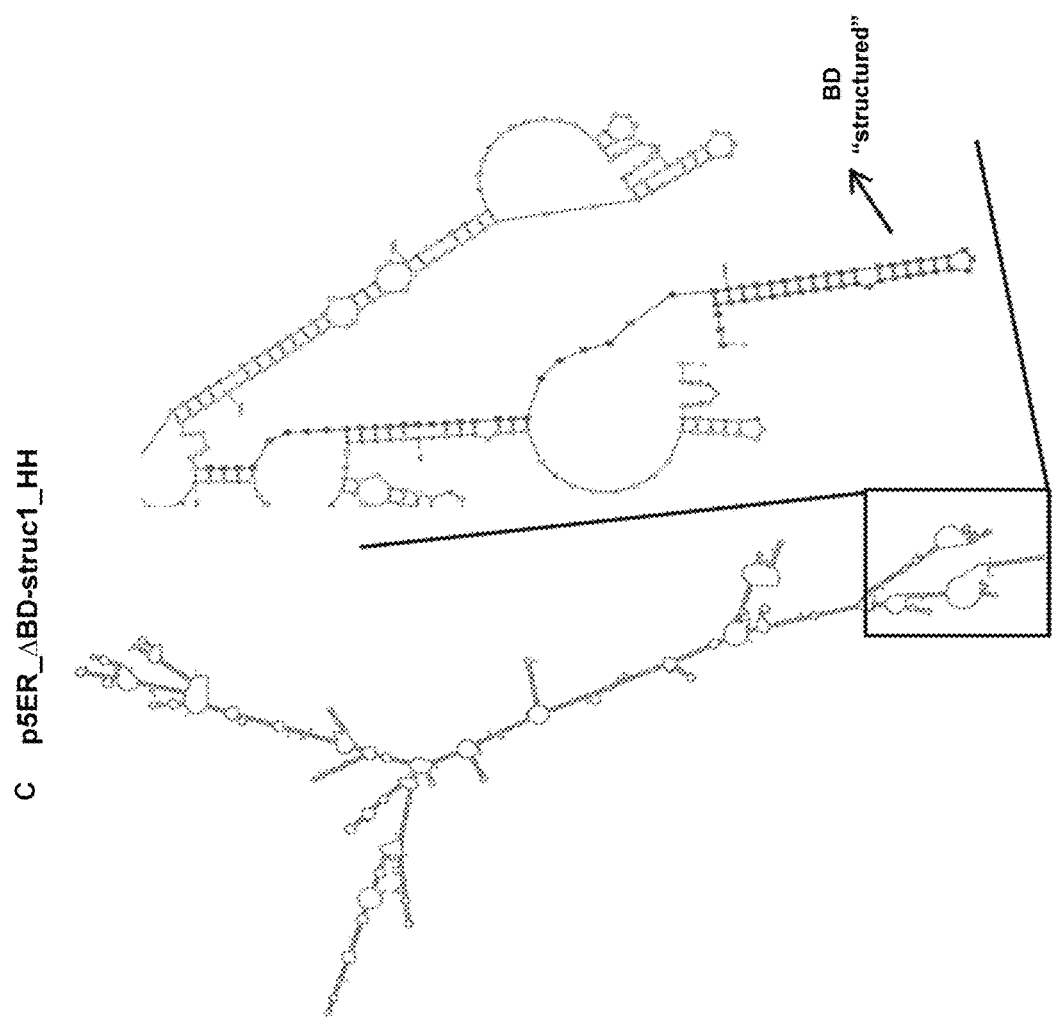
Figure 8:
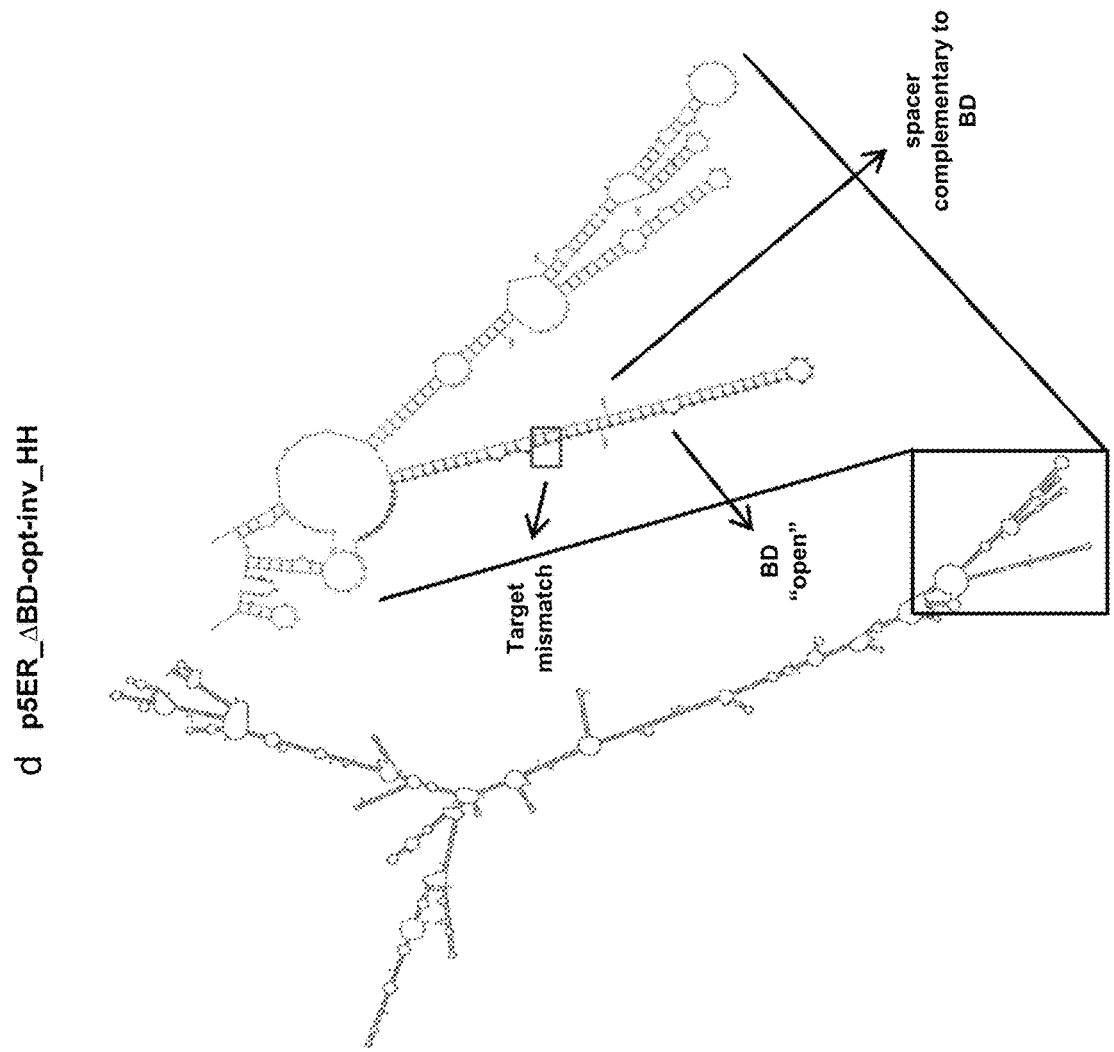
Figure 8:
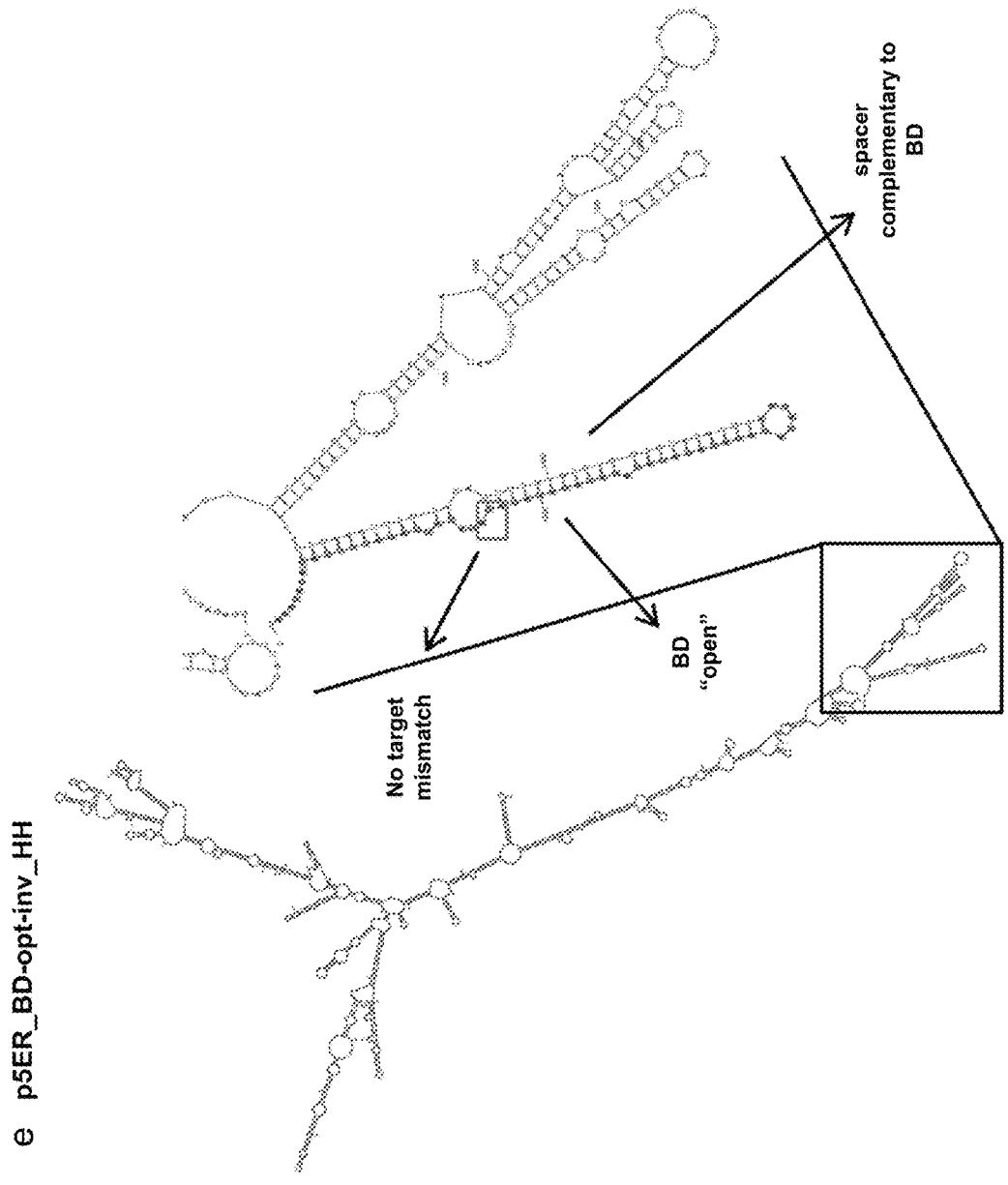
Figure 9:
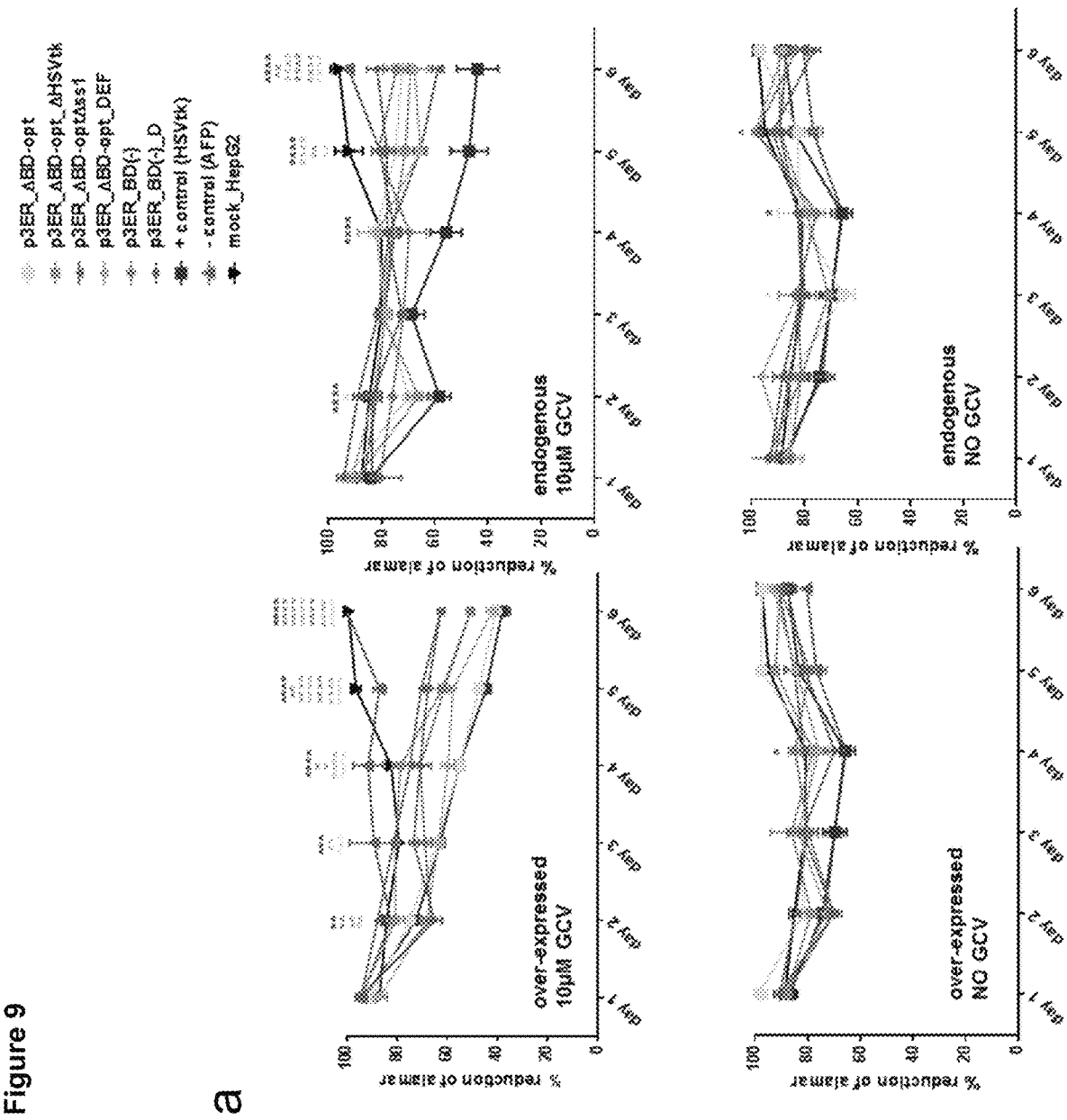
FIG. 9 Selective killing of HSVtk positive cells upon successful trans-splicing with either over-expressed or endogenous AFP target. Alamar Blue cell viability assay performed on selected (a) 3'ER constructs and (b) 5'ER constructs at over-expressed AFP (top left) and endogenous AFP (top right) with 10 µM dosage of GCV for a span of 6 days. No drug controls were tested in all constructs for both over-expressed (bottom left) and endogenous (bottom right) AFP levels. Significance calculated with respect to mock_HepG2.
Figure 9:
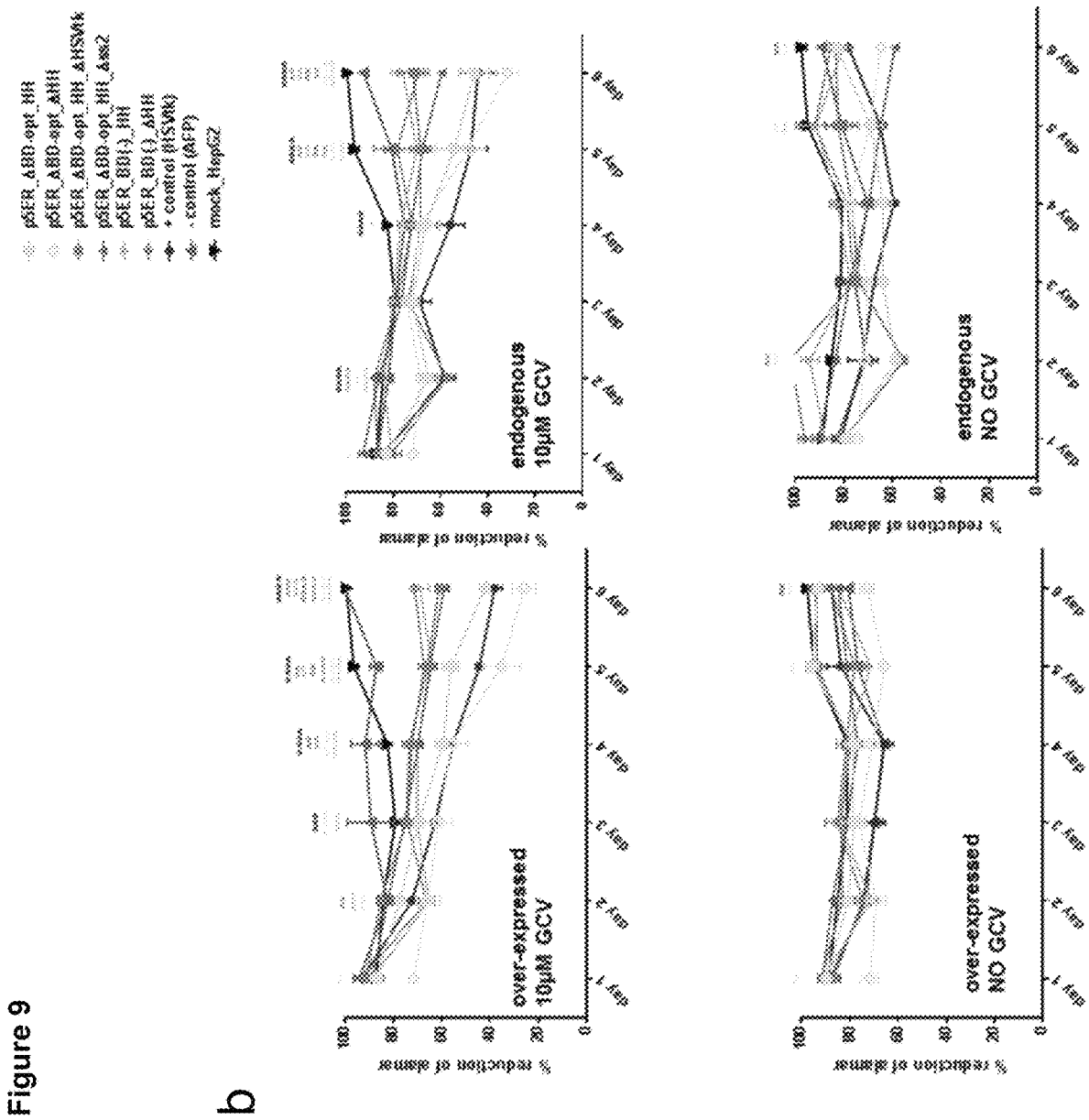
Figure 10:
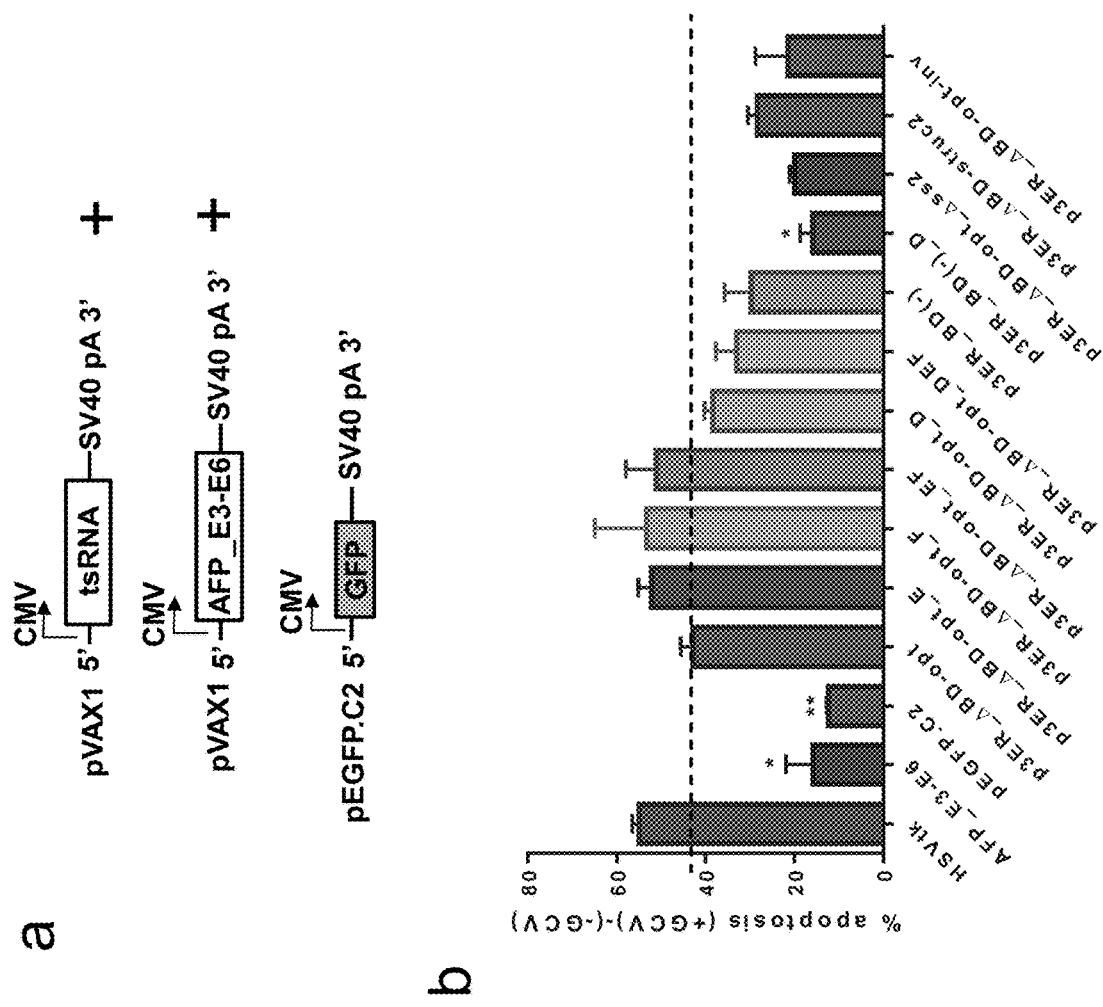
FIG. 10 Flow Cytometry analyses showing trans-splicing triggered apoptosis (a) Schematic diagram of the vectors harbouring the AFP mini gene, tsRNA constructs in pVAX1 plasmid and GFP gene in pEGFP.C2 plasmid for co-transfection in HepG2 cells to analyse cell death in FACS. Trans-splicing triggered apoptosis 48 hours post 100 µM dosage of GCV in selected (b) 3'ER and (c) 5'ER constructs. The negative AFP mini-gene, GFP controls and positive HSVtk control were co-transfected with equal amounts of pSUPER empty plasmid instead of the active ts plasmids. Significance calculated with respect to (b) p3ER_ΔBD-opt and (c) p5ER_ΔBD-opt_HH parental constructs. (d) Representative flow cytometry data images showing the gating strategy to distinguish between Annexin V positive apoptotic cells and GFP positive cells post trans-splicing. The sample shown is the positive HSVtk control treated either with 100 μM GCV or no drug. Co-transfection of tsRNA and eGFP plasmid shows differential populations of single positive cells, thus concluding co-transfection to be a non-optimal choice for selecting transfection positive cells undergoing trans-splicing triggered cell death.
Figure 10:
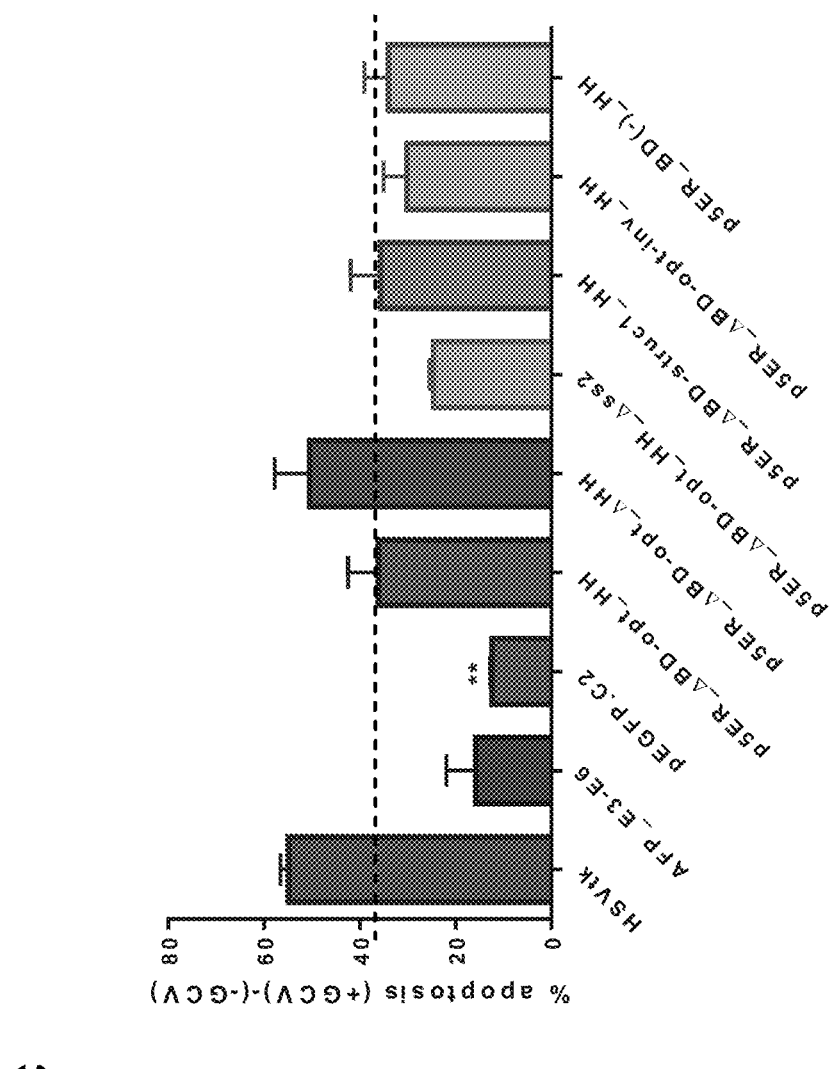
Figure 10:
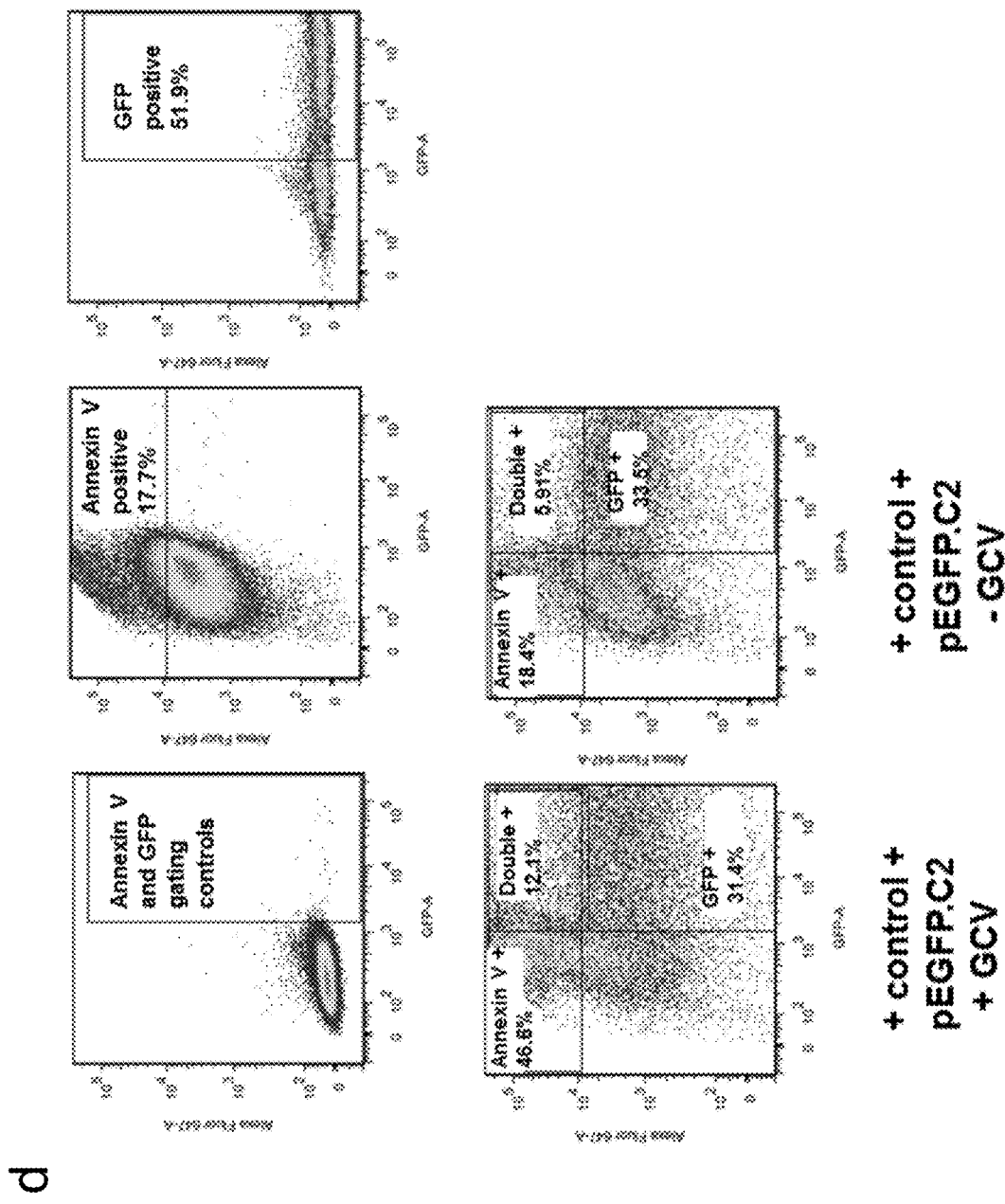
Figure 11:
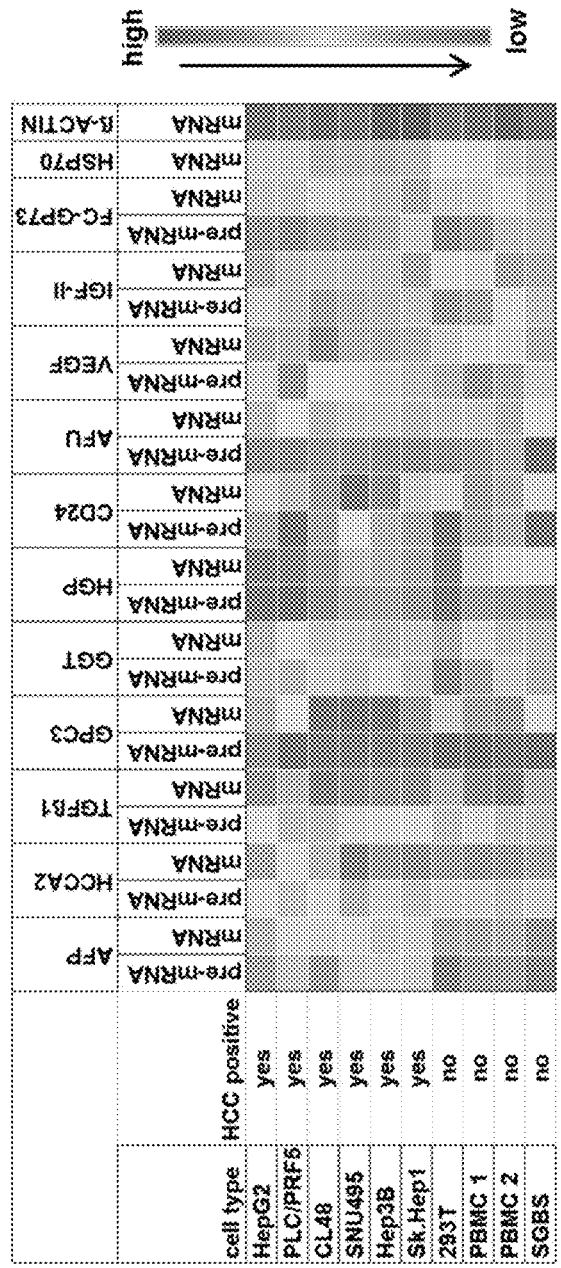
FIG. 11 Trans-splicing with double targets at endogenous levels (a) Heat map showing the pre-mRNA and mRNA expression levels of HCC marker genes in various cell types including transformed cell HCC positive and negative cell lines, peripheral blood mononuclear cells (PBMCs) and primary adipocyte negative for HCC. (b) Alamar assay to show trans-splicing with double targets at endogenous gene levels in 3'ER with 100 μM dosage of GCV (left) and no GCV (right).
Figure 11:
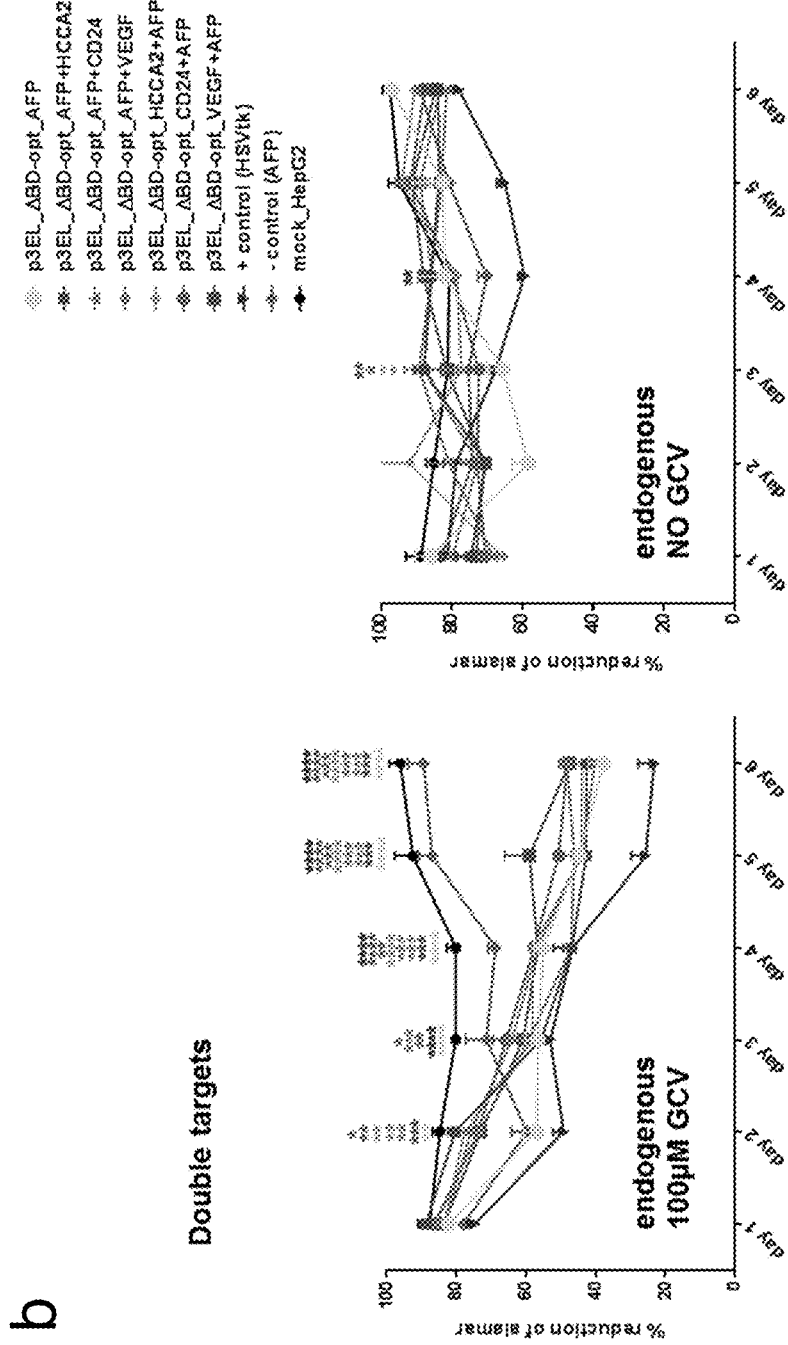
Figure 12:
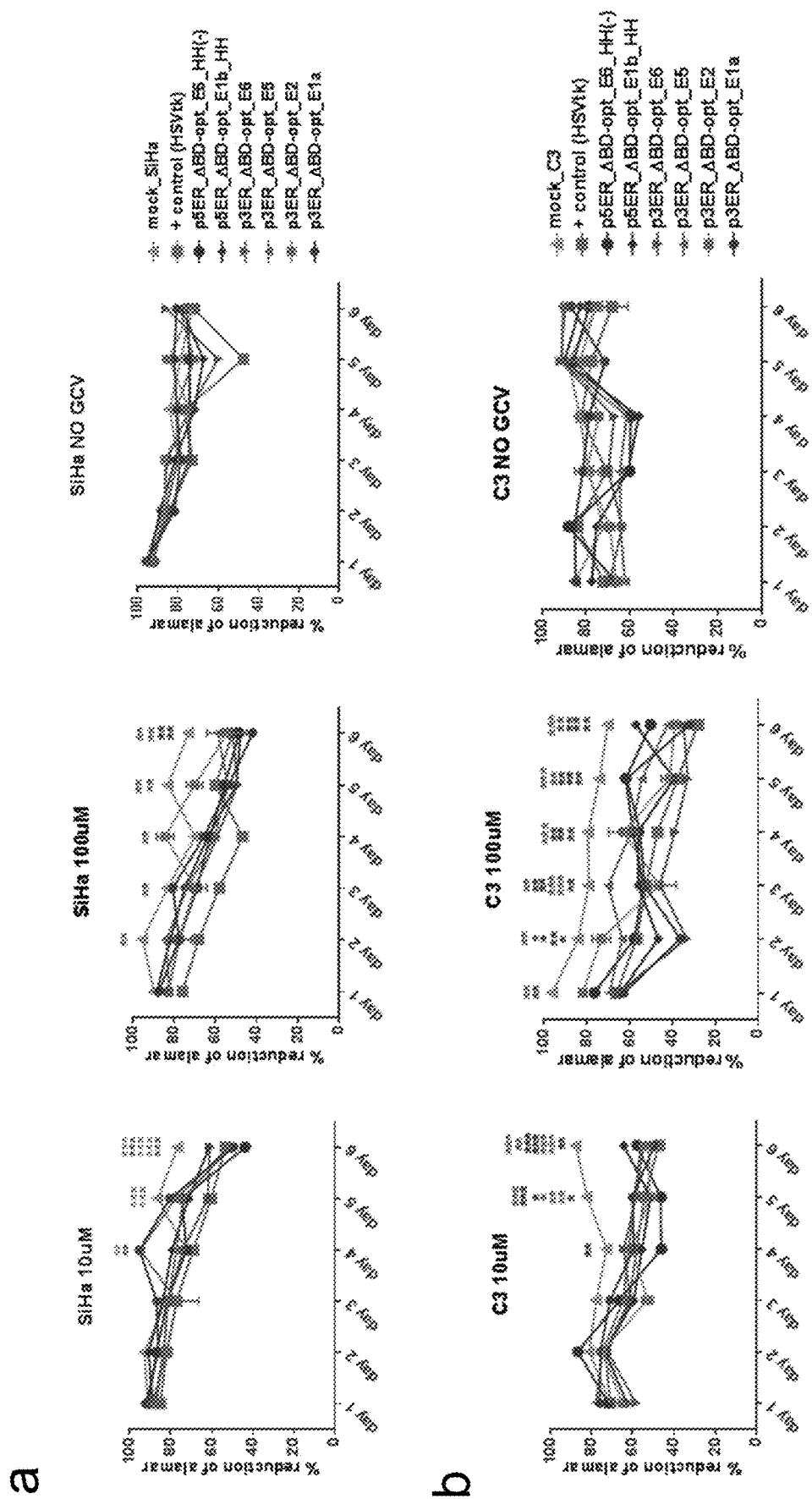
FIG. 12 Alamar blue assay showing the HSVtk triggered cell death in HPV16 positive and negative cell lines when treated with 10 μM, 100 μM or no GCV. Two 5'ER tsRNA constructs targeting E1b and E6 and four 3'ER tsRNA constructs targeting E1a, E2, E5 and E6 were tested in cell lines (a) HPV16 positive human cell line SiHa, (b) HPV16 positive mouse cell line C3, (c) HPV18 positive human cell line HeLa, (d) HPV16 and 18 negative human cell line HepG2 for GCV induced cell death for a span of 6 days with regular replenished dosage of drug.
Figure 12:
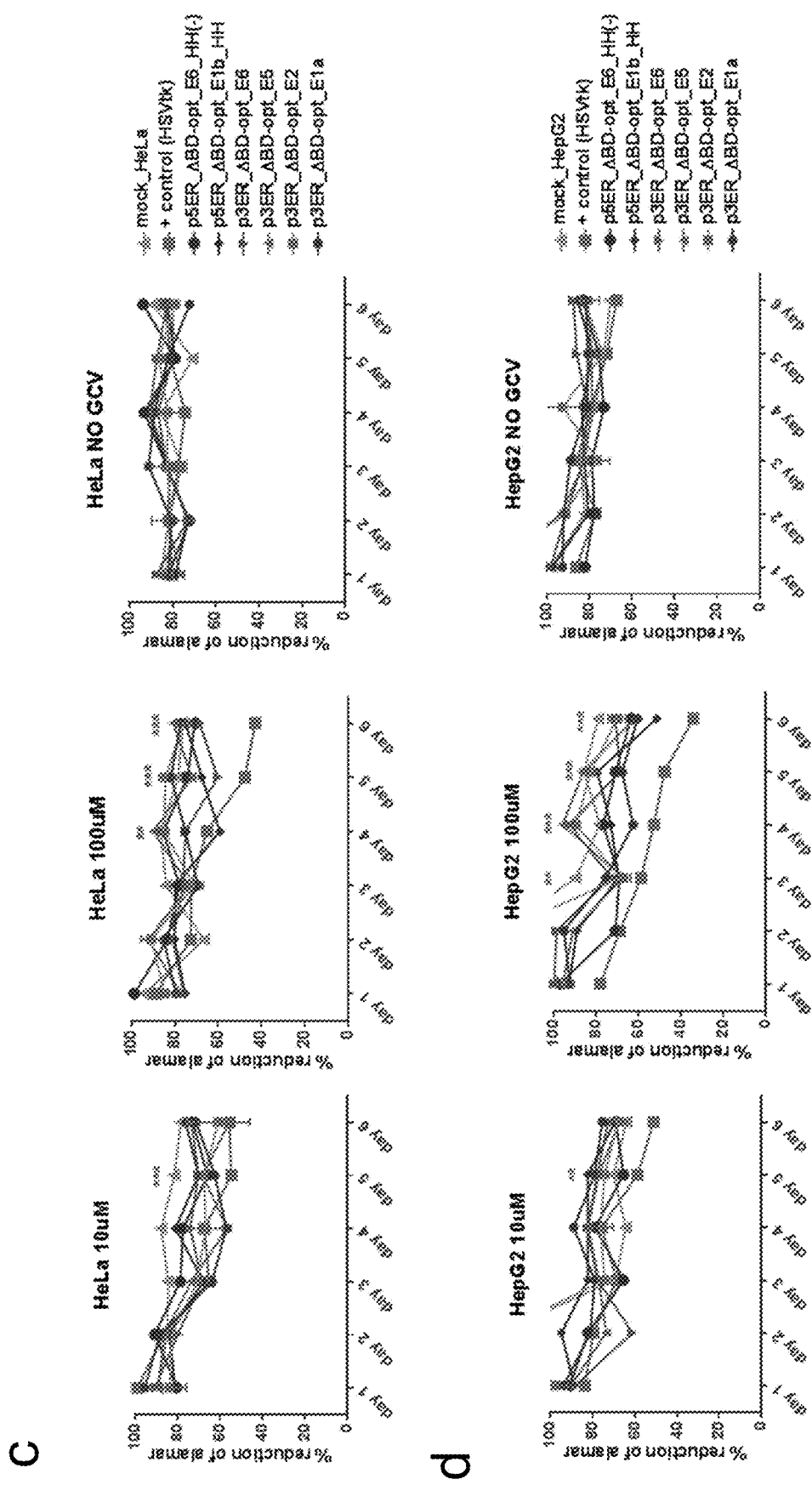

Trans-Splicing Towards Over-Expressed or Endogenous AFP Pre-mRNA Triggers Death in a Human Liver Carcinoma Cell Line As suicide gene system we chose the combination of the herpes simplex virus thymidine kinase (HSVtk) and the prodrug ganciclovir (GCV). Trans-splicing will trigger HSVtk expression in a target RNA-dependent manner which then catalyses phosphorylation of GCV into its monophosphate, which is subsequently converted into its di- and tri-phosphate derivatives by cellular kinases. The toxic GCV-triphosphate then acts as a deoxyguanosine triphosphate (dGTP) analogue, thus sitting on the DNA chain during replication, causing chain termination and cell death. We investigated death of human liver carcinoma cells HepG2 triggered by 5' or 3'ER towards the overexpressed or the endogenous AFP pre-mRNA using three different assays. Firstly, the alamar blue cell viability assay. Cells were transfected and 10 or 100 μM GCV was added to the medium 24 hours post-transfection, alamar dye was added 24 hours post drug treatment and fluorescence was measured after an incubation time of 90 min. After alamar reading, the media and drug was replenished and the process repeated for 6 consecutive days. Highest levels of cell death, i.e. up to 80% at 100 µM GCV (FIG. 5a,b) or 60 to 70% at 10 µM GCV (Supplementary FIG. 3), reaching the levels of the positive control, were triggered by trans-splicing of the parental constructs towards the over-expressed AFP message at day 6 of the treatment. Likewise high levels of cell death were observed with the 3'ER construct containing all four BDs and for the 5'ER construct with the mutated HHRz cleavage motif. 3'ER with the endogenous AFP RNA was slightly less efficient. As expected, lower levels of cell death were triggered by the partly inactive HSVtk mutant, the splice site mutants, and the RNAs lacking an AFP-specific BD. No cytotoxicity was triggered by the AFP mini-gene or the trans-splicing constructs in the absence of GCV. Secondly, to monitor specific modes of cell death triggered by our system, we employed the Annexin V/propidium iodide (PI) apoptosis assay. Therefore HepG2 cells were transfected, treated with 100 µM GCV for 48 hours, and analysed using flow cytometry. In order to assay transfected cells only, we initially co-transfected an EGFP expression vector together with the trans-splicing vectors and the AFP mini-gene (Supplementary FIG. 4). The active trans-splicing constructs were found to trigger higher levels of apoptosis (up to 50%) compared with the partly inactive constructs or the controls but a substantial fraction (30%) of apoptotic cells were not EGFP-positive (supplementary FIG. 8d). To avoid any shortcomings associated with co-transfection of multiple plasmids, we inserted an SV40 promoter-driven EGFP gene into the trans-splicing vectors, the AFP mini-gene vector, and the HSVtk vector so that cell could be transfected with only one (endogenous target) or two (over-expressed target) plasmids (FIG. 5c,d,e). The most active 3'ER constructs with the optimized BD or multiple BDs as well as the best 5'ER constructs harbouring the HHRz with the active or inactive cleavage motif triggered apoptosis in more than 40% of the AFP over-expressing cells. Half as many apoptotic cells were detected in cells expressing only endogenous AFP. An exception was the 5'ER construct with the mutated HHRz cleavage site which triggered comparable high levels of apoptosis with both the endogenous and the over-expressed AFP. This tsRNA represents a fully intact stable mRNA harbouring a 5' cap and a 3' poly A tail even without undergoing trans-splicing towards the target. Hence, the high cell death activity of this tsRNA might be either due to nuclear export and HSVtk translation in the absence of trans-splicing and/or alternatively due to high endogenous stability and subsequent high rates of trans-splicing which indeed were measured for this RNA (FIG. 3d). The mode of HSVtk/GCV-triggered cell death was pre-dominantly reported as apoptosis involving DNA double-strand breaks. To confirm that a substantial proportion of cells were killed by apoptosis, we thirdly performed the comet assay which allows visualization of partially degraded DNA after single-cell gel electrophoresis. Therefore HepG2 cells were co-transfected with the trans-splicing constructs and the AFP mini-gene, incubated at 100 µM GCV and after 24 hours, the DNA breaks were recorded as tail moment. The results are in accordance with those obtained in the alamar blue and Annexin V/PI assays: most DNA breaks were triggered by the multiple BD or parental 3'ER RNAs or the case of 5'ER by the RNA harbouring the mutated HHRz cleavage site and the parental sequence (FIG. 5f).

Trans-Splicing RNA Simultaneously Targeting Two Endogenous Liver Cancer Markers Triggered Enhanced Cell Death at 10-Fold Lower Ganciclovir Doses As many other human diseases, the carcinogenesis of hepatocellular carcinoma (HCC) is a multi-factorial, multi-step, complex process and a single biomarker is not accurately indicating the disease and its stages. To increase both HCC specificity and sensitivity of our approach, we investigated bispecific (dual targeting) tsRNAs targeting two HCC biomarkers simultaneously using distinct BDs. Multiple HCC biomarkers have been reported in the literature and we measured the abundance of 12 corresponding pre-mRNAs and mRNAs in 10 different cell lines or cells (Supplementary FIG. 5a). Based on the abundance in our test cell lines, HCC-specificity, and clinical meaning we selected three genes: Firstly, HCCA2 (YY1AP1), a HCC associated protein that is upregulated in liver cancer patients; secondly CD24, a surface marker glycoprotein and marker for high invasiveness and metastatic potential of cells in late stage HCC; and thirdly VEGF, a cytokine playing an important role in tumour angiogenesis and biomarker of lymph node metastasis in HCC. We designed dual targeting trans-splicing RNAs considering all six combinations of the AFP and one secondary target BD separating the BDs with a spacer sequence and investigated trans-splicing-mediated death of HepG2 cells targeting only endogenous pre-mRNAs using the alamar blue cell viability assay (FIG. 5g,h). At 10 µM GCV, all dual targeting constructs triggered significantly higher levels of cell death compared with the construct targeting AFP only (FIG. 5h); at 100 µM GCV however, single and dual targeting constructs showed comparable effects (Supplementary FIG. 5b).

Figure 6:
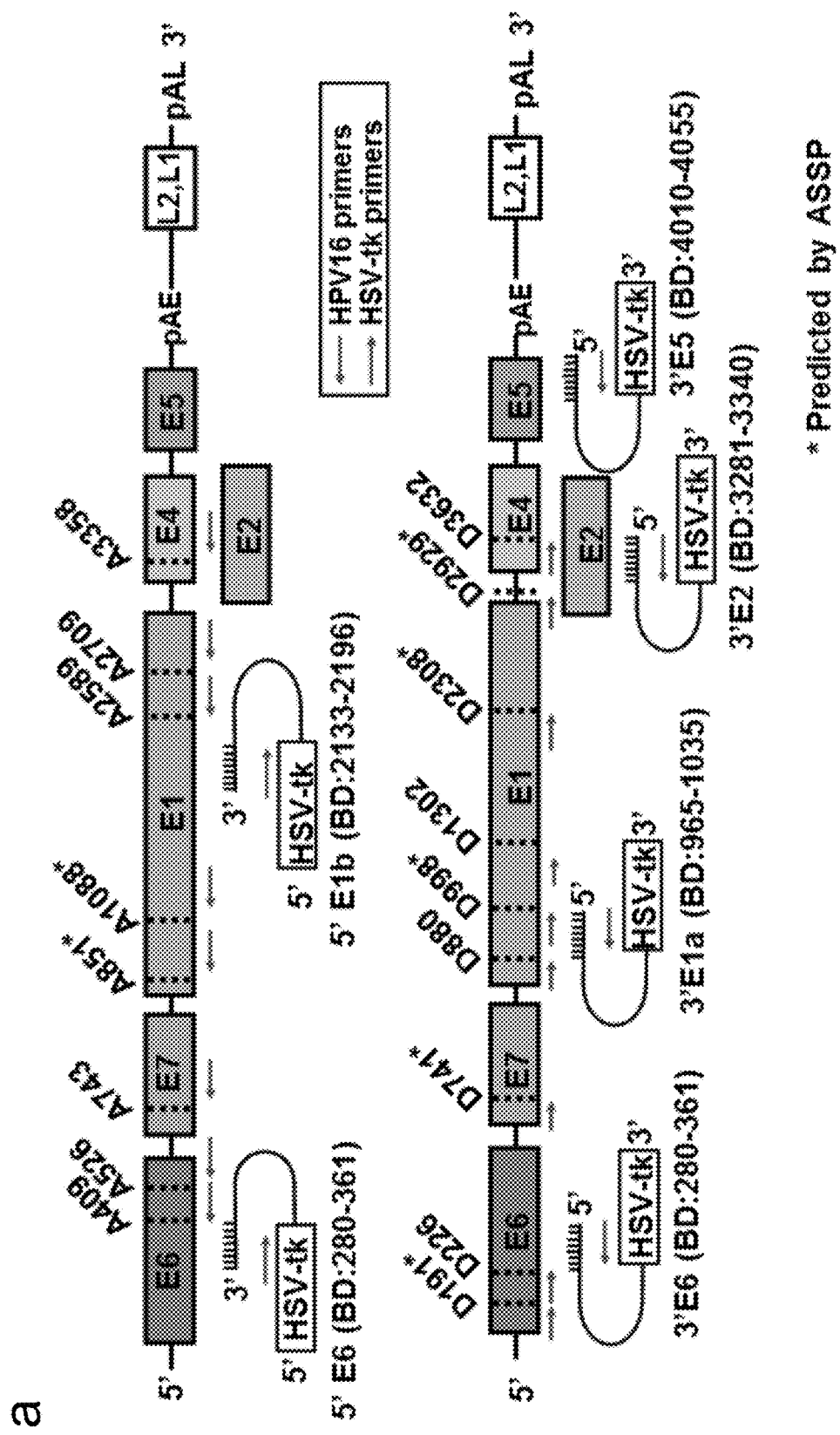
FIG. 6 Labelling HSVtk death signal by trans-splicing to HPV16 positive cells using 3'ER and 5'ER. (a) Schematic map of HPV16 genome containing six early (E) and two late (L) genes showing available splice acceptors (A) and splice donors (D) the viral cells utilizes for alternative splicing. A total of 6 trans-splicing RNAs were designed (5'E6 and 5'E1b for 5'ER) and (3'E6, 3'E1a, 3'E2 and 3'E5 for 3'ER). The light arrows show the positions of RP (5'ER) and FP (3'ER) used for detection of multiple trans-splicing events and the dark arrows show the position of primers in the HSVtk region of the trans-splicing constructs. (b) Quantification of the trans-splicing events with endogenous HPV16 target using real time RT-PCR and denoted as ΔCt values normalized with beta-actin in HPV16 positive mouse cell line C3 (top panel) and human cell line SiHa (bottom panel) for both 3'ER (left panel) and 5'ER (right panel). The absence of bar in the graph for some SD and SA denotes undetermined trans-splicing. n=3, mean±SEM. (c) Alamar Blue cell viability assay performed on selected trans-splicing constructs at endogenous HPV16 positive cell lines SiHa (top left), C3 (top right) and HPV18 positive human cell line HeLa (bottom left) and HPV16/18 negative cell line HepG2 (bottom right) when treated with 100 µM GCV for a span of 6 days. n=3, mean±SEM, test for significance used was two-way ANOVA with Bonferroni post-hoc compared to mock.* p<0.05, p<0.01, *p<0.001 and **** p<0.0001.
Figure 6:
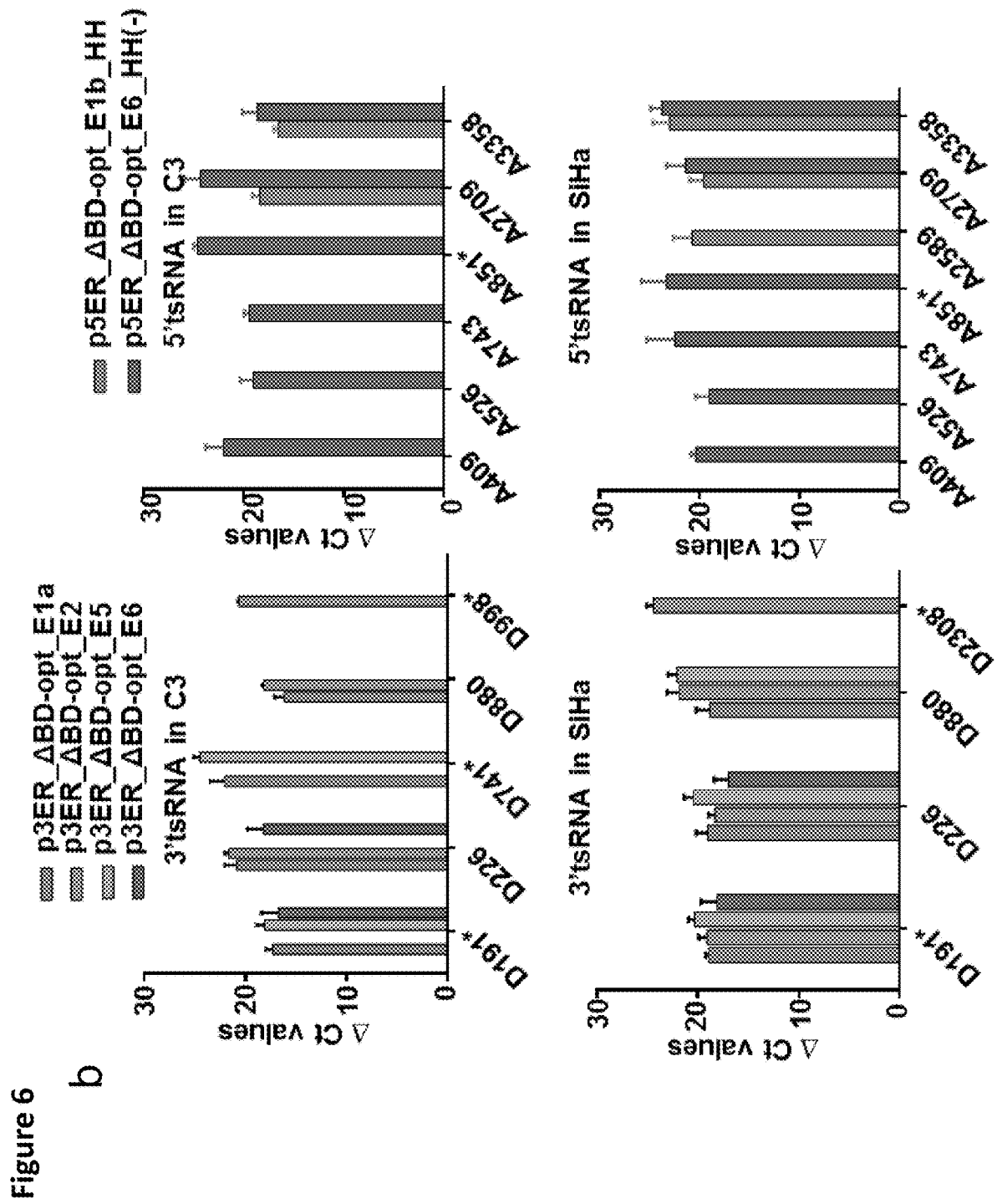
Figure 6:
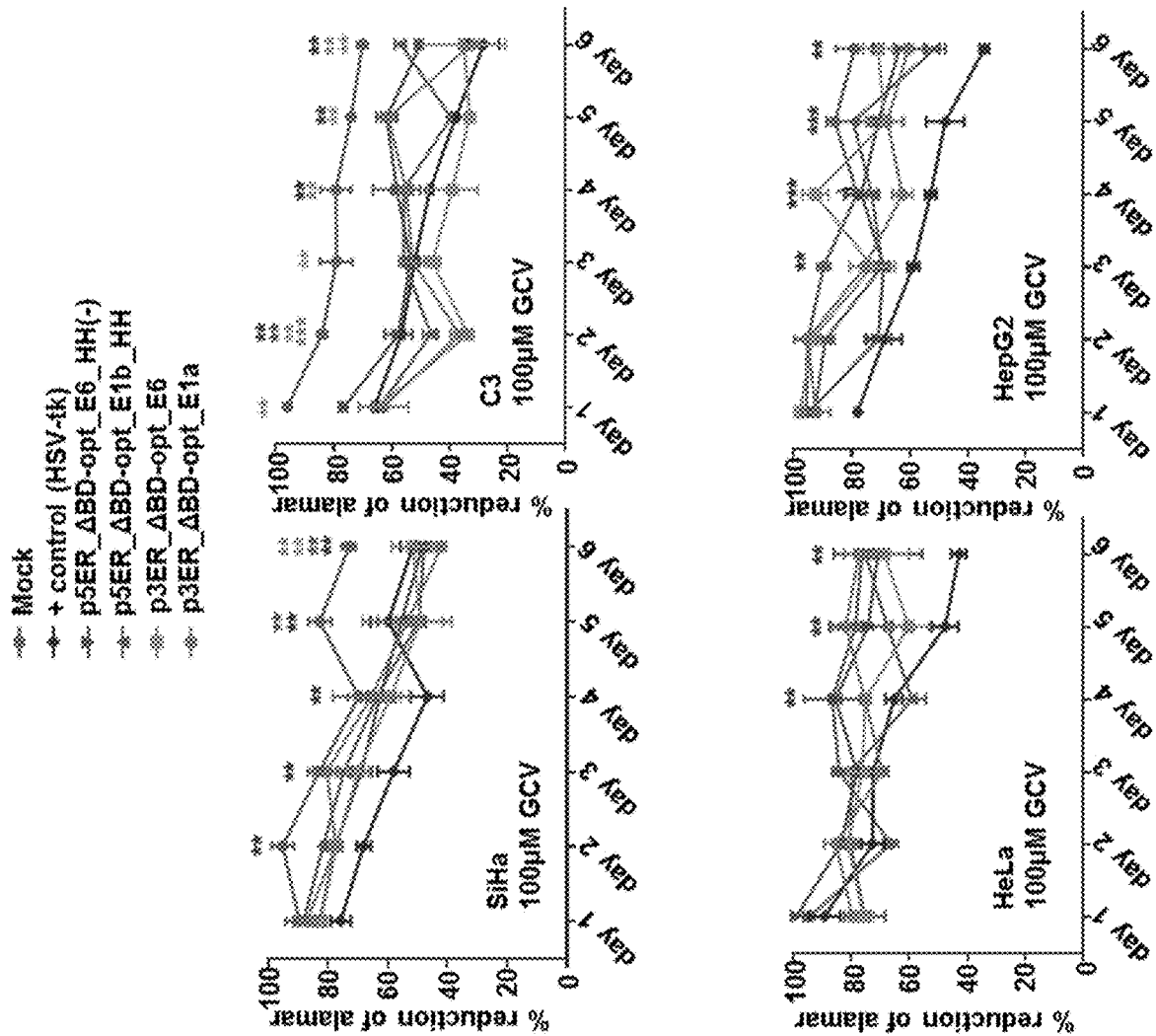
Figure 7:
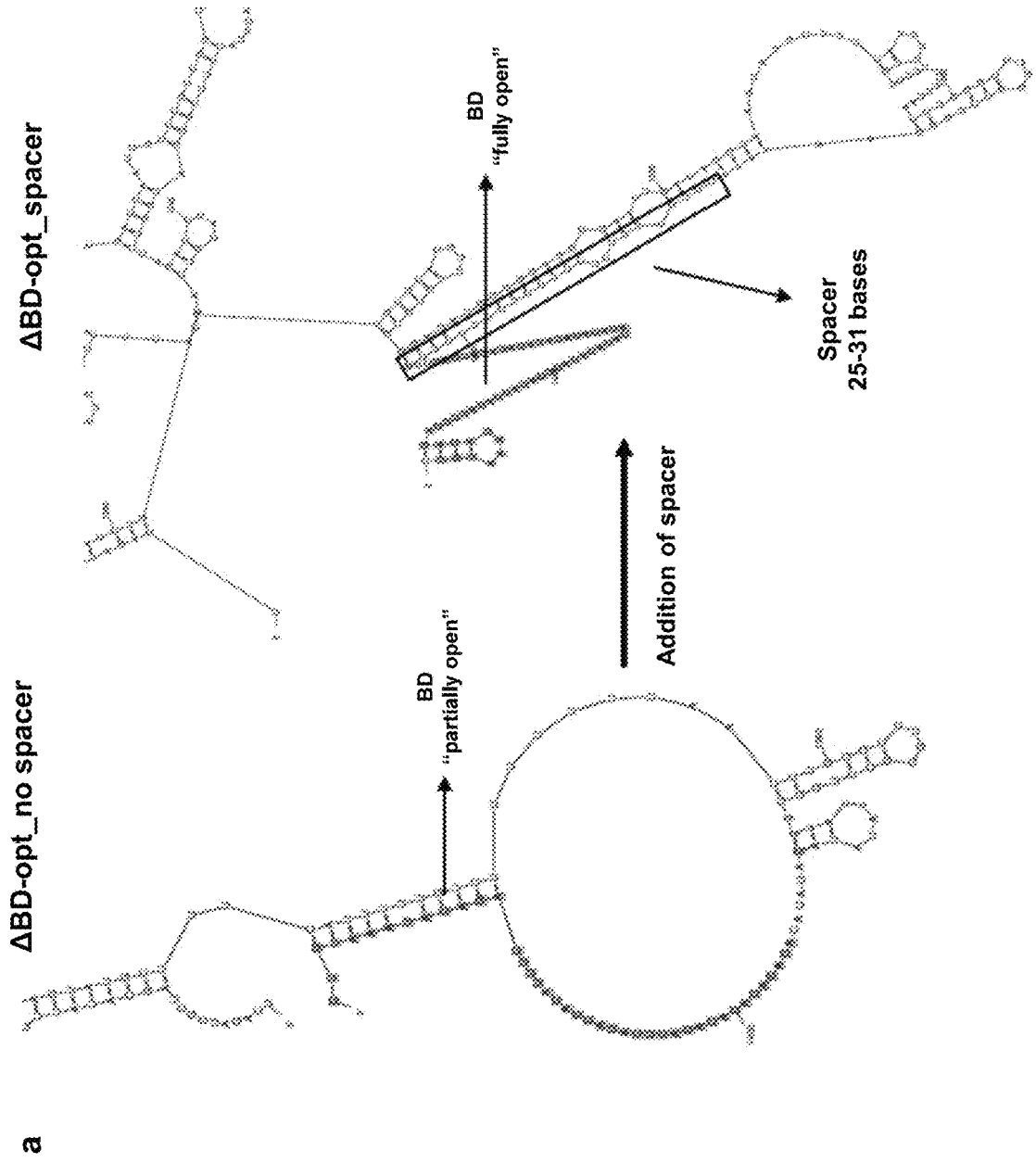
FIG. 7 RNA secondary structures showing the BDs of 3'ER constructs. (a) Introduction of a spacer sequence either upstream or downstream of BD to make it unstructured. (b) The parental 3'ER optimised and unstructured binding domain ("open" highlighted) was designed with two mismatches to AFP target (ΔBD) and compared with existing BD design (with no target mismatch). The box shows the region of change between the two constructs, the RNA folding remains the same. (c) (d) The 3'ER_ΔBD struc1 (overlapping 3 bases with the unstructured 3'ER_ΔBD-opt) and 3'ER_ΔBD struc2 (67 bases upstream of 3'ER_ΔBD-opt and 27 bases upstream of 3'ER_ΔBD struc1) selected shows closed RNA secondary structure less optimal for target binding. (e) The p3ER_opt-inv constructs with either ΔBD or BD was designed keeping the original ΔBD or BD respectively and changing the spacer into an inverted repeat with some mismatches resulting in a completely structured long stem structure with less trans-splicing activity.
Figure 7:
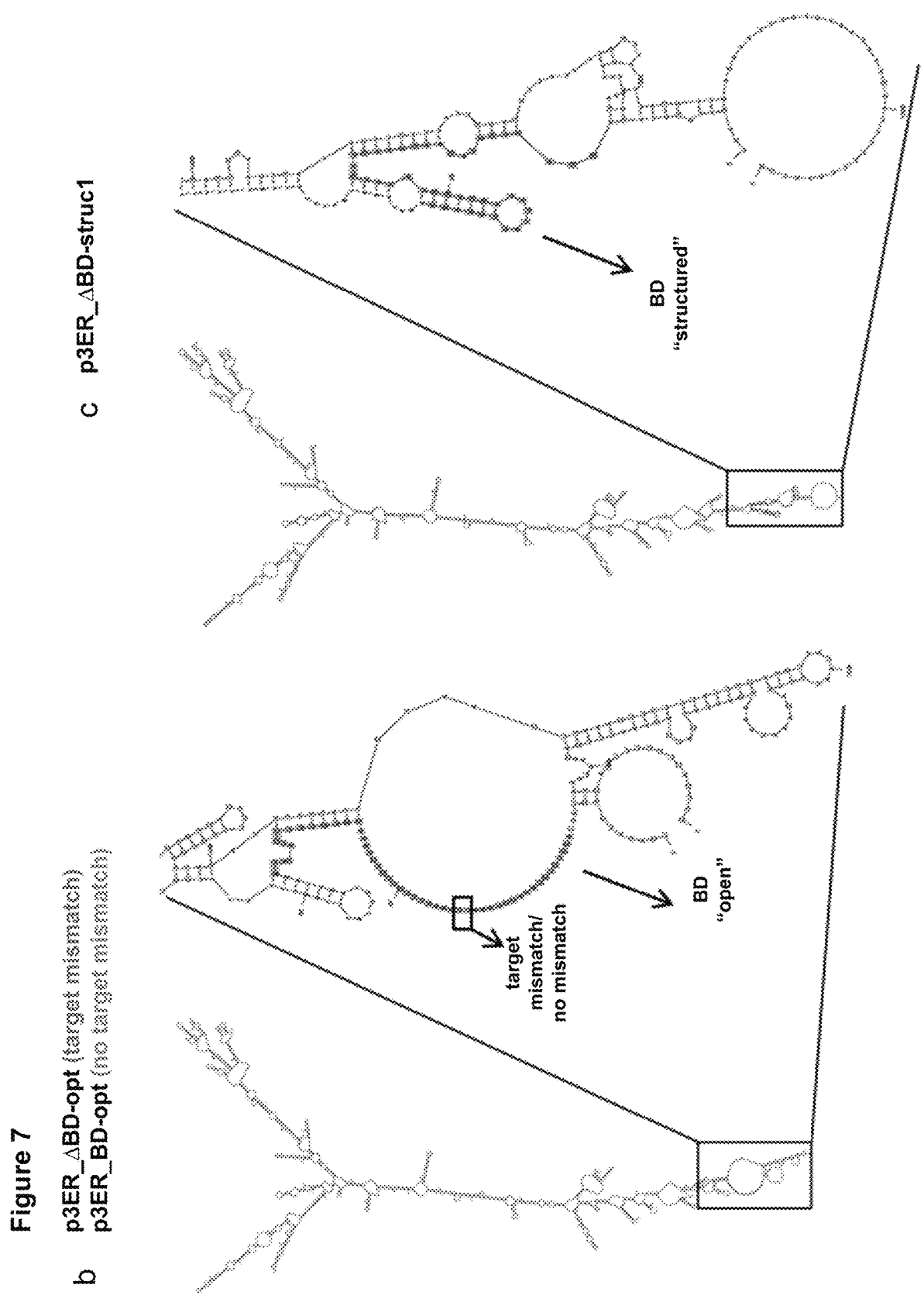
Figure 7:
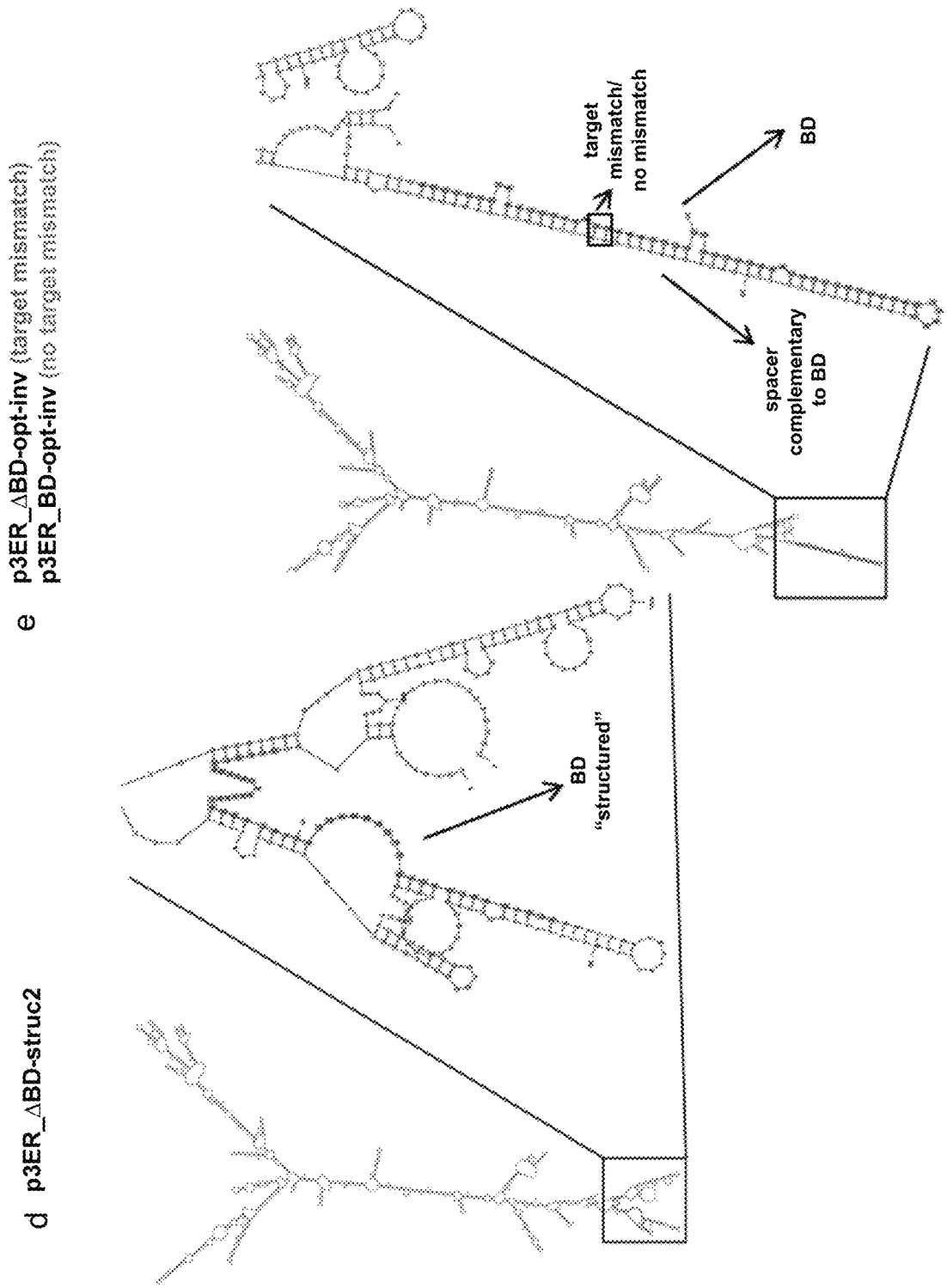

HPV-16-Targeting Suicide RNA Specifically Killed HPV-16-Transformed Tissue Culture Cells The universal design of our tsRNA facilitates replacement of the BD together with the spacer in order to target any pre-mRNA of interest. As a second clinically relevant target we chose the human papillomavirus type 16 (HPV-16). HPVs establish productive infections in keratinocytes of the skin and the mucous membranes causing benign papilloma's, premalignant lesions, and cancer. HPV infection is the most frequent sexually transmitted disease worldwide and the two high risk types HPV-16 and HPV-18 cause about 70% of all cervical cancer cases. Prior to cell transformation, HPV-16 genomes integrate into the host cell genome and there is no way to erase the viral DNA from an infected individual. However, selective destruction of the infected cells by suicide gene therapy may represent an approach to solving this problem. In HPV infections, alternative splicing generates multiple isoforms of viral mRNA. We computationally selected the five most favourable unstructured anti-sense BDs (opt_E6, _E1a, _E1b, _E2 and _E5) which can be directed against HPV-16 transcripts targeting the early viral genes E6, E1, E2, and E5 (FIG. 6a). Selected BDs of 46 to 82 nt in length together with appropriate structure-preserving spacers were cloned into the parental trans-splicing vectors to generate four constructs for 3'ER and two for 5'ER. Each of the resulting 5'ER or 3'ER tsRNAs can recruit multiple alternative viral splice acceptor or donor sites which were either published or predicted by us using splice site predictor algorithm ASSP. We monitored the usage of these splice sites for trans-splicing in the HPV-16 transformed cell lines SiHa (human, 2 viral genome copies) and C3 (murine, multiple truncated and complete viral genome copies) using rtRT-PCR (FIG. 6b). In both cell lines, HPV-16 transcripts are highly abundant. The 5'ER vectors and the two most active 3'ER constructs E1 and E6 were then tested for their potential to trigger cell death relative to the HSVtk expression vector (positive control) using the alamar blue cell viability assay and a GCV concentration of 100 μM. Cell death was selectively triggered in HPV-16 transformed cell lines SiHa and C3 but not in HPV-18-transformed HeLa cells or in the HPV-negative cell line HepG2 (FIG. 6*c*, Supplementary FIG. 6). In SiHa cells, all tsRNAs triggered cell death to the same extent as the positive control; in C3 cells 3'ER was more efficient than 5'ER.

Figure 13:
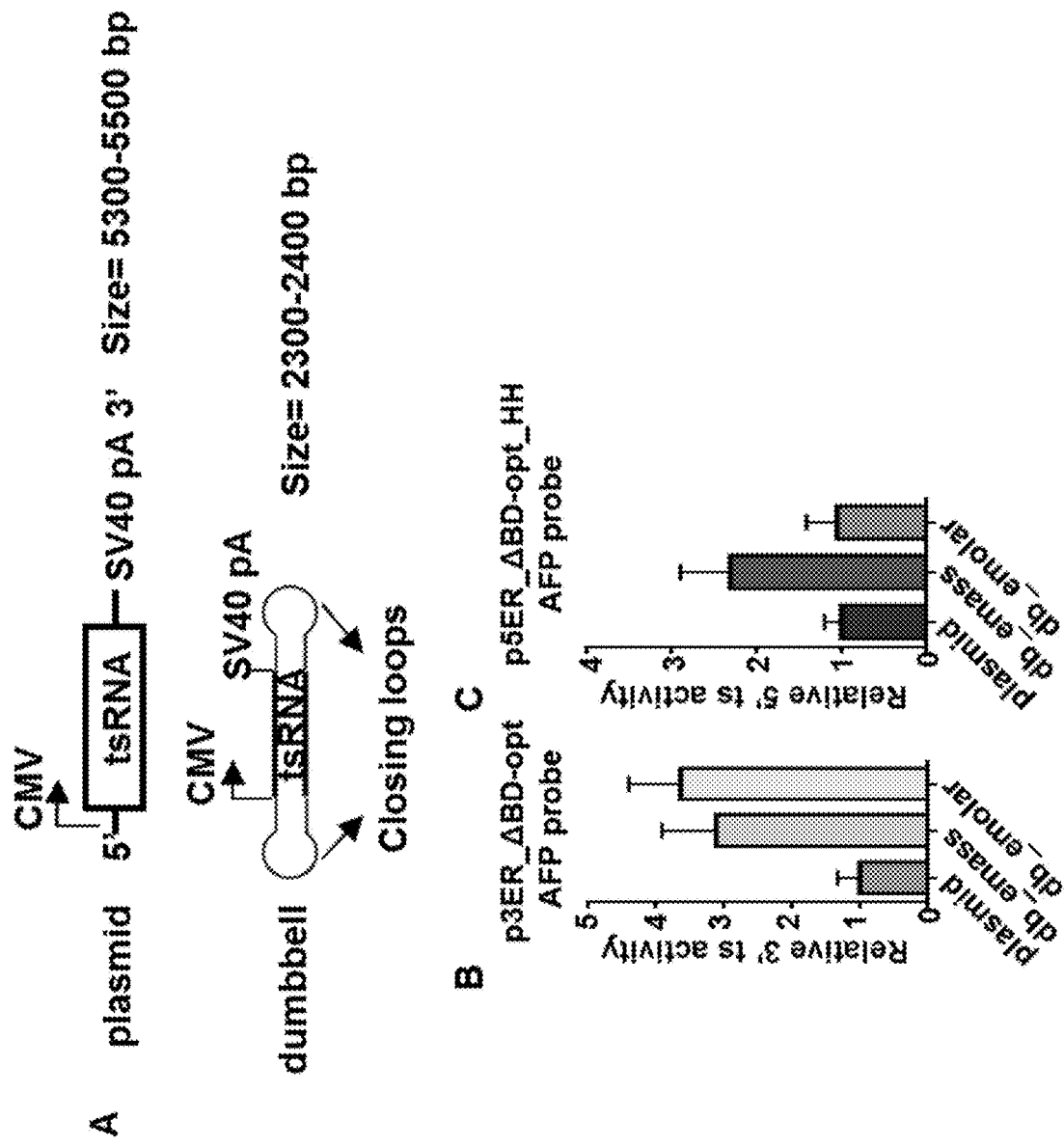
FIG. 13 Delivery of RNA trans-splicing using dumbbell-shaped DNA minimal vectors (a) Synthesis of dumbbells from tsRNA plasmids by ELAN method. Schematics of both plasmid and dumbbell vectors with mentioned sizes. (b) Efficiency of 3'ER and (c) 5'ER dumbbells in both equimass and equimolar tested against plasmid tsRNA constructs with AFP TaqMan rtRT-PCR detection system. All data represent mean±SEM from three independent experiments. Test for significance used was two-way ANOVA with Tukey post-hoc.

Minimalistic Dumbbell-Shaped DNA Vectors for Cellular Delivery of Trans-Splicing Molecules Dumbbell-shaped DNA minimal vectors, or dumbbell vector, have several advantages over traditional plasmid vectors or viral vectors. While many viral vectors are fraught with safety risks, plasmids being much larger can trigger side effects including immunotoxicity and suffer from transgene silencing in primary cells. Dumbbells do not have these disadvantages and compared with plasmids are more efficient in terms of cellular delivery, nuclear diffusion, and gene expression. First-time we generated dumbbell vectors to deliver RNA trans-splicing. That was achieved by cutting the trans-splicing cassette out from the plasmid and subsequently closing the ends by ligation of hairpin loop structures (FIG. 13*a*). This method is known as ELAN method. HepG2 cells were co-transfected with the AFP mini-gene plasmid and either equimolar or equimass amounts of dumbbells were administered. In case of 3'ER, equimolar and equimass amounts of dumbbells triggered higher levels of trans-splicing as compared with the plasmid (FIG. 13*b*). In case of 5'ER, only equimass amounts of dumbbell DNA showed higher levels of trans-splicing (FIG. 13*c*).

LIST OF OLIGONUCLEOTIDES, PROBES AND PRIMERS

List of oligonucleotides, probes and primers

| No. | Oligonucleotide names | Sequence (5'-3') | Modifications |
|---|---|---|---|
| | | For general cloning and sequencing | |
| SEQ ID NO: 1 | FP-pVAX1 (set 1) | GACTCTTCGCGATGTACGGG | |
| SEQ ID NO: 2 | RP-pVAX1 (set 1) | GTGTTGATGCAGGGGTACG | |
| SEQ ID NO: 3 | FP-pVAX1 (set 2) | TTACCCTGTTTCGGGCCC | |
| SEQ ID NO: 4 | RP-pVAX1 (set 2) | GCTCCCAACCTTACCAGAGG | |
| SEQ ID NO: 5 | FP-pVAX1 (set 3) | CGGTTTGACTCACGGGGAT | |
| SEQ ID NO: 6 | RP-pVAX1 (set 3) | GGCAAACACAGATGGCTGG | |
| SEQ ID NO: 7 | FP-pVAX1 (set 5) | CTTTTCGGGGAAATGTGCG | |
| SEQ ID NO: 8 | FP-pVAX1 (3' and 5' par) | TGAGAAAGCGCCACGCTTC | |
| SEQ ID NO: 9 | FP-pSUPER (set 1) | GTGAGCGCGCGTAATACGA | |
| SEQ ID NO: 10 | RP-pSUPER (set 1) | AGGCACCCCAGGCTTTACAC | |
| SEQ ID NO: 11 | FP-pEGFP.C2 (set1) | CAAGTGAACTTCAAGATCCGC | |
| SEQ ID NO: 12 | RP-pEGFP.C2 (set1) | ATTGCATTCATTTTATGTTTCAGGTTC | |
| SEQ ID NO: 13 | FP 3'BAD | GACGCAAATGGGCGGTAG | |
| SEQ ID NO: 14 | FP-5'par (2) | GTGAACCGTCAGATCGCTAGC | |
| SEQ ID NO: 15 | RP-5'par (3) | CACAGGGTGAGATATCGGCC | |
| SEQ ID NO: 16 | FP-5'par (4) | AGGCTCCATACCGACGATCT | |
| SEQ ID NO: 17 | RP-5'par (2) | CGGGCGATTGGTCGTAATCC | |
| SEQ ID NO: 18 | FP-5'par (3) | TGTCTCGACAAGCCCAGTT | |
| SEQ ID NO: 19 | RP-5'par (4) | CAATGGGGCGGAGTTG | |
| SEQ ID NO: 20 | RP-5'par (5) | CCATTGACGTCAATGGGGTGG | |
| SEQ ID NO: 21 | FP-BssHII (check par change) | ACCTGGCGCGCACGT | |
| SEQ ID NO: 22 | RP-BbsI (check par change) | CCAGCATGCCTGCTATTGTCT | |
| SEQ ID NO: 23 | FP-3'ss mut change (NheI) | TCAGATCGCTAGCACCCTCTCTAAA | |

List of oligonucleotides, probes and primers

| No. | Oligonucleotide names | Sequence (5'-3') | Modifications |
|---|---|---|---|
| SEQ ID NO: 24 | RP-3'ss mut change (PvuI) | AAAAAACGATCGGCAGACAACCCAGGCCCAGGCC | |
| SEQ ID NO: 25 | FP-5'ss mut change (BssHII) | CCTGGCGCGCACGTTTGCGCGGGAGATGGGGGAGGCGAACTGATACACG | |
| SEQ ID NO: 26 | FP-5'ss mut change (mismatch) | GGAGGCGAACTGATACACGGCATAGCTTTCATTTTTGTCTTTTTTAAC | |
| SEQ ID NO: 27 | RP-5'ss mut change (KpnI) | GAAGGAGGGTACCCCC | |
| SEQ ID NO: 28 | FP-HSVtk (HindIII) | CTAGACATAAGCTTATGGCTTCGTACCCCTGC | |
| SEQ ID NO: 29 | RP-HSVtk (KpnI) | ACTGATCTGTACCTCAGTTCGCCTCCCCC | |
| SEQ ID NO: 30 | FP-HHRz change (mutation) | CTCATACCACATTTCAGACATAAATACATCCCCACAGCCTAAGGC | |
| SEQ ID NO: 31 | FP-HHRz change (middle 2) | ATACATATACACACACACACACTCATACCACATTTCAGACATAAATG | |
| SEQ ID NO: 32 | FP-HHRz change (middle 1) | CCTCTCTCCTCCTCCTATATACATATACACACACACACTCA | |
| SEQ ID NO: 33 | FP-HHRz change (KpnI) | TGGGGTACCCCCTCCTTCCTCCTCCTCCTCCTCCTCCTATATA | |
| SEQ ID NO: 34 | RP-HHRz change (BbvCI) | TAAACAAGTTGCTGAGGCTATCTC | |
| SEQ ID NO: 35 | 3'NO BD oligo 1 | CTAGCGGATCCCAAGCTTCC | 5'PO$_4$ |
| SEQ ID NO: 36 | 3'BO BD oligo 2 | TGAGGAAGCTTGGATCCG | 5'PO$_4$ |
| SEQ ID NO: 37 | FP-3'block ppy (NheI) | CGCAGACGCGTGTTGATG | |
| SEQ ID NO: 38 | RP-3'block ppy (MluI) | TCAGATGCTAGCCTGGAAAAAATCGGAAAAAAAACCTCTAAACCTAAATTAATTTTCTTCTC | |

For real time RT-PCR to detect splicing

| SEQ ID NO: 39 | HSV-tk uni amplicon | CATGCCTTATGCCGTGACCGACG | 5'FAM 3'BHQ |
| SEQ ID NO: 40 | AFP probe exon 4 | CTTGCACACAAAAAGCCCACTCCAGC | 5'FAM 3'BHQ |
| SEQ ID NO: 41 | AFP probe exon 5 | CCTACAATTCTTCTTTGGGCTGCTCGCT | 5'FAM 3'BHQ |
| SEQ ID NO: 42 | HSV-tk probe (for 3ER) | CCCCTGCCATCAACACGCGTC | 5'FAM 3'BHQ |
| SEQ ID NO: 43 | HSV-tk probe (for 5ER) | CGACCTGGCGCGCACGTTT | 5'FAM 3'BHQ |

-continued

List of oligonucleotides, probes and primers

| No. | Oligonucleotide names | Sequence (5'-3') | Modifications |
|---|---|---|---|
| SEQ ID NO: 44 | FP-HSV-mini intron uni amp | GACATCCACTTTGCCTTTCTC | |
| SEQ ID NO: 45 | FP-HSV-uni amp | AAGCCCCAGATAACAATGG | |
| SEQ ID NO: 46 | FP-HSV tk half half uni amp | GCCTCGACCAGGGTGAGAT | |
| SEQ ID NO: 47 | RP-HSV-uni amplicon | CTCATATCGGGGGGAGG | |
| SEQ ID NO: 48 | RP-afp exon 3 | TTATTCACTCACCTGGTTTTCTAAACA | |
| SEQ ID NO: 49 | FP-afp intron 5 | GTAAATTTGTCTGGCACAGATGCA | |
| SEQ ID NO: 50 | FP afp uni amp exon 4 | AAGTGAAGAGGGAAGACATAACTGTTT | |
| SEQ ID NO: 51 | RP afp exon 4 (set 1) | GAACTTGGAAAAGTGGGATCGA | |
| SEQ ID NO: 52 | RP afp uni amp exon 5 | CATAGCGAGCAGCCCAAAG | |
| SEQ ID NO: 53 | FP-HSV-tk (set 1) | GATGGGGGAGGCGAACTG | |
| SEQ ID NO: 54 | FP-afp exon 3 | AGTCTTCAGGGTGTTTAGAAAACCA | |
| SEQ ID NO: 55 | FP-afp exon 5 (set 1) | AAGGCATCCCTTCCTCTGTATGC | |
| SEQ ID NO: 56 | RP-afp exon 6 | AAGTCTGCTTTCTCTTAATTCTTTTGTAAC | |
| SEQ ID NO: 57 | FP-HSV-tk (set 2) | CAGGCTCCATACCGACGATC | |
| SEQ ID NO: 58 | RP-afp exon 4 (set 2) | TTCTCATGCAAAGTTCTTCCA | |
| SEQ ID NO: 59 | FP-afp exon 5 (set 2) | CATCTTGCTGCAAAGCTGAAAA | |
| SEQ ID NO: 60 | RP-HSV-tk | TTGCTGTGTCCCCGTGATC | |
| SEQ ID NO: 61 | FP-HSVtk (for 3ER) | CGTTTAAACTTAAGCTTATGGCTTCG | |
| SEQ ID NO: 62 | RP-HSVtk (for 5ER) | CAGTTCGCCTCCCCCATC | |
| SEQ ID NO: 63 | Stem loop uni probe | TCGCACTGGATACG | 5'FAM 3'BHQ |
| SEQ ID NO: 64 | FP-5'HH cleavage | ACACACACACTCATACCACATT | |
| SEQ ID NO: 65 | Stem Loop 5'par | GTCGTATCCAGTGCAGGGTCCGAGGTATTCGCACTGATACGACACATTT | |
| SEQ ID NO: 66 | Stem Loop 5'HH mut | GTCGTATCCAGTGCAGGGTCCGAGGTATTCGCACTGATACGACGGTATT | |

-continued

List of oligonucleotides, probes and primers

| No. | Oligonucleotide names | Sequence (5'-3') | Modifications |
|---|---|---|---|
| SEQ ID NO: 67 | RP-stem loop uni | CAGTGCAGGGTCCGAGGT | |
| SEQ ID NO: 68 | HCCA2-FP-exon 2 | CCCTCTTCCTCACTTCCCTGTACT | |
| SEQ ID NO: 69 | HCCA2-RP-exon 3 | CATCAGCTCATTTGCTTCCTTTT | |
| SEQ ID NO: 70 | CD24-FP-exon 2 | GACATGGGCAGAGCAATGGT | |
| SEQ ID NO: 71 | CD24-RP-exon 3 | ACTCTGGGAGGAGTTACTTGAAGTTC | |
| SEQ ID NO: 72 | VEGF-FP-exon 2 | AGAAGGAGGGGCAGAATCA | |
| SEQ ID NO: 73 | VEGF-RP-exon 3 | AGCTGCGCTGATAGACATCCA | |

For real time RT-PCR to detect HCC markers

| SEQ ID NO: 74 | FP-AFP | TTTGGGCTGCTCGCTATGA | |
| SEQ ID NO: 75 | RP-AFP (exon) | TTGTTTGGAAGCATTCAACTGC | |
| SEQ ID NO: 76 | RP-AFP (intron) | GACTACAGTACTGGTTCAGATATCCACG | |
| SEQ ID NO: 77 | FP-CD24 | GCATCCTGCTAGACGCGC | |
| SEQ ID NO: 78 | RP-CD24 (exon) | TGCGTGGGTAGGAGCAGTG | |
| SEQ ID NO: 79 | RP-CD24 (intron) | GCGCCAGGGCCTCAC | |
| SEQ ID NO: 80 | FP-HCCA2 | CTAGGAAAATGCTGTGAAGAGATCC | |
| SEQ ID NO: 81 | RP-HCCA2 (exon) | CCAGAATGGGAGCCGGT | |
| SEQ ID NO: 82 | RP HCCA2 (intron) | TTCTGCCTCCTACAGACTTCGAG | |
| SEQ ID NO: 83 | FP-HSP70 | TACGTGGCCTTCACGGACA | |
| SEQ ID NO: 84 | RP-HSP70 | AACTTGCGGCCAATCAGC | |
| SEQ ID NO: 85 | FP-AFU | TCCTGTGTCTTTGGAACTGTGAAACT | |
| SEQ ID NO: 86 | RP-AFU (exon) | CTTCCGGAGAGCTGTTCCC | |
| SEQ ID NO: 87 | RP-AFU (intron) | CCAGATCCAAAGAAGATAACAGAGTAACC | |
| SEQ ID NO: 88 | FP-TGFB1 | CAAGGACCTCGGCTGGAAG | |
| SEQ ID NO: 89 | RP-TGFB1 (exon) | TGCTGTACTGCGTGTCCAGG | |
| SEQ ID NO: 90 | RP-TGFB1 (intron) | GCATCTCGTAGCCCGGTG | |

-continued

List of oligonucleotides, probes and primers

| No. | Oligonucleotide names | Sequence (5'-3') | Modifications |
|---|---|---|---|
| SEQ ID NO: 91 | FP-VEGF | AGTACATCTTCAAGCCATCCTGTGT | |
| SEQ ID NO: 92 | RP-VEGF (exon) | GGTGATGTTGGACTCCTCAGTG | |
| SEQ ID NO: 93 | RP-VEGF (intron) | TTGCCCACTTCCCAAAG | |
| SEQ ID NO: 94 | FP-GPC3 | CGGACGCCACCTGTCAC | |
| SEQ ID NO: 95 | RP-GPC3 (exon) | TGGCACGGGAGTTTCTGG | |
| SEQ ID NO: 96 | RP-GPC3 (intron) | TAGCGCGTCAGGGTACAG | |
| SEQ ID NO: 97 | FP-IGFII | GGAAGCTGTTGATACCAAAAATAATG | |
| SEQ ID NO: 98 | RP-IGFII (exon) | GATAAGTGCGTGTCTTCAAGTCGT | |
| SEQ ID NO: 99 | RP-IGFII (intron) | TTGCCAATCCAGTAATTCAGGTAG | |
| SEQ ID NO: 100 | FP-GGT | GGTCCTGGTGCTGGTCATTG | |
| SEQ ID NO: 101 | RP-GGT (exon) | TCCCAATCTTCGAGCACTGC | |
| SEQ ID NO: 102 | RP-GGT (intron) | ATGTCCCATGCCCTGCC | |
| SEQ ID NO: 103 | FP-GP73 | CAGGCTGCCCTGTCAGTGA | |
| SEQ ID NO: 104 | RP-GP73 (exon) | CCGGCAGCTTCCTGCTC | |
| SEQ ID NO: 105 | RP-GP73 (intron) | GTCTGGTGGAAGGGAGTCCA | |
| SEQ ID NO: 106 | FP-HGP | TTGATAAAGCAAGAGAAAACAATGCC | |
| SEQ ID NO: 107 | RP-HGP (exon) | TTTGTTTTCATAGAGGTCAAATTCATG | |
| SEQ ID NO: 108 | RP-HGP (intron) | TTATGCAATATTTAGGGAGAAGTCAGTTAC | |

Oligos synthesized for generating trans-splicing constructs

| SEQ ID NO: 109 | 3ER_ABD-opt | GCTAGCACCTCTCTAAACCTAAATTAAATTTTC<br>TTCTCTAAACCTCTTTCCTAGTTggactgacgtcactc<br>agtcctcctCCTCAGC | |
| SEQ ID NO: 110 | 3ER_BD-opt | GCTAGCACCTCTCTAAACCTAAAAAAATTTTC<br>TTCTCTAAACCTCTTTCCTAGTTggactgacgtcactc<br>agtcctcctCCTCAGC | |

-continued

List of oligonucleotides, probes and primers

| No. | Oligonucleotide names | Sequence (5'-3') | Modifications |
|---|---|---|---|
| SEQ ID NO: 111 | 3ER_ABD-struc1 | GCTAGCGGACTGCTTGAAGCAAGTAGTTAATG GTGGATATATTCTACCggactgacgtcactcagtcctcct CCTCAGC | |
| SEQ ID NO: 112 | 3ER_ABD-struc2 | GCTAGCCTTCTCAGTTACACAAAAATACGATGTT ATCACGGCTTGACACTGAGAGTAggactgacgtcac tcagtcctcctCCTCAGC | |
| SEQ ID NO: 113 | 3ER_ABD-opt-inv | GCTAGCACCTCTCTAAACCTAAATTAAATTTTC TTCTCTAAACCTCTTTCCTAGTTaactaggaaagag gttagagagaaattaattaggttgagaggtCCTCAGC | |
| SEQ ID NO: 114 | 3ER_BD-struc1 | GCTAGCGGACTGCTGGTAGCAAGTAGTTAATG GTGGATATATTCTACCggactgacgtcactcagtcctcct CCTCAGC | |
| SEQ ID NO: 115 | 3ER_BD-struc2 | GCTAGCCTTCTCAGTTACACAAAAATACGATTGT ATCACGGCTTGACACTGAGAGTAggactgacgtcac tcagtcctcctCCTCAGC | |
| SEQ ID NO: 116 | 3ER_BD-opt-inv | GCTAGCACCTCTCTAAACCTAAAAAATTTTC TTCTCTAAACCTCTTTCCTAGTTaactaggaaagag gttagagagaaatttattaggttgagaggtCCTCAGC | |
| SEQ ID NO: 117 | 5ER_ABD-opt_HH | GGTACCcctcctcctcctcctcctcctcctATATACAT ATACACACACACACACACACTCATACCACACATTTCA GACATAAAT | |
| SEQ ID NO: 118 | 5ER_BD-opt_HH | GGTACCcctcctcctcctcctcctcctcctATATACAT ATACACACACACACACAGACATACCACATTTCA GACATAAAT | |
| SEQ ID NO: 119 | 5ER_ABD-struc1_HH | GGTACCcctcctcctcctcctcctcctcctGATGTAA CTTTTGGAATTGCAAATACATATGTATATATTAT GTAATATACATACATATATACATA | |
| SEQ ID NO: 120 | 5ER_ABD-opt-inv | GGTACCctgaaatgtagattgtgtggtgtatgtaatAT ATACATATACACACACACACACTCATACCAC ATTTCAGACATAAAT | |
| SEQ ID NO: 121 | 5ER_BD-struc1_HH | GGTACCcctcctcctcctcctcctcctcctGATGTAA CTTTTGGAATTGCAAATACATATGTATATATTAT GGTATATACATACATATATACATA | |
| SEQ ID NO: 122 | 5ER_BD-opt-inv | GGTACCctgaaatgtagattgtgtggtgtatgtaatAT ATACATATACACACACACACAGACATACCAC ATTTCAGACATAAAT | |

-continued

List of oligonucleotides, probes and primers

| No. | Oligonucleotide names | Sequence (5'-3') | Modifications |
|---|---|---|---|
| SEQ ID NO: 123 | 5ER_ABD-opt_hp_HH | GGTACCcctcctcctcctcctcctcctcctcctATATACAT ATACACACACACACTCATACCACACATTTCA TGAAATGTGTGACATAAAT | |
| SEQ ID NO: 124 | 5ER_ABD-opt_Y_HH | GGTACCcctcctcctcctcctcctcctcctcctATATACAT ATACACACACACACTCATACCACACATTTCA GACATAAATGCGTAGATAATAACCAGTGAACTT AGCGTGCATGAAAACATGCACGCTGAATCGTA GAAAAAATCTACGATTCAAGTTCACTGGAATT TATCTACGCGACATAAAT | |
| SEQ ID NO: 125 | 3ER_ABD-opt_HCCA2 | AACAGTTCCTTTATACAAATTCACCAGATGATA CAAAACATATTTTTTA | |
| SEQ ID NO: 126 | 3ER_ABD-opt_CD24 | GATCTAAAGATCCTCTACACCAACAAAATTATT ATGTTTATTAAACTGAC | |
| SEQ ID NO: 127 | 3ER_ABD-opt_VEGF | TTTCTTTCTTGATCCTTATATTCCTGTGCCCTT TTCCTTCCTCCCCACA | |

Underlined = Restriction enzymes
Lowercase = spacer/linker sequences

The invention claimed is:

1. A trans-splicing RNA (tsRNA) molecule comprising:
a plurality of binding domains specific for parts of genes that associate with or are biomarkers for a disease to be treated;
nucleic acid encoding at least one expressible suicide protein or a protein that is a component of a suicide system; and
at least one splice signal,
wherein the tsRNA includes at least one of:
said nucleic acid encoding at least one expressible protein comprises two A/G-rich exonic splice enhancers (ESE) generated by using degenerative alternative codons that do not alter the amino acid sequence;
said plurality of binding domains comprise a binding site comprising at least 25 consecutive unstructured nucleotides (nt) having no internal binding and/or self-complementary sequences and within or outside said binding site said binding domain, when of a length of 44 nt or longer, have at least one, or a plurality of, mismatch nucleotide(s) with respect to said genes; or
said plurality of binding domains are complementary to different genes that associate with or are biomarkers for a disease to be treated.

2. The trans-splicing RNA molecule according to claim 1 wherein said plurality of binding domains include a binding site that comprises a sequence of nucleotides selected from the list comprising or consisting of: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 or more nucleotides.

3. The trans-splicing RNA molecule according to claim 1 wherein said plurality of binding domains comprise a sequence of nucleotides that is at least 50%, 55%, 60%, 65%, 70%, 75%, 80%, 85%, 90%, 91, 92, 93, 94, 95, 96, 97, 98, 99% or 100% complementary to said part of a gene that associates with or is a biomarker for a disease to be treated.

4. The trans-splicing RNA molecule according to claim 1 wherein mismatches in said plurality of binding domains are positioned to avoid any stretches of 45 nt or longer that are perfectly complementary to the target, including or excluding said binding site.

5. The trans-splicing RNA molecule according to claim 1 wherein said at least one expressible suicide protein is the herpes simplex virus thymidine kinase (HSVtk).

6. The trans-splicing RNA molecule according to claim 1 wherein said tsRNA also includes a spacer sequence adjacent to said plurality of binding domains.

7. The trans-splicing RNA molecule according to claim 1 wherein said tsRNA, outside each binding domain, comprises at least one cis-binding or self-binding domain.

8. The trans-splicing RNA molecule according to claim 1 wherein said tsRNA comprises, outside each binding domain and 3' of said molecule, a highly structured sequence of RNA that is folded, or pairs with itself, due to the presence of self-complementary sequences.

9. The trans-splicing RNA molecule according to claim 1 wherein highly structured RNA is adjacent a spacer located between it and a polyA site.

10. The trans-splicing RNA molecule according to claim 1 wherein said disease is cancer or a viral infection or a bacterial infection or an acquired genetic disease caused by mutations triggered by transposable elements, radiation, chemicals, or unknown triggers.

11. The trans-splicing RNA molecule according to claim 10 wherein said cancer is hepatocellular carcinoma (HCC), cervical cancer, vaginal cancer, vulvar cancer, penile cancer, skin cancers, melanoma, malignant melanoma, squamous-cell carcinoma, basal-cell carcinoma, Merkel cell carcinoma, lung cancer, cell bladder cancer, breast cancer, colon or rectal cancer, anal cancer, endometrial cancer, kidney cancer, leukemia, acute myelogenous or myeloid leukemia (AML), acute lymphoblastic leukemia (ALL), chronic lymphocytic leukemia (CML), chronic myelogenous or myeloid leukemia (CML), hairy cell leukemia (HCL), T-cell prolymphocytic leukemia (P-TLL), large granular lymphocytic leukemia, adult T-cell leukemia, lymphoma, myeloma, non-Hodgkin lymphoma, pancreatic cancer, prostate cancer, thyroid cancer, nasopharyngeal cancer, mouth or throat cancer, oropharyngeal cancers, stomach cancer, brain tumours, bone cancer, or stem cell cancers.

12. The trans-splicing RNA molecule according to claim 10 wherein said viral infection is an infection with a retrovirus, human T-cell lymphotropic virus (HTLV), lentiviruses, human immunodeficiency virus types 1 and 2 (HIV-1 and HIV-2), human papillomavirus types 16 and 18 (HPV-16 and HPV-18), hepadnavirus HAV, HBV, HCV, HDV, and/or HEV, a herpesvirus, herpes simplex (HSV), Epstein-Barr virus (EBV), cytomegalovirus (CMV), an adenovirus, an adeno-associated virus, or an influenza virus.

13. The trans-splicing RNA molecule according to claim 10 wherein said bacterial infection is an infection with *Bartonella henselae, Francisella tularensis, Listeria monocytogenes, salmonella* species, *Salmonella typhi, Brucella* species, *Legionella* species, Mycobacteria species, *Mycobacterium tuberculosis, Nocardia species, Rhodococcus species, Yersinia species*, or *Neisseria meningitides*.

14. The trans-splicing RNA molecule according to claim 10 wherein said acquired genetic disease is Neurofibromatosis 1 and 2, Mc Cune Albright, Duchenne muscular dystrophy (DMD), Epidermolysis bullosa, Fanconi A and C, Philadelphia chromosome, Hemophilia A and B, cystic fibrosis, Muckle Wells syndrome, lipoprotein lipase deficiency, B-thalassemia, or pyruvate dehydrogenase complex deficiency.

15. A cell containing said tsRNA according to claim 1.

16. A vector containing said tsRNA according to claim 1.

17. A method of targeting a diseased cell comprising:
topical application; intranasal application; alveolar application; systemic application; oral application; intravenous application; intramuscular application; subcutaneous application; cutaneous application; intraperitoneal application; or injection into a tumor with tsRNA, or a vector containing the tsRNA, according to claim 1 in vivo and, optionally, exposing said cell to other component(s) of said suicide system effective to kill said cell.

18. A medicament comprising said tsRNA according to claim 1, further comprising at least one further component of said suicide system effective to trigger death of a cell expressing said trans-spliced RNA.

19. A pharmaceutical composition comprising said tsRNA according to claim 1, further comprising at least one further component of said suicide system effective to trigger death of a cell expressing said trans-spliced RNA; and a carrier suitable for human or veterinary use.

20. The pharmaceutical composition according to claim A wherein said one further component of said suicide system is selected from the group comprising or consisting of ganciclovir, cytosine deaminase-5-fluorocytosine, cytochrome P450-ifosfamide, cytochrome P450-cyclophosphamide, and nitroreductase-5-[aziridin-1-yl]-2,4-dinitrobenzamide.

21. The trans-splicing RNA molecule according to claim 1 wherein said nucleic acid encoding at least one expressible protein comprises two A/G-rich exonic splice enhancers (ESE) generated by using degenerative alternative codons that do not alter the amino acid sequence.

22. A trans-splicing RNA according to claim 1, wherein said binding domain comprise a binding site comprising at least 25 consecutive unstructured nucleotides (nt) having no internal binding and/or self-complementary sequences and within or outside said binding site said binding domain, when of a length of 44 nt or longer, have at least one, or a plurality of, mismatch nucleotide(s) with respect to said genes.

23. The trans-splicing RNA molecule according to claim 1 wherein said plurality of said binding domains are complementary to the same parts of a gene that associates with or is a biomarker for a disease to be treated.

24. The trans-splicing RNA molecule according to claim 1 wherein said plurality of binding domains are complementary to different genes that associate with or are biomarkers for a disease to be treated.

25. A trans-splicing RNA (tsRNA) molecule comprising:
a plurality of binding domains specific for parts of genes that associate with or are biomarkers for a disease to be treated;
nucleic acid encoding at least one expressible protein; and
at least one splice signal,
wherein said plurality of binding domains comprise a binding site comprising at least 25 consecutive unstructured nucleotides (nt) having no internal binding and/or self-complementary sequences and within or outside said binding site said binding domain, when of a length of 44 nt or longer, have at least one, or a plurality of, mismatch nucleotide(s) with respect to said genes.

* * * * *

SEQUENCE LISTING

<160> NUMBER OF SEQ ID NOS: 148

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide, probe or primer

<400> SEQUENCE: 1
gactcttcgc gatgtacggg                                               20

<210> SEQ ID NO 2
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 2
gtgttgatgg cagggtacg                                                20

<210> SEQ ID NO 3
<211> LENGTH: 18
<212> TYPE: DNA
<213> ORGANISM: Artificial Sequence
<220> FEATURE:
<223> OTHER INFORMATION: For general cloning and sequencing

<400> SEQUENCE: 3
ttaccctgtt tcgggccc                                                 18

<210> SEQ ID NO 4
<211> LENGTH: 21
<212> TYPE: DNA
<213> ORGANISM: Artificial Sequence
<220> FEATURE:
<223> OTHER INFORMATION: For general cloning and sequencing

<400> SEQUENCE: 4
gcttcccaac cttaccagag g                                             21

<210> SEQ ID NO 5
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 5
cggtttgact cacggggat                                                19

<210> SEQ ID NO 6
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 6
ggcaaacaac agatggctgg                                               20

<210> SEQ ID NO 7
<211> LENGTH: 19
<212> TYPE: DNA
<213> ORGANISM: Artificial Sequence

```
<220> FEATURE:
<223> OTHER INFORMATION: For general cloning and sequencing

<400> SEQUENCE: 7
cttttcgggg aaatgtgcg                                                    19

<210> SEQ ID NO 8
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 8
tgagaaagcg ccacgcttc                                                    19

<210> SEQ ID NO 9
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 9
gtgagcgcgc gtaatacga                                                    19

<210> SEQ ID NO 10
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 10
aggcacccca ggctttacac                                                   20

<210> SEQ ID NO 11
<211> LENGTH: 22
<212> TYPE: DNA
<213> ORGANISM: Artificial Sequence
<220> FEATURE:
<223> OTHER INFORMATION: For general cloning and sequencing

<400> SEQUENCE: 11
caaggtgaac ttcaagatcc gc                                                22

<210> SEQ ID NO 12
<211> LENGTH: 27
<212> TYPE: DNA
<213> ORGANISM: Artificial Sequence
<220> FEATURE:
<223> OTHER INFORMATION: For general cloning and sequencing

<400> SEQUENCE: 12
attgcattca ttttatgttt caggttc                                           27

<210> SEQ ID NO 13
<211> LENGTH: 18
<212> TYPE: DNA
<213> ORGANISM: Artificial Sequence
<220> FEATURE:
<223> OTHER INFORMATION: For general cloning and sequencing

<400> SEQUENCE: 13
gacgcaaatg ggcggtag                                                     18
```

<210> SEQ ID NO 14
<211> LENGTH: 21
<212> TYPE: DNA
<213> ORGANISM: Artificial Sequence
<220> FEATURE:
<223> OTHER INFORMATION: For general cloning and sequencing

<400> SEQUENCE: 14
gtgaaccgtc agatcgctag c                                              21

<210> SEQ ID NO 15
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 15
cacagggtga gatatcggcc                                                20

<210> SEQ ID NO 16
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 16
aggctccata ccgacgatct                                                20

<210> SEQ ID NO 17
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 17
cgggcgattg gtcgtaatcc                                                20

<210> SEQ ID NO 18
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 18
tgtctcgaca agcccagtt                                                 19

<210> SEQ ID NO 19
<211> LENGTH: 16
<212> TYPE: DNA
<213> ORGANISM: Artificial Sequence
<220> FEATURE:
<223> OTHER INFORMATION: For general cloning and sequencing

<400> SEQUENCE: 19
caatggggcg gagttg                                                    16

<210> SEQ ID NO 20
<211> LENGTH: 21
<212> TYPE: DNA
<213> ORGANISM: Artificial Sequence
<220> FEATURE:
<223> OTHER INFORMATION: For general cloning and sequencing

<400> SEQUENCE: 20
ccattgacgt caatggggtg g                                              21

<210> SEQ ID NO 21
<211> LENGTH: 15
<212> TYPE: DNA
<213> ORGANISM: Artificial Sequence
<220> FEATURE:
<223> OTHER INFORMATION: For general cloning and sequencing

<400> SEQUENCE: 21
acctggcgcg cacgt                                                     15

<210> SEQ ID NO 22
<211> LENGTH: 21
<212> TYPE: DNA
<213> ORGANISM: Artificial Sequence
<220> FEATURE:
<223> OTHER INFORMATION: For general cloning and sequencing

<400> SEQUENCE: 22
ccagcatgcc tgctattgtc t                                              21

<210> SEQ ID NO 23
<211> LENGTH: 24
<212> TYPE: DNA
<213> ORGANISM: Artificial Sequence
<220> FEATURE:
<223> OTHER INFORMATION: For general cloning and sequencing

<400> SEQUENCE: 23
tcagatcgct agcacctctc taaa                                           24

<210> SEQ ID NO 24
<211> LENGTH: 34
<212> TYPE: DNA
<213> ORGANISM: Artificial Sequence
<220> FEATURE:
<223> OTHER INFORMATION: For general cloning and sequencing

<400> SEQUENCE: 24
aaaaaacgat cggcagacaa cccaggccca ggcc                                34

<210> SEQ ID NO 25
<211> LENGTH: 49
<212> TYPE: DNA
<213> ORGANISM: Artificial Sequence
<220> FEATURE:
<223> OTHER INFORMATION: For general cloning and sequencing

<400> SEQUENCE: 25
cctggcgcgc acgtttgcgc gggagatggg ggaggcgaac tgatacacg                49

<210> SEQ ID NO 26
<211> LENGTH: 49
<212> TYPE: DNA
<213> ORGANISM: Artificial Sequence
<220> FEATURE:
<223> OTHER INFORMATION: For general cloning and sequencing

<400> SEQUENCE: 26
ggaggcgaac tgatacacgg catagctttc attttttgtct tttttaac                49

<210> SEQ ID NO 27

```
<211> LENGTH: 17
<212> TYPE: DNA
<213> ORGANISM: Artificial Sequence
<220> FEATURE:
<223> OTHER INFORMATION: For general cloning and sequencing

<400> SEQUENCE: 27
gaaggagggg tacccccc                                                 17

<210> SEQ ID NO 28
<211> LENGTH: 32
<212> TYPE: DNA
<213> ORGANISM: Artificial Sequence
<220> FEATURE:
<223> OTHER INFORMATION: For general cloning and sequencing

<400> SEQUENCE: 28
ctagacataa gcttatggct tcgtacccct gc                                 32

<210> SEQ ID NO 29
<211> LENGTH: 30
<212> TYPE: DNA
<213> ORGANISM: Artificial Sequence
<220> FEATURE:
<223> OTHER INFORMATION: For general cloning and sequencing

<400> SEQUENCE: 29
actgatctgg tacctcagtt cgcctccccc                                    30

<210> SEQ ID NO 30
<211> LENGTH: 45
<212> TYPE: DNA
<213> ORGANISM: Artificial Sequence
<220> FEATURE:
<223> OTHER INFORMATION: For general cloning and sequencing

<400> SEQUENCE: 30
ctcataccac atttcagaca taaatacatc cccacagcct aaggc                   45

<210> SEQ ID NO 31
<211> LENGTH: 49
<212> TYPE: DNA
<213> ORGANISM: Artificial Sequence
<220> FEATURE:
<223> OTHER INFORMATION: For general cloning and sequencing

<400> SEQUENCE: 31
atacatatac acacacacac acactcatac cacatttcag acataaatg               49

<210> SEQ ID NO 32
<211> LENGTH: 47
<212> TYPE: DNA
<213> ORGANISM: Artificial Sequence
<220> FEATURE:
<223> OTHER INFORMATION: For general cloning and sequencing

<400> SEQUENCE: 32
cctcctcctc ctcctcctat atacatatac acacacacac acactca                 47

<210> SEQ ID NO 33
<211> LENGTH: 46
<212> TYPE: DNA
<213> ORGANISM: Artificial Sequence
<220> FEATURE:
<223> OTHER INFORMATION: For general cloning and sequencing

<400> SEQUENCE: 33
```

```
tgggggtacc cctccttcct cctcctcctc ctcctcctcc tatata           46
```

<210> SEQ ID NO 34
<211> LENGTH: 24
<212> TYPE: DNA
<213> ORGANISM: Artificial Sequence
<220> FEATURE:
<223> OTHER INFORMATION: For general cloning and sequencing

<400> SEQUENCE: 34

```
taaacaagtt gctgaggcta tctc                                   24
```

<210> SEQ ID NO 35
<211> LENGTH: 19
<212> TYPE: DNA
<213> ORGANISM: Artificial Sequence
<220> FEATURE:
<223> OTHER INFORMATION: CTAGCGGATCCAAGCTTCC  5'PO4

<400> SEQUENCE: 35

```
ctagcggatc caagcttcc                                         19
```

<210> SEQ ID NO 36
<211> LENGTH: 18
<212> TYPE: DNA
<213> ORGANISM: Artificial Sequence
<220> FEATURE:
<223> OTHER INFORMATION: TGAGGAAGCTTGGATCCG  5'PO4

<400> SEQUENCE: 36

```
tgaggaagct tggatccg                                          18
```

<210> SEQ ID NO 37
<211> LENGTH: 18
<212> TYPE: DNA
<213> ORGANISM: Artificial Sequence
<220> FEATURE:
<223> OTHER INFORMATION: For general cloning and sequencing

<400> SEQUENCE: 37

```
cgcagacgcg tgttgatg                                          18
```

<210> SEQ ID NO 38
<211> LENGTH: 66
<212> TYPE: DNA
<213> ORGANISM: Artificial Sequence
<220> FEATURE:
<223> OTHER INFORMATION: For general cloning and sequencing

<400> SEQUENCE: 38

```
tcagatcgct agcctggaaa aaatcggaaa aaaaacctct ctaaacctaa attaaatttt   60
cttctc                                                             66
```

<210> SEQ ID NO 39
<211> LENGTH: 23
<212> TYPE: DNA
<213> ORGANISM: Artificial Sequence
<220> FEATURE:
<223> OTHER INFORMATION: For general cloning and sequencing

<400> SEQUENCE: 39

```
catgccttat gccgtgaccg acg                                    23
```

<210> SEQ ID NO 40

```
<211> LENGTH: 26
<212> TYPE: DNA
<213> ORGANISM: Artificial Sequence
<220> FEATURE:
<223> OTHER INFORMATION: For general cloning and sequencing

<400> SEQUENCE: 40
cttgcacaca aaagcccac tccagc                                              26

<210> SEQ ID NO 41
<211> LENGTH: 28
<212> TYPE: DNA
<213> ORGANISM: Artificial Sequence
<220> FEATURE:
<223> OTHER INFORMATION: For general cloning and sequencing

<400> SEQUENCE: 41
cctacaattc ttctttgggc tgctcgct                                           28

<210> SEQ ID NO 42
<211> LENGTH: 21
<212> TYPE: DNA
<213> ORGANISM: Artificial Sequence
<220> FEATURE:
<223> OTHER INFORMATION: For general cloning and sequencing

<400> SEQUENCE: 42
cccctgccat caacacgcgt c                                                  21

<210> SEQ ID NO 43
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 43
cgacctggcg cgcacgttt                                                     19

<210> SEQ ID NO 44
<211> LENGTH: 23
<212> TYPE: DNA
<213> ORGANISM: Artificial Sequence
<220> FEATURE:
<223> OTHER INFORMATION: For general cloning and sequencing

<400> SEQUENCE: 44
gacatccact ttgcctttct ctc                                                23

<210> SEQ ID NO 45
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 45
aagcgcccag ataacaatgg                                                    20

<210> SEQ ID NO 46
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 46
```

-continued gcctcgacca gggtgagat                                                    19

<210> SEQ ID NO 47
<211> LENGTH: 18
<212> TYPE: DNA
<213> ORGANISM: Artificial Sequence
<220> FEATURE:
<223> OTHER INFORMATION: For general cloning and sequencing

<400> SEQUENCE: 47
ctcatatcgg gggggagg                                                     18

<210> SEQ ID NO 48
<211> LENGTH: 27
<212> TYPE: DNA
<213> ORGANISM: Artificial Sequence
<220> FEATURE:
<223> OTHER INFORMATION: For general cloning and sequencing

<400> SEQUENCE: 48
ttattcactc acctggtttt ctaaaca                                           27

<210> SEQ ID NO 49
<211> LENGTH: 24
<212> TYPE: DNA
<213> ORGANISM: Artificial Sequence
<220> FEATURE:
<223> OTHER INFORMATION: For general cloning and sequencing

<400> SEQUENCE: 49
gtaaatttgt ctggcacaga tgca                                              24

<210> SEQ ID NO 50
<211> LENGTH: 27
<212> TYPE: DNA
<213> ORGANISM: Artificial Sequence
<220> FEATURE:
<223> OTHER INFORMATION: For general cloning and sequencing

<400> SEQUENCE: 50
aagtgaagag ggaagacata actgttt                                           27

<210> SEQ ID NO 51
<211> LENGTH: 22
<212> TYPE: DNA
<213> ORGANISM: Artificial Sequence
<220> FEATURE:
<223> OTHER INFORMATION: For general cloning and sequencing

<400> SEQUENCE: 51
gaacttggaa aagtgggatc ga                                                22

<210> SEQ ID NO 52
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 52
catagcgagc agcccaaag                                                    19

<210> SEQ ID NO 53
<211> LENGTH: 18
<212> TYPE: DNA

```
<213> ORGANISM: Artificial Sequence
<220> FEATURE:
<223> OTHER INFORMATION: For general cloning and sequencing

<400> SEQUENCE: 53 gatggggag gcgaactg                                                          18

<210> SEQ ID NO 54
<211> LENGTH: 25
<212> TYPE: DNA
<213> ORGANISM: Artificial Sequence
<220> FEATURE:
<223> OTHER INFORMATION: For general cloning and sequencing

<400> SEQUENCE: 54
agtcttcagg gtgtttagaa aacca                                                 25

<210> SEQ ID NO 55
<211> LENGTH: 21
<212> TYPE: DNA
<213> ORGANISM: Artificial Sequence
<220> FEATURE:
<223> OTHER INFORMATION: For general cloning and sequencing

<400> SEQUENCE: 55
aaggcatccc ttcctgtatg c                                                     21

<210> SEQ ID NO 56
<211> LENGTH: 29
<212> TYPE: DNA
<213> ORGANISM: Artificial Sequence
<220> FEATURE:
<223> OTHER INFORMATION: For general cloning and sequencing

<400> SEQUENCE: 56
aagctgcttt ctcttaattc ttttgtaac                                             29

<210> SEQ ID NO 57
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 57
caggctccat accgacgatc                                                       20

<210> SEQ ID NO 58
<211> LENGTH: 22
<212> TYPE: DNA
<213> ORGANISM: Artificial Sequence
<220> FEATURE:
<223> OTHER INFORMATION: For general cloning and sequencing

<400> SEQUENCE: 58
ttctcatggc aaagttcttc ca                                                    22

<210> SEQ ID NO 59
<211> LENGTH: 22
<212> TYPE: DNA
<213> ORGANISM: Artificial Sequence
<220> FEATURE:
<223> OTHER INFORMATION: For general cloning and sequencing

<400> SEQUENCE: 59
catcttgctg caaagctgaa aa                                                    22
```

<210> SEQ ID NO 60
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 60
ttgctgtgtc cccgtgatc                                                19

<210> SEQ ID NO 61
<211> LENGTH: 26
<212> TYPE: DNA
<213> ORGANISM: Artificial Sequence
<220> FEATURE:
<223> OTHER INFORMATION: For general cloning and sequencing

<400> SEQUENCE: 61
cgtttaaact taagcttatg gcttcg                                        26

<210> SEQ ID NO 62
<211> LENGTH: 18
<212> TYPE: DNA
<213> ORGANISM: Artificial Sequence
<220> FEATURE:
<223> OTHER INFORMATION: For general cloning and sequencing

<400> SEQUENCE: 62
cagttcgcct cccccatc                                                 18

<210> SEQ ID NO 63
<211> LENGTH: 14
<212> TYPE: DNA
<213> ORGANISM: Artificial Sequence
<220> FEATURE:
<223> OTHER INFORMATION: For general cloning and sequencing

<400> SEQUENCE: 63
tcgcactgga tacg                                                     14

<210> SEQ ID NO 64
<211> LENGTH: 26
<212> TYPE: DNA
<213> ORGANISM: Artificial Sequence
<220> FEATURE:
<223> OTHER INFORMATION: For general cloning and sequencing

<400> SEQUENCE: 64
acacacacac acactcatac cacatt                                        26

<210> SEQ ID NO 65
<211> LENGTH: 50
<212> TYPE: DNA
<213> ORGANISM: Artificial Sequence
<220> FEATURE:
<223> OTHER INFORMATION: For general cloning and sequencing

<400> SEQUENCE: 65
gtcgtatcca gtgcagggtc cgaggtattc gcactggata cgacacattt              50

<210> SEQ ID NO 66
<211> LENGTH: 50
<212> TYPE: DNA
<213> ORGANISM: Artificial Sequence
<220> FEATURE:

<223> OTHER INFORMATION: For general cloning and sequencing

<400> SEQUENCE: 66
gtcgtatcca gtgcagggtc cgaggtattc gcactggata cgacggtatt      50

<210> SEQ ID NO 67
<211> LENGTH: 18
<212> TYPE: DNA
<213> ORGANISM: Artificial Sequence
<220> FEATURE:
<223> OTHER INFORMATION: For general cloning and sequencing

<400> SEQUENCE: 67
cagtgcaggg tccgaggt      18

<210> SEQ ID NO 68
<211> LENGTH: 24
<212> TYPE: DNA
<213> ORGANISM: Artificial Sequence
<220> FEATURE:
<223> OTHER INFORMATION: For general cloning and sequencing

<400> SEQUENCE: 68
ccctcttcct cacttccctg tact      24

<210> SEQ ID NO 69
<211> LENGTH: 23
<212> TYPE: DNA
<213> ORGANISM: Artificial Sequence
<220> FEATURE:
<223> OTHER INFORMATION: For general cloning and sequencing

<400> SEQUENCE: 69
catcagctca tttgcttcct ttt      23

<210> SEQ ID NO 70
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 70
gacatgggca gagcaatggt      20

<210> SEQ ID NO 71
<211> LENGTH: 26
<212> TYPE: DNA
<213> ORGANISM: Artificial Sequence
<220> FEATURE:
<223> OTHER INFORMATION: For general cloning and sequencing

<400> SEQUENCE: 71
actctgggag gagttacttg aagttc      26

<210> SEQ ID NO 72
<211> LENGTH: 21
<212> TYPE: DNA
<213> ORGANISM: Artificial Sequence
<220> FEATURE:
<223> OTHER INFORMATION: For general cloning and sequencing

<400> SEQUENCE: 72
agaaggagga gggcagaatc a      21

```
<210> SEQ ID NO 73
<211> LENGTH: 21
<212> TYPE: DNA
<213> ORGANISM: Artificial Sequence
<220> FEATURE:
<223> OTHER INFORMATION: For general cloning and sequencing

<400> SEQUENCE: 73
agctgcgctg atagacatcc a                                        21

<210> SEQ ID NO 74
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 74
tttgggctgc tcgctatga                                           19

<210> SEQ ID NO 75
<211> LENGTH: 22
<212> TYPE: DNA
<213> ORGANISM: Artificial Sequence
<220> FEATURE:
<223> OTHER INFORMATION: For general cloning and sequencing

<400> SEQUENCE: 75
ttgtttggaa gcattcaact gc                                       22

<210> SEQ ID NO 76
<211> LENGTH: 28
<212> TYPE: DNA
<213> ORGANISM: Artificial Sequence
<220> FEATURE:
<223> OTHER INFORMATION: For general cloning and sequencing

<400> SEQUENCE: 76
gactacagta ctggttcaga tatccacg                                 28

<210> SEQ ID NO 77
<211> LENGTH: 18
<212> TYPE: DNA
<213> ORGANISM: Artificial Sequence
<220> FEATURE:
<223> OTHER INFORMATION: For general cloning and sequencing

<400> SEQUENCE: 77
gcatcctgct agacgcgc                                            18

<210> SEQ ID NO 78
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 78
tgcgtgggta ggagcagtg                                           19

<210> SEQ ID NO 79
<211> LENGTH: 15
<212> TYPE: DNA
<213> ORGANISM: Artificial Sequence
<220> FEATURE:
<223> OTHER INFORMATION: For general cloning and sequencing
```

<400> SEQUENCE: 79
gcgccagggc ctcac        15

<210> SEQ ID NO 80
<211> LENGTH: 25
<212> TYPE: DNA
<213> ORGANISM: Artificial Sequence
<220> FEATURE:
<223> OTHER INFORMATION: For general cloning and sequencing

<400> SEQUENCE: 80
ctaggaaaat gctgtgaaga gatcc        25

<210> SEQ ID NO 81
<211> LENGTH: 17
<212> TYPE: DNA
<213> ORGANISM: Artificial Sequence
<220> FEATURE:
<223> OTHER INFORMATION: For general cloning and sequencing

<400> SEQUENCE: 81
ccagaatggg agccggt        17

<210> SEQ ID NO 82
<211> LENGTH: 23
<212> TYPE: DNA
<213> ORGANISM: Artificial Sequence
<220> FEATURE:
<223> OTHER INFORMATION: For general cloning and sequencing

<400> SEQUENCE: 82
ttctgcctcc tacagacttc gag        23

<210> SEQ ID NO 83
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 83
tacgtggcct tcacggaca        19

<210> SEQ ID NO 84
<211> LENGTH: 18
<212> TYPE: DNA
<213> ORGANISM: Artificial Sequence
<220> FEATURE:
<223> OTHER INFORMATION: For general cloning and sequencing

<400> SEQUENCE: 84
aacttgcggc caatcagc        18

<210> SEQ ID NO 85
<211> LENGTH: 23
<212> TYPE: DNA
<213> ORGANISM: Artificial Sequence
<220> FEATURE:
<223> OTHER INFORMATION: For general cloning and sequencing

<400> SEQUENCE: 85
tcctgtgtct tggaactgga act        23

<210> SEQ ID NO 86
<211> LENGTH: 19

```
<212> TYPE: DNA
<213> ORGANISM: Artificial Sequence
<220> FEATURE:
<223> OTHER INFORMATION: For general cloning and sequencing

<400> SEQUENCE: 86
cttccggaga gctgttccc                                                      19

<210> SEQ ID NO 87
<211> LENGTH: 28
<212> TYPE: DNA
<213> ORGANISM: Artificial Sequence
<220> FEATURE:
<223> OTHER INFORMATION: For general cloning and sequencing

<400> SEQUENCE: 87
ccagatccaa agagataaca gagtaacc                                             28

<210> SEQ ID NO 88
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 88
caaggacctc ggctggaag                                                      19

<210> SEQ ID NO 89
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 89
tgctgtactg cgtgtccagg                                                     20

<210> SEQ ID NO 90
<211> LENGTH: 18
<212> TYPE: DNA
<213> ORGANISM: Artificial Sequence
<220> FEATURE:
<223> OTHER INFORMATION: For general cloning and sequencing

<400> SEQUENCE: 90
gcatctcgta gcccggtg                                                       18

<210> SEQ ID NO 91
<211> LENGTH: 25
<212> TYPE: DNA
<213> ORGANISM: Artificial Sequence
<220> FEATURE:
<223> OTHER INFORMATION: For general cloning and sequencing

<400> SEQUENCE: 91
agtacatctt caagccatcc tgtgt                                               25

<210> SEQ ID NO 92
<211> LENGTH: 22
<212> TYPE: DNA
<213> ORGANISM: Artificial Sequence
<220> FEATURE:
<223> OTHER INFORMATION: For general cloning and sequencing

<400> SEQUENCE: 92
```
ggtgatgttg gactcctcag tg                                            22

<210> SEQ ID NO 93
<211> LENGTH: 18
<212> TYPE: DNA
<213> ORGANISM: Artificial Sequence
<220> FEATURE:
<223> OTHER INFORMATION: For general cloning and sequencing

<400> SEQUENCE: 93
ttgccccact tcccaaag                                                 18

<210> SEQ ID NO 94
<211> LENGTH: 17
<212> TYPE: DNA
<213> ORGANISM: Artificial Sequence
<220> FEATURE:
<223> OTHER INFORMATION: For general cloning and sequencing

<400> SEQUENCE: 94
cggacgccac ctgtcac                                                  17

<210> SEQ ID NO 95
<211> LENGTH: 18
<212> TYPE: DNA
<213> ORGANISM: Artificial Sequence
<220> FEATURE:
<223> OTHER INFORMATION: For general cloning and sequencing

<400> SEQUENCE: 95
tggcacggga gtttctgg                                                 18

<210> SEQ ID NO 96
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 96
tagcgcgctc agggtacag                                                19

<210> SEQ ID NO 97
<211> LENGTH: 26
<212> TYPE: DNA
<213> ORGANISM: Artificial Sequence
<220> FEATURE:
<223> OTHER INFORMATION: For general cloning and sequencing

<400> SEQUENCE: 97
ggaagctgtt gataccaaaa ataatg                                        26

<210> SEQ ID NO 98
<211> LENGTH: 24
<212> TYPE: DNA
<213> ORGANISM: Artificial Sequence
<220> FEATURE:
<223> OTHER INFORMATION: For general cloning and sequencing

<400> SEQUENCE: 98
gataagtgcg tgtcttcaag tcgt                                          24

<210> SEQ ID NO 99
<211> LENGTH: 25
<212> TYPE: DNA
<213> ORGANISM: Artificial Sequence

```
<220> FEATURE:
<223> OTHER INFORMATION: For general cloning and sequencing

<400> SEQUENCE: 99
ttgccaatcc agtaatttca ggtag                                              25

<210> SEQ ID NO 100
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 100
ggtcctggtg ctggtcattg                                                    20

<210> SEQ ID NO 101
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 101
tcccaatctt cgagcactgc                                                    20

<210> SEQ ID NO 102
<211> LENGTH: 17
<212> TYPE: DNA
<213> ORGANISM: Artificial Sequence
<220> FEATURE:
<223> OTHER INFORMATION: For general cloning and sequencing

<400> SEQUENCE: 102
atgtcccatg ccctgcc                                                       17

<210> SEQ ID NO 103
<211> LENGTH: 19
<212> TYPE: DNA
<213> ORGANISM: Artificial Sequence
<220> FEATURE:
<223> OTHER INFORMATION: For general cloning and sequencing

<400> SEQUENCE: 103
caggctgccc tgtcagtga                                                     19

<210> SEQ ID NO 104
<211> LENGTH: 17
<212> TYPE: DNA
<213> ORGANISM: Artificial Sequence
<220> FEATURE:
<223> OTHER INFORMATION: For general cloning and sequencing

<400> SEQUENCE: 104
ccggcagctt cctgctc                                                       17

<210> SEQ ID NO 105
<211> LENGTH: 20
<212> TYPE: DNA
<213> ORGANISM: Artificial Sequence
<220> FEATURE:
<223> OTHER INFORMATION: For general cloning and sequencing

<400> SEQUENCE: 105
gtctggtgga agggagtcca                                                    20
```

<210> SEQ ID NO 106
<211> LENGTH: 24
<212> TYPE: DNA
<213> ORGANISM: Artificial Sequence
<220> FEATURE:
<223> OTHER INFORMATION: For general cloning and sequencing

<400> SEQUENCE: 106
ttgataaagc aagaaaacaa tgcc                                          24

<210> SEQ ID NO 107
<211> LENGTH: 27
<212> TYPE: DNA
<213> ORGANISM: Artificial Sequence
<220> FEATURE:
<223> OTHER INFORMATION: For general cloning and sequencing

<400> SEQUENCE: 107
tttgttttca tagaggtcaa attcatg                                       27

<210> SEQ ID NO 108
<211> LENGTH: 30
<212> TYPE: DNA
<213> ORGANISM: Artificial Sequence
<220> FEATURE:
<223> OTHER INFORMATION: For general cloning and sequencing

<400> SEQUENCE: 108
ttatgcaata tttagggaga agtcagttac                                    30

<210> SEQ ID NO 109
<211> LENGTH: 87
<212> TYPE: DNA
<213> ORGANISM: Artificial Sequence
<220> FEATURE:
<223> OTHER INFORMATION: For general cloning and sequencing

<400> SEQUENCE: 109
gctagcacct ctctaaacct aaattaaatt ttcttctcta aacctctttc ctagttggac   60
tgacgtcact cagtcctcct cctcagc                                       87

<210> SEQ ID NO 110
<211> LENGTH: 87
<212> TYPE: DNA
<213> ORGANISM: Artificial Sequence
<220> FEATURE:
<223> OTHER INFORMATION: For general cloning and sequencing

<400> SEQUENCE: 110
gctagcacct ctctaaacct aaaaaaaatt ttcttctcta aacctctttc ctagttggac   60
tgacgtcact cagtcctcct cctcagc                                       87

<210> SEQ ID NO 111
<211> LENGTH: 80
<212> TYPE: DNA
<213> ORGANISM: Artificial Sequence
<220> FEATURE:
<223> OTHER INFORMATION: For general cloning and sequencing

<400> SEQUENCE: 111
gctagcggac tgcttgaagc aagtagttaa tggtggatat tattctaccg gactgacgtc   60
actcagtcct cctcctcagc                                               80

```
<210> SEQ ID NO 112
<211> LENGTH: 87
<212> TYPE: DNA
<213> ORGANISM: Artificial Sequence
<220> FEATURE:
<223> OTHER INFORMATION: For general cloning and sequencing

<400> SEQUENCE: 112
gctagccttc tcagttacaa aaaatacgat gttatcacgg cttgacactg agagtaggac    60
tgacgtcact cagtcctcct cctcagc                                       87

<210> SEQ ID NO 113
<211> LENGTH: 107
<212> TYPE: DNA
<213> ORGANISM: Artificial Sequence
<220> FEATURE:
<223> OTHER INFORMATION: For general cloning and sequencing

<400> SEQUENCE: 113
gctagcacct ctctaaacct aaattaaatt ttcttctcta aacctctttc ctagttaact    60
aggaaagagg ttagagagaa atttaattag gttgagaggt cctcagc                 107

<210> SEQ ID NO 114
<211> LENGTH: 80
<212> TYPE: DNA
<213> ORGANISM: Artificial Sequence
<220> FEATURE:
<223> OTHER INFORMATION: For general cloning and sequencing

<400> SEQUENCE: 114
gctagcggac tgctggtagc aagtagttaa tggtggatat tattctaccg gactgacgtc    60
actcagtcct cctcctcagc                                               80

<210> SEQ ID NO 115
<211> LENGTH: 87
<212> TYPE: DNA
<213> ORGANISM: Artificial Sequence
<220> FEATURE:
<223> OTHER INFORMATION: For general cloning and sequencing

<400> SEQUENCE: 115
gctagccttc tcagttacaa aaaatacgat tgtatcacgg cttgacactg agagtaggac    60
tgacgtcact cagtcctcct cctcagc                                       87

<210> SEQ ID NO 116
<211> LENGTH: 107
<212> TYPE: DNA
<213> ORGANISM: Artificial Sequence
<220> FEATURE:
<223> OTHER INFORMATION: For general cloning and sequencing

<400> SEQUENCE: 116
gctagcacct ctctaaacct aaaaaaaatt ttcttctcta aacctctttc ctagttaact    60
aggaaagagg ttagagagaa atttatttag gttgagaggt cctcagc                 107

<210> SEQ ID NO 117
<211> LENGTH: 87
<212> TYPE: DNA
<213> ORGANISM: Artificial Sequence
<220> FEATURE:
<223> OTHER INFORMATION: For general cloning and sequencing

<400> SEQUENCE: 117
```

```
ggtacccctc cttcctcctc ctcctcctcc tcctcctata tacatataca cacacacaca    60
cactcatacc acatttcaga cataaat                                        87

<210> SEQ ID NO 118
<211> LENGTH: 87
<212> TYPE: DNA
<213> ORGANISM: Artificial Sequence
<220> FEATURE:
<223> OTHER INFORMATION: For general cloning and sequencing

<400> SEQUENCE: 118
ggtacccctc cttcctcctc ctcctcctcc tcctcctata tacatataca cacacacaca    60
cagacatacc acatttcaga cataaat                                        87

<210> SEQ ID NO 119
<211> LENGTH: 102
<212> TYPE: DNA
<213> ORGANISM: Artificial Sequence
<220> FEATURE:
<223> OTHER INFORMATION: For general cloning and sequencing

<400> SEQUENCE: 119
ggtacccctc cttcctcctc ctcctcctcc tcctcctgat gtaacttttg gaattgcaaa    60
tacatatgta tatattatgt aatatacata catatataca ta                      102

<210> SEQ ID NO 120
<211> LENGTH: 94
<212> TYPE: DNA
<213> ORGANISM: Artificial Sequence
<220> FEATURE:
<223> OTHER INFORMATION: For general cloning and sequencing

<400> SEQUENCE: 120
ggtaccctga aatgtgtaga ttgtgtgtgt ggtgtatatg taatatatac atatacacac    60
acacacacac tcataccaca tttcagacat aaat                                94

<210> SEQ ID NO 121
<211> LENGTH: 102
<212> TYPE: DNA
<213> ORGANISM: Artificial Sequence
<220> FEATURE:
<223> OTHER INFORMATION: For general cloning and sequencing

<400> SEQUENCE: 121
ggtacccctc cttcctcctc ctcctcctcc tcctcctgat gtaacttttg gaattgcaaa    60
tacatatgta tatattatgg tatatacata catatataca ta                      102

<210> SEQ ID NO 122
<211> LENGTH: 94
<212> TYPE: DNA
<213> ORGANISM: Artificial Sequence
<220> FEATURE:
<223> OTHER INFORMATION: For general cloning and sequencing

<400> SEQUENCE: 122
ggtaccctga aatgtgtaga ttgtgtgtgt ggtgtatatg taatatatac atatacacac    60
acacacacag acataccaca tttcagacat aaat                                94

<210> SEQ ID NO 123
<211> LENGTH: 98
<212> TYPE: DNA
<213> ORGANISM: Artificial Sequence
```

```
<220> FEATURE:
<223> OTHER INFORMATION: For general cloning and sequencing

<400> SEQUENCE: 123
ggtacccctc cttcctcctc ctcctcctcc tcctcctata tacatataca cacacacaca    60
cactcatacc acatttcatg aaatgtggtg acataaat                            98

<210> SEQ ID NO 124
<211> LENGTH: 194
<212> TYPE: DNA
<213> ORGANISM: Artificial Sequence
<220> FEATURE:
<223> OTHER INFORMATION: For general cloning and sequencing

<400> SEQUENCE: 124
ggtacccctc cttcctcctc ctcctcctcc tcctcctata tacatataca cacacacaca    60
cactcatacc acatttcaga cataaatgcg tagataataa ccagtgaact tagcgtgcat   120
gaaaacatgc acgctgaatc gtagaaaaaa atctacgatt caagttcact ggaatttatc   180
tacgcgacat aaat                                                    194

<210> SEQ ID NO 125
<211> LENGTH: 50
<212> TYPE: DNA
<213> ORGANISM: Artificial Sequence
<220> FEATURE:
<223> OTHER INFORMATION: For general cloning and sequencing

<400> SEQUENCE: 125
aacagttcct ttatacaaat tcaccagatg atacaaaaca tattttttta              50

<210> SEQ ID NO 126
<211> LENGTH: 50
<212> TYPE: DNA
<213> ORGANISM: Artificial Sequence
<220> FEATURE:
<223> OTHER INFORMATION: For general cloning and sequencing

<400> SEQUENCE: 126
gatctaaaga tcctctacac caacaaaatt attatgttta ttaaactgac              50

<210> SEQ ID NO 127
<211> LENGTH: 50
<212> TYPE: DNA
<213> ORGANISM: Artificial Sequence
<220> FEATURE:
<223> OTHER INFORMATION: For general cloning and sequencing

<400> SEQUENCE: 127
tttctttctt gatccttata ttcctgtgcc cctttcctt cctccccaca               50

<210> SEQ ID NO 128
<211> LENGTH: 50
<212> TYPE: RNA
<213> ORGANISM: Artificial Sequence
<220> FEATURE:
<223> OTHER INFORMATION: For general cloning and sequencing

<400> SEQUENCE: 128
aacuaggaaa gagguuuaga gaagaaaauu uuuuuaggu uuagagaggu                50

<210> SEQ ID NO 129
<211> LENGTH: 50
<212> TYPE: RNA
```

-continued

<213> ORGANISM: Artificial Sequence
<220> FEATURE:
<223> OTHER INFORMATION: For general cloning and sequencing

<400> SEQUENCE: 129
accucucuaa accuaaauua aauuuucuuc ucuaaaccuc uuuccaguu            50

<210> SEQ ID NO 130
<211> LENGTH: 50
<212> TYPE: RNA
<213> ORGANISM: Artificial Sequence
<220> FEATURE:
<223> OTHER INFORMATION: For general cloning and sequencing

<400> SEQUENCE: 130
accucucuaa accuaaaaaa aauuuucuuc ucuaaaccuc uuuccaguu            50

<210> SEQ ID NO 131
<211> LENGTH: 50
<212> TYPE: RNA
<213> ORGANISM: Artificial Sequence
<220> FEATURE:
<223> OTHER INFORMATION: For general cloning and sequencing

<400> SEQUENCE: 131
auuuaugucu gaaauguggu augucugugu gugugugugu auauguauau            50

<210> SEQ ID NO 132
<211> LENGTH: 50
<212> TYPE: RNA
<213> ORGANISM: Artificial Sequence
<220> FEATURE:
<223> OTHER INFORMATION: For general cloning and sequencing

<400> SEQUENCE: 132
auauacauau acacacacac acacacucau accacauuuc agacauaaau            50

<210> SEQ ID NO 133
<211> LENGTH: 50
<212> TYPE: RNA
<213> ORGANISM: Artificial Sequence
<220> FEATURE:
<223> OTHER INFORMATION: For general cloning and sequencing

<400> SEQUENCE: 133
auauacauau acacacacac acacagacau accacauuuc agacauaaau            50

<210> SEQ ID NO 134
<211> LENGTH: 50
<212> TYPE: RNA
<213> ORGANISM: Artificial Sequence
<220> FEATURE:
<223> OTHER INFORMATION: For general cloning and sequencing

<400> SEQUENCE: 134
accucucuaa accuaaauua aauuuucuuc ucuaaaccuc uuuccaguu            50

<210> SEQ ID NO 135
<211> LENGTH: 50
<212> TYPE: RNA
<213> ORGANISM: Artificial Sequence
<220> FEATURE:
<223> OTHER INFORMATION: For general cloning and sequencing

<400> SEQUENCE: 135
accucucuaa accuaaaaaa aauuuucuuc ucuaaaccuc uuuccaguu            50

<210> SEQ ID NO 136
<211> LENGTH: 43
<212> TYPE: RNA
<213> ORGANISM: Artificial Sequence
<220> FEATURE:
<223> OTHER INFORMATION: For general cloning and sequencing

<400> SEQUENCE: 136
ggacugcuug aagcaaguag uuaauggugg auauuauucu acc        43

<210> SEQ ID NO 137
<211> LENGTH: 50
<212> TYPE: RNA
<213> ORGANISM: Artificial Sequence
<220> FEATURE:
<223> OTHER INFORMATION: For general cloning and sequencing

<400> SEQUENCE: 137
cuucucaguu acaaaaaaua cgauguuauc acggcuugac acugagagua        50

<210> SEQ ID NO 138
<211> LENGTH: 94
<212> TYPE: RNA
<213> ORGANISM: Artificial Sequence
<220> FEATURE:
<223> OTHER INFORMATION: For general cloning and sequencing

<400> SEQUENCE: 138
accucucuaa accuaaauua aauuuucuuc ucuaaaccuc uuccuaguu aacuaggaaa        60 gagguuagag agaaauuuaa uuagguugag aggu        94

<210> SEQ ID NO 139
<211> LENGTH: 94
<212> TYPE: RNA
<213> ORGANISM: Artificial Sequence
<220> FEATURE:
<223> OTHER INFORMATION: For general cloning and sequencing

<400> SEQUENCE: 139
accucucuaa accuaaaaaa aauuuucuuc ucuaaaccuc uuccuaguu aacuaggaaa        60 gagguuagag agaaauuuaa uuagguugag aggu        94

<210> SEQ ID NO 140
<211> LENGTH: 50
<212> TYPE: RNA
<213> ORGANISM: Artificial Sequence
<220> FEATURE:
<223> OTHER INFORMATION: For general cloning and sequencing

<400> SEQUENCE: 140
auauacauau acacacacac acacacucau accacauuuc agacauaaau        50

<210> SEQ ID NO 141
<211> LENGTH: 50
<212> TYPE: RNA
<213> ORGANISM: Artificial Sequence
<220> FEATURE:
<223> OTHER INFORMATION: For general cloning and sequencing

<400> SEQUENCE: 141
auauacauau acacacacac acacagacau accacauuuc agacauaaau        50

<210> SEQ ID NO 142

```
<211> LENGTH: 65
<212> TYPE: RNA
<213> ORGANISM: Artificial Sequence
<220> FEATURE:
<223> OTHER INFORMATION: For general cloning and sequencing

<400> SEQUENCE: 142
gauguaacuu uuggaauugc aaauacauau guauauauua uguaauauac auacauauau    60
acaua                                                                65

<210> SEQ ID NO 143
<211> LENGTH: 88
<212> TYPE: RNA
<213> ORGANISM: Artificial Sequence
<220> FEATURE:
<223> OTHER INFORMATION: For general cloning and sequencing

<400> SEQUENCE: 143
cugaaaugug uagauugugu gugugguguc uauguaauau auacauauac acacacacac    60
acacucauac cacauuucag acauaaau                                       88

<210> SEQ ID NO 144
<211> LENGTH: 88
<212> TYPE: RNA
<213> ORGANISM: Artificial Sequence
<220> FEATURE:
<223> OTHER INFORMATION: For general cloning and sequencing

<400> SEQUENCE: 144
cugaaaugug uagauugugu gugugguguc uauguaauau auacauauac acacacacac    60
acagacauac cacauuucag acauaaau                                       88

<210> SEQ ID NO 145
<211> LENGTH: 122
<212> TYPE: RNA
<213> ORGANISM: Artificial Sequence
<220> FEATURE:
<223> OTHER INFORMATION: For general cloning and sequencing

<400> SEQUENCE: 145
auauacauau acacacacac acacucuau accacauuuc agacauaaau gucucccac      60 agccuaaggc uguuaagggg acugaugagu cgcugggaug cgacgaaaca uuuaugucau   120
ca                                                                  122

<210> SEQ ID NO 146
<211> LENGTH: 15
<212> TYPE: DNA
<213> ORGANISM: Artificial Sequence
<220> FEATURE:
<223> OTHER INFORMATION: For general cloning and sequencing

<400> SEQUENCE: 146
gttttgtttt aatga                                                     15

<210> SEQ ID NO 147
<211> LENGTH: 15
<212> TYPE: DNA
<213> ORGANISM: Artificial Sequence
<220> FEATURE:
<223> OTHER INFORMATION: For general cloning and sequencing

<400> SEQUENCE: 147
attcactcac ctggt                                                     15
```

```
<210> SEQ ID NO 148
<211> LENGTH: 17
<212> TYPE: DNA
<213> ORGANISM: Artificial Sequence
<220> FEATURE:
<223> OTHER INFORMATION: For general cloning and sequencing

<400> SEQUENCE: 148
ctggaaaaaa gggaaaa                                                    17
```